(12) United States Patent
Chen

(10) Patent No.: US 8,889,361 B2
(45) Date of Patent: Nov. 18, 2014

(54) GENE EXPRESSION SIGNATURES IN ENRICHED TUMOR CELL SAMPLES

(75) Inventor: Wen-Tien Chen, Stonybrook, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 867 days.

(21) Appl. No.: 12/678,921

(22) PCT Filed: Sep. 19, 2008

(86) PCT No.: PCT/US2008/010881
§ 371 (c)(1),
(2), (4) Date: Aug. 10, 2010

(87) PCT Pub. No.: WO2009/038754
PCT Pub. Date: Mar. 26, 2009

(65) Prior Publication Data
US 2010/0297634 A1   Nov. 25, 2010

Related U.S. Application Data

(60) Provisional application No. 60/994,592, filed on Sep. 19, 2007.

(51) Int. Cl.
*C12Q 1/68* (2006.01)

(52) U.S. Cl.
CPC ........ *C12Q 1/6886* (2013.01); *C12Q 2600/112* (2013.01); *C12Q 2600/158* (2013.01)
USPC .......................................................... 435/6.14

(58) Field of Classification Search
None
See application file for complete search history.

(56) References Cited

U.S. PATENT DOCUMENTS

| 4,683,195 | A  | 7/1987 | Mullis et al. |
| 4,683,202 | A  | 7/1987 | Mullis |
| 4,965,188 | A  | 10/1990 | Mullis et al. |
| 4,981,785 | A  | 1/1991 | Nayak |
| 5,358,691 | A  | 10/1994 | Clark et al. |
| 5,599,677 | A  | 2/1997 | Dowell et al. |
| 5,672,480 | A  | 9/1997 | Dowell et al. |
| 5,885,530 | A  | 3/1999 | Babson et al. |
| 6,159,750 | A  | 12/2000 | Edmonds |
| 2002/0164825 | A1 | 11/2002 | Chen |
| 2003/0206901 | A1 | 11/2003 | Chen |
| 2004/0110227 | A1* | 6/2004 | Levanon et al. ............... 435/7.1 |
| 2005/0153342 | A1 | 7/2005 | Chen |
| 2005/0244843 | A1 | 11/2005 | Chen et al. |
| 2005/0250148 | A1* | 11/2005 | Bevilacqua et al. ............... 435/6 |
| 2005/0259483 | A1* | 11/2005 | Nakamura et al. ....... 365/189.07 |
| 2005/0260639 | A1* | 11/2005 | Nakamura et al. ................ 435/6 |
| 2005/0272103 | A1 | 12/2005 | Chen |
| 2006/0134653 | A1* | 6/2006 | Burgess et al. .................... 435/6 |
| 2006/0204960 | A1* | 9/2006 | Nakamura et al. ................ 435/6 |

FOREIGN PATENT DOCUMENTS

| WO | WO-2005049168 A2 * | 6/2005 |
| WO | WO-2006042005 A2 * | 4/2006 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Balzar, M. et al., The biology of the 17-1A antigen (Ep-CAM), J Mol Med, (1999), vol. 77, pp. 699-712.
Feezor, R.J. et al., Significance of Micrometastases in Colorectal Cancer, Annals of Surgical Oncology, (2002), vol. 9, No. 10, pp. 944-953.
Brandt, B.H. et al., Predictive laboratory diagnostics in oncology utilizing blood-borne cancer cells—current best practice and unmet needs, Cancer Letters, (2001), vol. 162, pp. S11-S16.
Xenidis, N. et al., Clinical relevance of circulating CK-19 mRNA-positive cells detected during the adjuvant tamoxifen treatment in patients with early breast cancer, Annals of Oncology, (2007), vol. 18, pp. 1623-1631.
Xenidis, N. et al., Predictive and prognostic value of peripheral blood Cytokeratin-19 mRNA-Positive Cells Detected by Real-Time Polymerase chain Reaction in Node-Negative Breast Cancer Patients, Journal of Clinical Oncology, (Aug. 10, 2006), vol. 24, No. 23, pp. 3756-3762.
Chen, W., Proteolytic Activity of Specialized Surface Protrusions Formed at Rosette Contact Sites of Transformed Cells, The Journal of Experimental Zoology, (1989), vol. 251, pp. 167-185.
Chen, W. et al., Local degradation of fibronectin at sites of expression of the transforming gene product pp60, Nature, (Jul. 11, 1985), vol. 316, pp. 156-158.
Chen, W. et al., Expression of tau exon 8 in different species, Neuroscience Letters, (1994), vol. 172, pp. 167-170.
Chen, W. et al., Membrane proteases as potential diagnostic and therapeutic targets for breast malignancy, Breast Cancer Research and Treatment, (1994), vol. 31, pp. 217-226.
Chen, W. Proteases Associated with Invadopodia, and Their Role in Degradation of Extracellular Matrix, Enzyme Protein, (1996), vol. 49, pp. 59-71.
Friedl, P. et al., Tumour-Cell Invasion and Migration: Diversity and Escape Mechanisms, Nat Rev Cancer, (2003), vol. 3, pp. 362-374.
Goldstein, L.A. et al., Molecular cloning of seprase: a serine integral membrane protease from human melanoma, Biochimica et Biophysica Acta, (1997), vol. 1361, pp. 11-19.
Xi, L. et al., Optimal Markers for Real-Time Quantitative Reverse Transcription PCR Detection of Circulating Tumor Cells from Melanoma, Breast, Colon, Esophageal, Head and Neck, and Lung Cancers, Clinical Chemistry, (2007), vol. 53, No. 7, pp. 1206-1215.
Iakovlev, V.V. et al., Quantitative detection of circulating epithelial cells by Q-RT-PCR, Breast Cancer Res Treat, (2008), vol. 107, pp. 145-154.
Matsunami, K. et al., Detection of Bone Marrow Micrometastis in Gastric Cancer Patients by Immunomagnetic Separation, Annals of Surgical Oncology, (2003), vol. 10, No. 2, pp. 171-175.

(Continued)

*Primary Examiner* — James Martinell
(74) *Attorney, Agent, or Firm* — Scully, Scott, Murphy & Presser, P.C.

(57) ABSTRACT

The invention is embodied in methods for finding gene expression signatures of circulating melanoma cells, ovarian, breast, colorectal cancer cells, and circulating endothelial progenitor cells, which signatures are effective in distinguishing the circulating cancer cell from normal circulating cells and can also distinguish between different types of circulating cancer cells.

8 Claims, 22 Drawing Sheets

(56) References Cited

OTHER PUBLICATIONS

Monsky, W. L. et al., A Potential Marker Protease of Invasiveness, Seprase, Is Localized on Invadopodia of Human Malignant Melanoma Cells, Cancer Research, (Nov. 1, 1994), vol. 54, pp. 5702-5710.
Yao, J. et al., Combined cDNA Array Comparative Genomic Hybridization and Serial Analysis of Gene Expression Analysis of Breast Tumor Progression, Cancer Res, (2006), vol. 66, pp. 4065-4078.
Pantel, K. et al., Detection, clinical relevance and specific biological properties of disseminating tumour cells, Nature Reviews, (May 2008), vol. 8, pp. 329-340.
Zucker, S. et al., Critical appraisal of the use of matrix metalloproteinase inhibitors in cancer treatment, Oncogene, (2000), vol. 19, pp. 6642-6650.
Xenidis, N. et al., Peripheral blood circulating cytokeratin-19 mRNA-positive cells after the completion of adjuvant chemotherapy in patients with operable breast cancer, Annals of Oncology, (2003), vol. 14, pp. 849-855.
Sawyers, C.L. et al., The cancer biomarker problem, Nature, (Apr. 3, 2008) vol. 452, pp. 548-552.
Tsuda, H. et al., Identification of DNA copy number changes in microdissected serous ovarian cancer tissue using a cDNA microarray platform, Cancer Genetics and Cytogenetics, (2004), vol. 155, pp. 97-107.
Winter, M.J. et al., The Epithelial Cell Adhesion Molecule (Ep-CAM) as a Morphoregulatory Molecule Is a Tool in Surgical Pathology, (Dec. 2003), vol. 163, No. 6, pp. 2139-2148.
Wilhelm, M.C. et al., Nonpalpable Invasive Breast Cancer, Ann Surg., (1991), vol. 213, No. 6, pp. 600-605.
Adib, T.R. et al., Predicting biomarkers for ovarian cancer using gene-expression microarrays, British Journal of Cancer, (2004), vol. 90, pp. 686-692.
Allard, W.J. et al., Tumor Cells Circulate in the Peripheral Blood of All Major carcinomas but not in Healthy Subjects or Patients With Nonmalignant Diseases, Clin Cance Res, (2004), vol. 10, pp. 6897-6904.
Allard, W.J. et al., Tumor Cells Circulate in the Peripheral Blood of All Major carcinomas but not in Healthy Subjects or Patients With Nonmalignant Diseases, Clin Cance Res, (2004), vol. 10, pp. 6897-6904, Supplemental Data File.
Aoyama, A. et al., a 170-kDa membrane-bound protease is associated with the expression of invasiveness by human malignant melanoma cells, Proc. Natl. Acad. Sci. USA, (Nov. 1990), vol. 87, pp. 8296-8300.
Bast, Jr., R.C. et al., Status of Tumor Markers in Ovarian Cancer Screening, Journal of Clinical Oncology, (2003), vol. 21, No. 10s, pp. 200s-205s.
Bayani, J. et al., Parallel Analysis of Sporadic Primary Ovarian Carcinomas by Spectral Karyotyping, Comparative Genomic Hybridization, and Expression Microarrays, Cancer Res, (2002), vol. 62, pp. 3466-3476.
Beerepoot, L.V. et al., Increased levels of viable circulating endothelial cells are an indicator of progressive disease in cancer patients, Annals of Oncology, (2004), vol. 15, pp. 139-145.
Berchuck, A. et al., Patterns of Gene Expression That Characterize Long-term Survival in Advanced Stage Serous Ovarian Cancers, Clin Cancer Res, (2005), vol. 11, 3686-3696.
Braun, S. et al., Tumor-Antigen Heterogeneity of Disseminated Breast Cancer Cells: Implications for Immunotherapy of Minimal Residual Disease, Int. J. Cancer, (1999), vol. 84, pp. 1-5.
Braun, S. et al., Occult Tumor Cells in Bone Marrow of Patients With Locoregionally Restricted Ovarian Cancer Predict Early Distant Metastatic Relapse, Journal of Clinical Oncology, (Jan. 15, 2001), vol. 19, No. 2, pp. 368-375.
Chen, W. et al., Expression of Transformation-associated Protease(s) That Degrade Fibronectic at Cell Contact Sites, The Journal of Cell Biology, (Apr. 1984), vol. 98, pp. 1546-1555.
Choesmel, V. et al., A Relevant Immunomagnetic Assay to Detect and Characterize Epithelial Cell Adhesion Molecule-Positive Cells in Bone Marrow from Patients with Breast Carcinoma, Cancer, (Aug. 15, 2004), vol. 101, No. 4, pp. 693-703.
Coopman, P.J. et al., Integrin $\alpha 3\beta 1$ Participates in the Phagocytosis of Extracellular Matrix Molecules by Human Breast Cancer Cells, Molecular Biology of the Cell, (Nov. 1996), vol. 7, pp. 1789-1804.
Cristofanilli, M. et al., Circulating Tumor Cells, Disease Progression, and Survival in Metastatic Breast Cancer, New England Journal of Medicine, (Aug. 19, 2004), vol. 351, No. 8, pp. 781-791.
De Kok, J.B. et al., Normalization of gene expression measurements in tumor tissues: comparison of 13 endogenous control genes, Laboratory Investigation, (2005), vol. 85, pp. 154-159.
Fehm, T. et al., Cytogenetic Evidence That Circulating Epithelial Cells in Patients with Carcinoma Are Malignant, Clin Cancer Res, (2002), vol. 8, pp. 2073-2084.
Flatmark, K. et al., Immunomagnetic Detection of Micrometastatic Cells in Bone Marrow of Colorectal Cancer Patients, Clin Cancer Res, (2002), vol. 8, pp. 444-449.
Ghersi, G. et al., Regulation of fibroblast migration on collagenous matrix by a cell surface peptidase complex, J. Biol. Chem., (2002), vol. 277, No. 32, pp. 29231-29241.
Glaves, D. et al., Correlation between circulating cancer cells and incidence of metastases, Br. J. Cancer, (1983), vol. 48, pp. 665-673.
Goldstein, L.A. et al., Identification of an Alternatively Spliced Seprase mRNA That Encodes a Novel Intracellular Isoform, J. Biol. Chem. (2000), vol. 275, pp. 2554-2559.
Goto, T. et al., Gene expression profiles with cDNA microarray reveal RhoGDI as a predictive marker for paclitaxel resistance in ovarian cancers, Oncology Reports, (2006), vol. 15, pp. 1265-1271.
Gross, H. et al., Model study detecting breast cancer cells in peripheral blood mononuclear cells at frequencies as low as 10-7, Proc. Natl. Acad. Sci. USA, (Jan. 1995), vol. 92, pp. 537-541.
Hill, J.M. et al., Circulating Endothelial Progenitor Cells, Vascular Function, and Cardiovascular Risk, New England Journal of Medicine, (Feb. 13, 2003), vol. 348, No. 7, pp. 593-600.
Hough, C.D. et al., Large-Scale Serial Analysis of Gene Expression Reveals Genes Differentially Expressed in Ovarian Cancer, Cancer Res, (2000), vol. 60, pp. 6281-6287.
Ignatiadis, M. et al., Prognostic Value of the Molecular Detection of Circulating Tumor Cells Using a Multimarker Reverse Transcription-PCR Assay for Cytokeratin 19, Mammaglobin A, and HER2 in Early Breast Cancer, Clin Cancer Res, (2008), vol. 14, pp. 2593-2600.
Ignatiadis, M. et al., Different Prognostic Value of Cytokerativ-19 mRNA-Positive Circulating Tumor Cells According to Estrogen Receptor and HER2 Status in Early-Stage Breast Cancer, Journal of Clinical Oncology, (Nov. 20, 2007), vol. 25, No. 33, pp. 5194-5202.
Jazaeri, A.A. et al., Gene Expression Profiles Associated with Response to Chemotherapy in Epithelial Ovarian Cancers, Clin Cancer Res, (2005), vol. 11, pp. 6300-6310.
Karczewski, D.M. et al., The Efficiency of an Autotransfusion System for Tumor Cell Removal from Blood Salvaged During Cancer Surgery, Anesth Analg, (1994), vol. 78, pp. 1131-1135.
Koch, M. et al., Comparative Analysis of Tumor Cell Dissemination in Mesenteric, Central, and Peripheral Venous Blood in Patients With Colorectal Cancer, Arch Srug, (Jan. 2001), vol. 136, pp. 85-89.
Liang, Z. et al., Inhibition of Breast Cancer Metastasis by Selective Synthetic Polypeptide against CXCR4, Cancer Res, (2004), vol. 64, pp. 4302-4308.
Liefers, G. et al., Micrometastases and Survival in Stage II Colorectal Cancer, The New England Journal of Medicine, (1998), vol. 339, pp. 223-228.
Liotta, L.A. et al., Quantitative Relationships of Intravascular Tumor Cells, Tumor Vessels, and Pulmonary Metastases following Tumor Implantation, Cancer Res, (1974), vol. 34, pp. 997-1004.
Litvinov, S.V. et al., Ep-CAM: A Human Epithelial Antigen Is a Homophilic Cell-Cell Adhesion Molecule, The Journal of Cell Biology, (Apr. 1994), vol. 125, No. 2, pp. 437-446.
Luzzi, K.J. et al., Dormancy of Solitary Cells after Successful Extravasation and Limited Survival of Early Micrometastases, AJP, (Sep. 1998), vol. 153, No. 3, pp. 865-873.
Mareel, M. et al., Clinical, Cellular, and Molecular Aspects of Cancer Invasion, Physiol Rev, (2003), vol. 83, pp. 337-376.
Molnar, B. et al., Circulating Tumor Cell Clusters in the Peripheral Blood of Colorectal Cancer Patients, Clin Cancer Res, (2001), vol. 7, pp. 4080-4085.

(56) References Cited

OTHER PUBLICATIONS

Monsky, W.L. et al., Binding and Localization of Mr 72,000 Matrix Metalloproteinase at Cell Surface Invadopodia, Cancer Res, (1993), vol. 53, pp. 3159-3164.

Wang, X. et al., Ovarian cancer, the coagulation pathway, and inflammation, Journal of Translational Medicine, (Jun. 21, 2005), vol. 3, No. 25, pp. 1-20.

Mueller, S.C. et al., A Novel Protease-docking Function of Integrin at Invadopodia, The Journal of Biological Chemistry, (1999), vol. 274, No. 35, pp. 24947-24952.

Mueller, S.C. et al., Cellular invasion into matrix beads: localization of $\beta 1$ intergrins and fibronectin to the invadopodia, Journal of Cell Science, (1991), vol. 99, pp. 213-225.

Mueller, S.C. et al., Tyrosine Phosphorylation of Membrane Proteins Mediates Cellular Invasion by Transformed Cells, The Journal of Cell Biology, (Dec. 1992), vol. 119, No. 5, pp. 1309-1325.

Nakahara, H. et al., A Mechanism for Regulation of Melanoma Invasion: Ligation of $\alpha 6\beta 1$ Integrin by Laminin G Peptides, J. Biol. Chem. (1996), vol. 271, pp. 27221-27224.

Nakahara, H. et al., Activation of $\beta 1$ Integrin Signaling Stimulates Tyrosine Phosphorylation of p190 RhoGAP and Membrane-protrusive Activites at Invadopodia, J. Biol. Chem., (1998), vol. 271, pp. 9-12.

Nakahara, H. et al., Transmembrane/cytoplasmic domain-mediated membrane type 1-matrix metalloprotease docking to invadopodia is required for cell invasion, Proc. Natl. Acad. Sci. USA, (Jul. 1997), vol. 94, pp. 7959-7964.

Newton, T.R. et al., Expression profiling correlates with treatment response in women with advanced serous epithelial ovarian cancer, Int. J. Cancer, (2006), vol. 119, pp. 875-883.

Ottaiano, A. et al., Overexpression of Both CXC Chemokine Receptor 4 and Vascular Endothelial Growth Factor Proteins Predicts Early Distant Relapse in Stage II-III Colorectral Cancer Patients, Clin Cancer Res, (2006), vol. 12, pp. 2795-2803.

Ozols, R.F. et al., Focus on epithelial ovarian cancer, Cancer Cell, (Jan. 2004), vol. 5, pp. 19-24.

Pantel, K. et al., Detection and Clinical Importance of Micrometastatic Disease, Journal of the National Cancer Institute, (Jul. 7, 1999) vol. 91, No. 13, pp. 1113-1124.

Pavlaki, M. et al., A Conserved Sequence within the Propeptide Domain of Membrane Type 1 Matrix Metalloproteinase Is Critical for Function as an Intramolecular Chaperone, J, Biol. Chem., (2002), vol. 277, pp. 2740-2749.

Pearson, W.R. et al., Improved tools for biological sequence comparison, Proc. Natl. Acad. Sci. USA, (Apr. 1988), vol. 85, pp. 2444-2448.

Peck, K. et al., Detection and Quantitation of Circulating Cancer Cells in the Peripheral Blood of Lung Cancer Patients, Cancer Res, (1998), vol. 58, pp. 2761-2765.

Pineiro-Sanchez, M.L. et al., Identification of the 170-kDa Melanoma Membrane-bound Gelatinase (Seprase) as a Serine Intergral Membrane Protease, (Mar. 21, 1997), vol. 272, No. 12, pp. 7595-7601.

Racila, E. et al., Detection and characterization of carcinoma cells in the blood, Proc. Natl. Acad. Sci. USA, (Apr. 1998), vol. 95, pp. 4589-4594.

Ramaswamy, S. et al., A molecular signature of metastasis in primary solid tumors, Nature Genetics, (Jan. 2003), vol. 33, pp. 49-54.

Saga, S. Enhanced Fibronectin Receptor Expression in Rous Sarcoma Virus-induced Tumors, Cancer Res, (1988), vol. 48, pp. 5510-5513.

Sambrook, J. et al., Molecular Cloning: A Laboratory Manual, Cold Spring Harbor Press, (1989), pp. 7.39-7.52.

Sambrook, J. et al., Molecular Cloning: A Laboratory Manual, Cold Spring Harbor Press, (1989), pp. 9.31-9.58.

Schaner, M.E. et al., Variation in gene expression patterns in effusions and primary tumors from serous ovarian cancer patients, Molecular Cancer, (2005), vol. 4, No. 26, pp. 1-14.

Shipitsin, M. et al., Molecular Definition of Breast Tumor heterogeneity, Cancer Cell, (Mar. 2007), vol. 11, pp. 259-273.

Smirnov, D.A. et al., Global Gene Expression Profiling of Circulating Tumor Cells, Cancer Res, (2005), vol. 65, pp. 4993-4997.

Smirnov, D.A. et al., Global Gene Expression Profiling of Circulating Endothelial Cells in Patients with Metastatic Carcinomas, Cancer Res, (2006), vol. 66, pp. 2918-2922.

Smith, T.F. et al., Comparison Advances in Applied Mathematics, (1981) vol. 2, pp. 482-489.

Sood, A.K. et al., Biological Significance of Focal Adhesion Kinase in Ovarian Cancer, American Journal of Pathology, (Oct. 2004), vol. 165, No. 4, pp. 1087-1095.

Stathopoulou, A. et al., A highly specific real-time RT-PCR method for the quantitative determination of CK-19 mRNA positive cells in peripheral blood of patients with operable breast cancer, Int. J. Cancer, (2006), vol. 119, pp. 1654-1659.

Stracke, M.L. et al., Identification, Purification, and Partial Sequence Analysis of Autotaxin, a ovel Motility-stimulating Protein, The Journal of Biological Chemistry, (1992), vol. 267, No. 4, pp. 2524-2529.

Tarin, D., New Insights into the Pathogenesis of Breast Cancer Metastasis, Breast Disease, (2006), vol. 26, pp. 13-25.

Thurm, H. et al., Rare Expression of Epithelial Cell Adhesion Molecule on Residual Micrometastatic Breast Cancer Cells after Adjuvant Chemotherapy, Clin Cancer Res, (2003), vol. 9, pp. 2598-2604.

Vona, G. et al., Isolation by Size of Epithelial Tumor Cells: A New Method for the Immunomorphological and Molecular Characterization of Circulating Tumor Cells, American Journal of Pathology, (Jan. 2000), vol. 156, No. 1, pp. 57-63.

Walsh, J.M.E. et al., Colorectal Cancer Screening Clinical Applications, JAMA, (Mar. 12, 2003), vol. 289, No. 10, pp. 1297-1302.

Walsh, J.M.E. et al., Colorectal Cancer Screening Scientific Review, JAMA, (Mar. 12, 2003), vol. 289, No. 10, pp. 1288-1296.

Boccaccio, C. et al., Invasive growth: a MET-driven genetic programme for cancer and stem cells, Nature Reviews Cancer, (Aug. 2006), vol. 6, pp. 637-645.

Chen, W. et al., Specialized Surface Protrusions of INvasive Cells, Invadopodia and Lamellipodia, Have Differential MT1-MMP, MMP-2, and TIMP-2 Localization, Annals New York Academy of Sciences, (1999), vol. 878, pp. 361-371.

Wharton, R.Q. et al., Increased Detection of Circulating Tumor cells in the Blood of Colorectal Carcinoma Patients Using Two Reverse Transcription-PCR Assays and Multiple Blood Samples, Clin Cancer Res, (1999), vol. 5, pp. 4158-4163.

Kelly, T. et al., Invadopodia Promote Proteolysis of a Wide Variety of Extracellular Matrix Proteins, Journal of Cellular Physiology, (1994), vol. 158, pp. 299-308.

Weitz, J. et al., Detection of Disseminated Colorectal Cancer Cells in Lymph Nodes, Blood and Bone Marrow, Clinical Cancer Research, (Jul. 1999), vol. 5, pp. 1830-1836.

\* cited by examiner

Fig.18
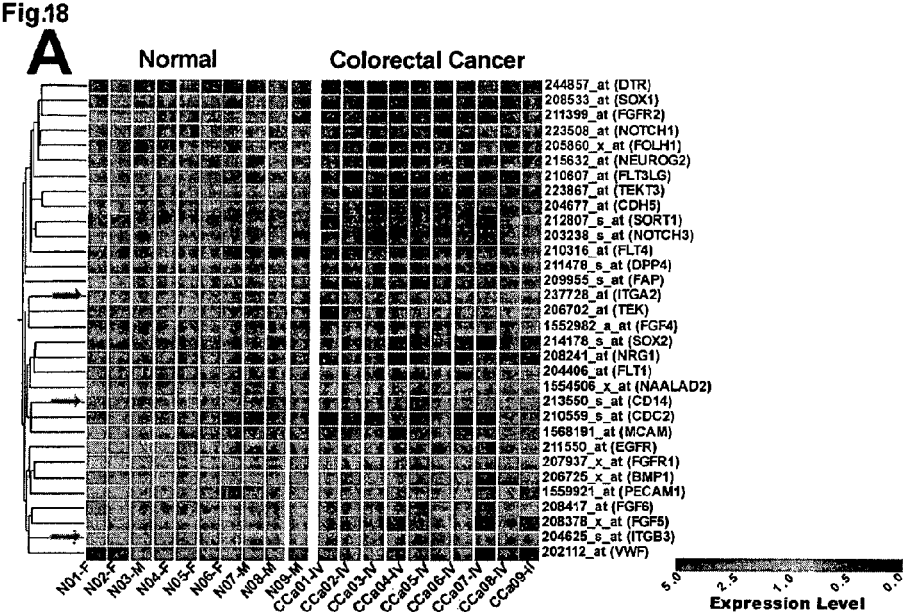
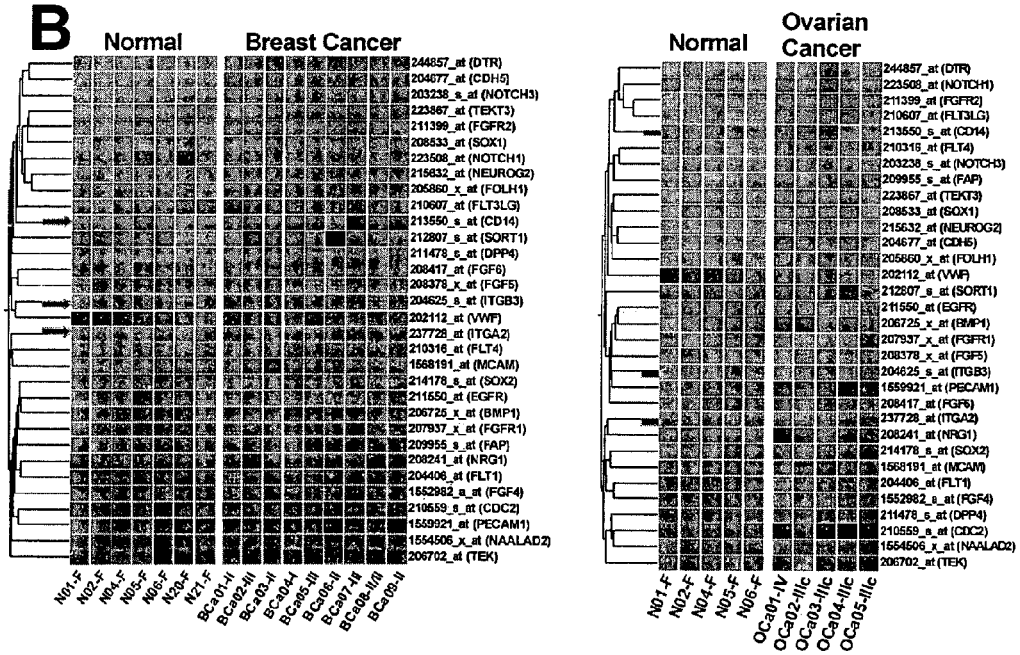

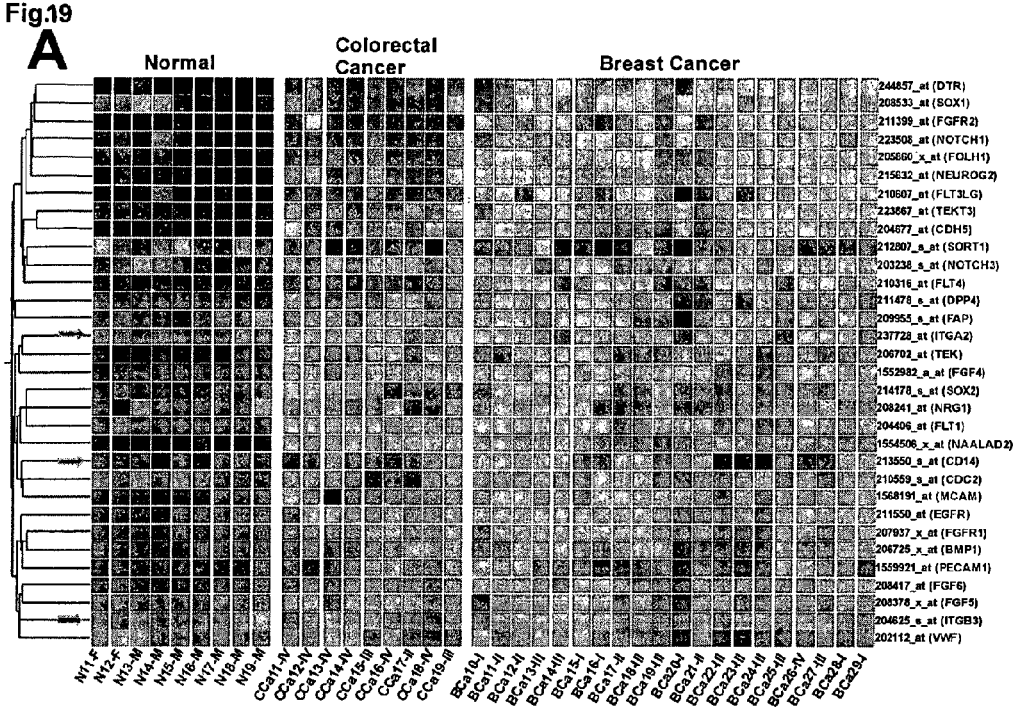
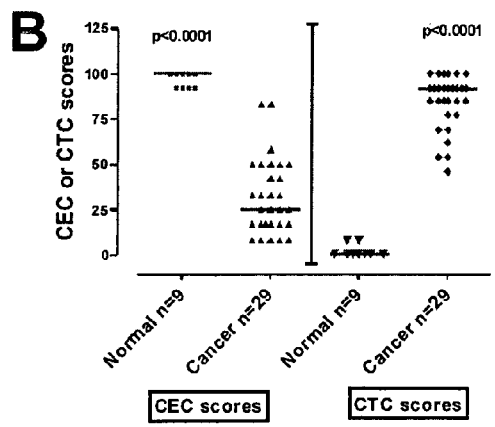
Fig.19

Fig. 10
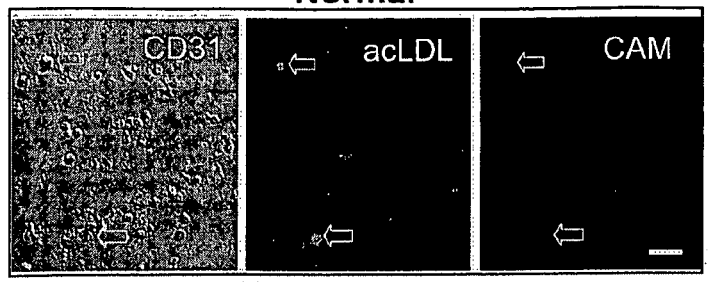
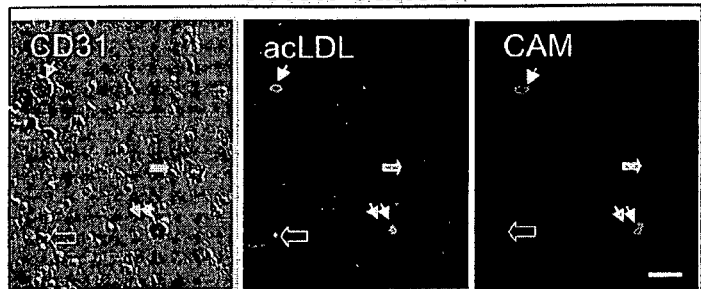
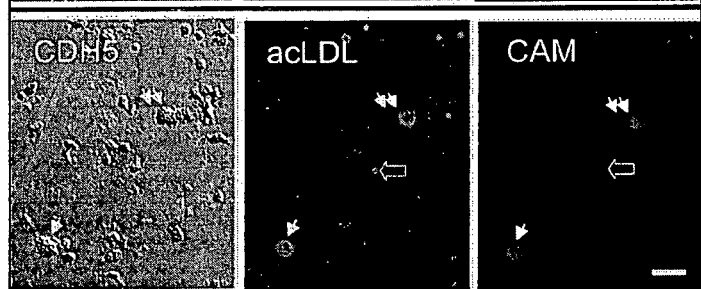
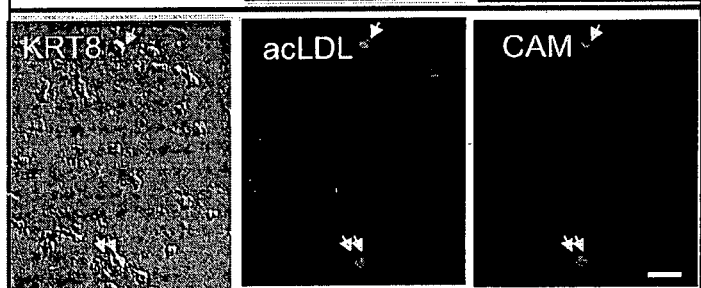
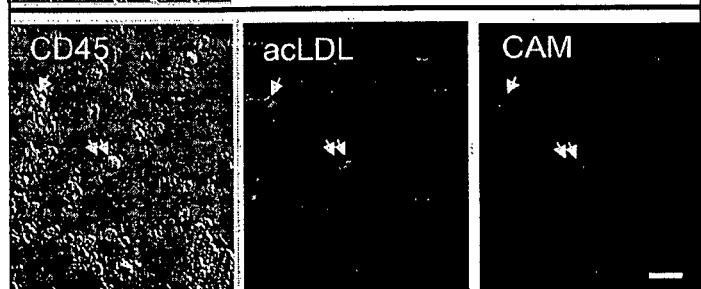

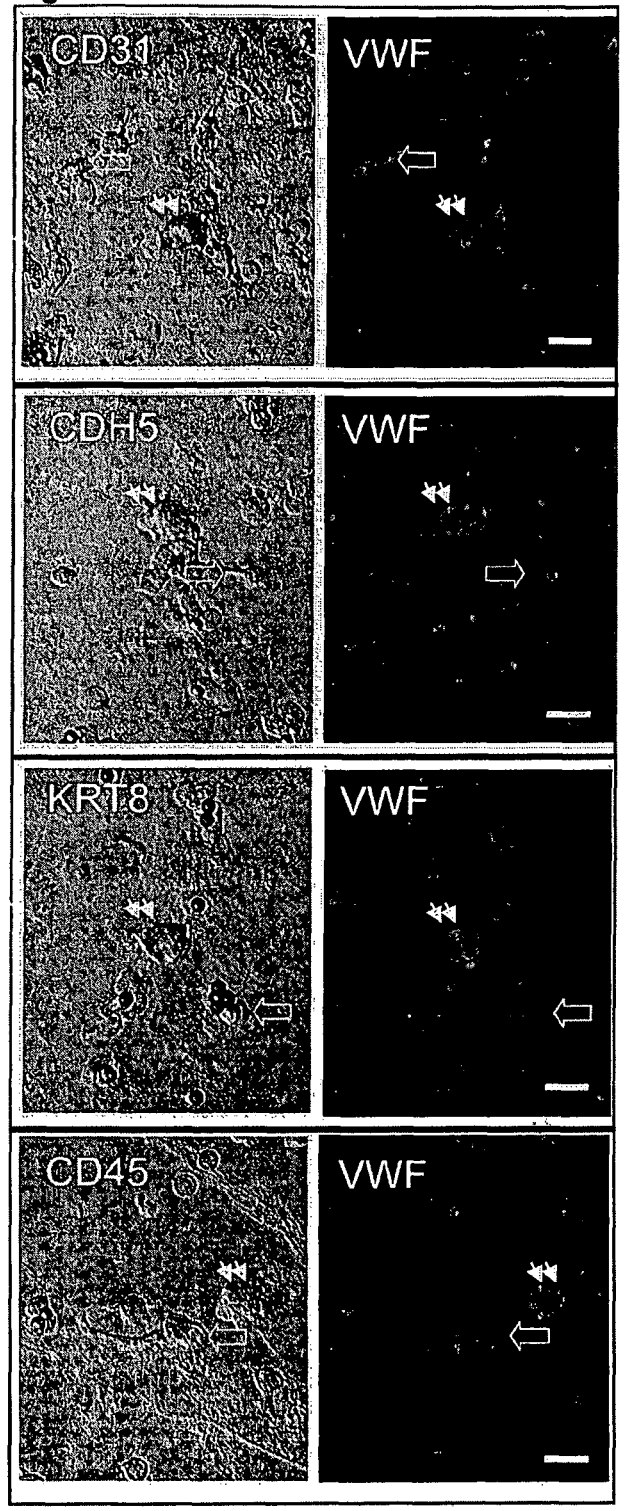

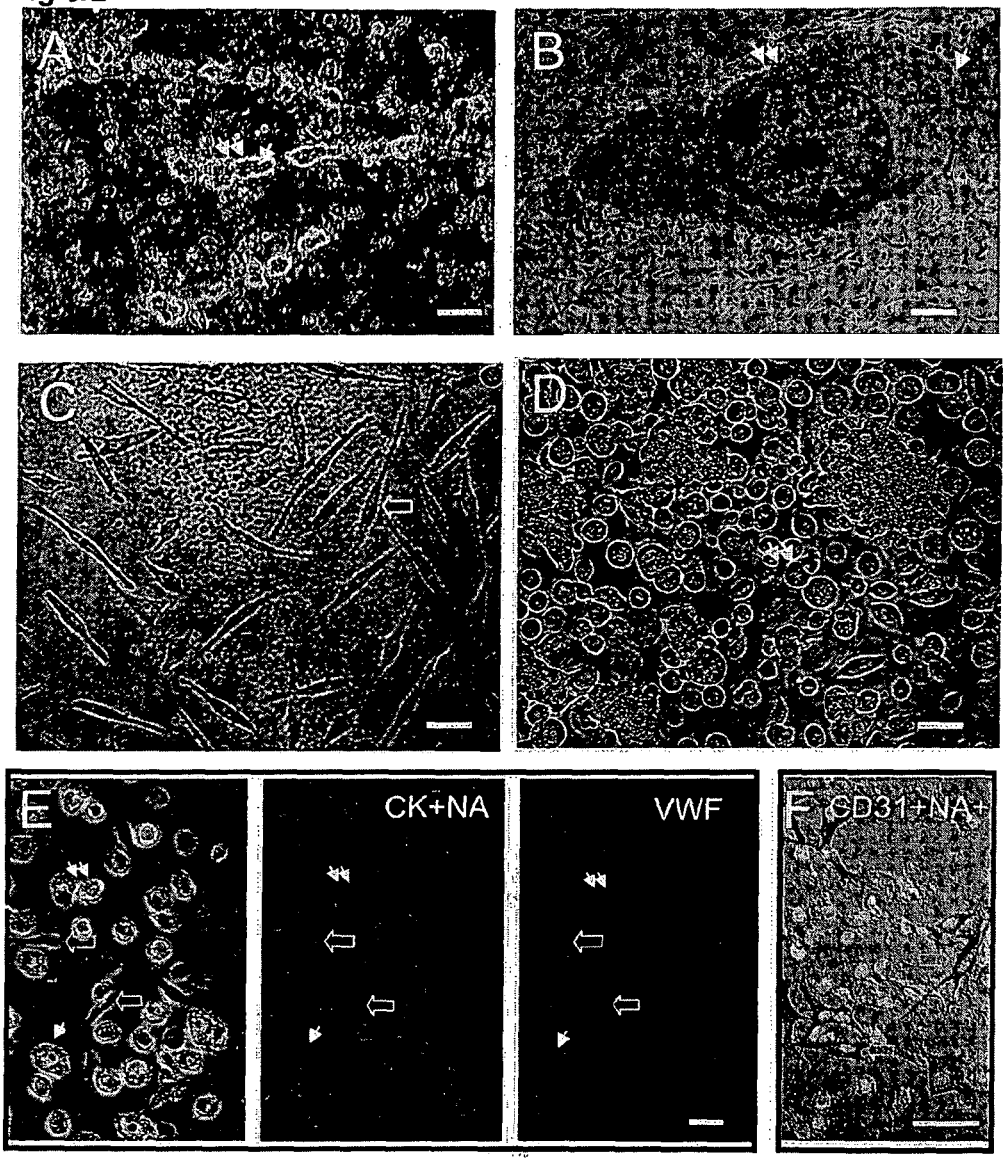

GENE EXPRESSION SIGNATURES IN ENRICHED TUMOR CELL SAMPLES

This application claims priority to U.S. Provisional Patent Application 60/994,592, filed Sep. 19, 2007 which is incorporated herein by reference in its entirety for all purposes.

This invention was made with government support under Grant No. R42CA108247 and R41CA103462 awarded by the National Institutes of Health. The Government has certain rights in this invention.

FIELD OF THE INVENTION

Embodiments of the present invention relate to methods of finding gene expression signatures in rare cells in blood and other body fluids. In particular, these embodiments relate to methods of identifying and distinguishing endothelial progenitor cells in the blood from circulating tumor cells including metastatic cells and, further, distinguishing among circulating tumor cells that originate from diverse tumors of epithelial lineage.

BACKGROUND OF THE INVENTION

Malignant tumors and metastatic lesions of epithelial tissues are the most common form of cancer and are responsible for the majority of cancer-related deaths (Chambers et al., 2002; Pantel and Brakenhoff, 2004). Because of progress in the surgical treatment of these tumors, mortality is linked increasingly to early metastasis and recurrence, which is often occult at the time of primary diagnosis (Racila et al., 1998; Pantel et al., 1999). For example, the remote anatomical location of the pancreas and other gastrointestinal (GI) organs makes it unlikely that pancreatic and other GI cancers will be detected before they have invaded neighboring structures and grown to tumors larger than 1-cm (Compton, 2003; Flatmark et al., 2002; Koch et al., 2001; Liefers et al., 1998; Matsunami et al., 2003; Nomoto et al., 1998; Pantel et al., 1999; Walsh and Terdiman, 2003; Weihrauch, 2002). Even with respect to breast cancers, 12-37% of small tumors of breast cancer (<1 cm) detected by mammography already have metastasized at diagnosis (Chadha M et al., 1994; Wilhelm M C et al., 1991).

During the process of metastasis, cancerous cells detach from the primary tumor, migrate through the circulation, seed into secondary organs and grow a metastatic lesion. A rational strategy to diagnose cancer, therefore, would be to detect circulating tumor cells (CTC) in the peripheral blood after greater than 1,000-fold enrichment of metastatic tumor cells (Pantel et al., 1999). However, CTCs are currently detected by epithelial lineage markers or tumor-associated markers that are neither sufficient in distinguishing cancer from normal cells nor adequate in identifying specific types of tumors. For example, current CTC enrichment methods using an anti-Epithelial Cell Adhesion Molecule (EpCAM) antibody may entail a substantial loss of metastatic tumor cells due to down-regulation of the EpCAM gene in these cells (Pantel et al., 1999; Sabile et al., 1999; Thurm et al., 2003; Choesmel et al., 2004). Therefore, gene expression profiles (GEP) of CTCs enriched by anti-EpCAM antibody magnetic cell separation may be misleading in that the cells in which they appear may be a selected subpopulation of CTCs that have upregulated EpCAM expression (Smirnov et al., 2005).

Molecular profiling of gene expression in primary and metastatic tumors is a powerful tool that can be used to diagnose tumor types and categorize them with respect to projected prognosis and therapeutic responsiveness (Berchuck et al., 2005; Jazaeri et al., 2005; Goto et al., 2006; Newton et al., 2006). The profiling is sometimes performed on tumor cells concentrated using antibodies against epithelial surface antigens in immuno-magnetic cell separation methods (Smirnov et al., 2005; Bayani et al., 2002; Tsuda et al., 2004; Yao et al., 2006; Shipitsin et al., 2007). In the past five years there have been more than 1,000 publications describing gene expression profiles of epithelial cancers mostly focusing on primary and secondary solid tumors. Only one paper compared gene expression profiles of cells isolated from blood of healthy subjects and cancer patients (Smirnov et al., 2005). The isolation step employed an antibody against the epithelial cell adhesion molecule (EpCAM). Antibodies against EpCAM (also known as tumor-associated calcium signal transducer 1, TACSTD1 or GA733) are commonly used in immuno-magnetic cell separation of CTCs, but EpCAM is expressed on both normal and malignant cells (Litvinov et al., 1994; Balzar et al., 1999; Winter et al., 2003). It is therefore not clear that the comparison made by Smirnov et al. was entirely valid.

Evidence has accumulated in the literature showing that epithelial tumor cells found in the circulation represent the earliest sign of metastasis formation and that circulating tumor cells ("CTCs") can be considered an independent diagnostic for cancer progression of carcinomas (Beitsch and Clifford, 2000; Brandt et al., 2001; Feezor et al., 2002; Fehm et al., 2002; Ghossein et al., 1999; Glaves, 1983; Karczewski et al., 1994; Koch et al., 2001; Liefers et al., 1998; Luzzi et al., 1998; Matsunami et al., 2003; Molnar et al., 2001; Wang et al., 2000; Weitz et al., 1999; Wharton et al., 1999; Racila et al., 1998; Pantel et al., 1999). Accordingly, reliable procedures to isolate cancer cells from the bloodstream would have significant impact in both clinical diagnostic and therapeutic applications of cancer (Racila et al., 1998; Pantel et al., 1999). A new tumor staging, called Stage Mi, has been proposed to indicate the presence of tumor cells in the circulation of patients with cancers. The staging warrants the development of a blood test that could detect CTCs. However, CTCs are rare. In general, therefore, such tests require tumor cell enrichment methods that can increase detection sensitivity, advantageously by at least one order of magnitude (Pantel et al., 1999), over existing methods.

Cytokeratins (KRTs) are cytoskeletal proteins specifically expressed in cells of the epithelial lineage. They have become the standard markers for the detection of CTCs or tumor cells disseminated in bone marrow (DTCs) in patients with epithelial tumors such as breast, prostate, colon or lung cancer (Pantel et al., 2008; Paterlini-Brechot and Benali, 2007). Some CTCs are now being viewed as a type of stem or progenitor cell of epithelial lineage that differentiates to form secondary tumors (Braun et al., 2007; Shipitsin et al., 2007; Pantel et al., 2008; Paterlini-Brechot and Benali, 2007). However, it is not known to date which member(s) of the KRT family are specific for the cancer stem or progenitor cell type among CTCs. Indeed, some KRTs used in detecting CTCs were found to be expressed also in subpopulations of normal circulating cells (Pantel et al., 2008; Paterlini-Brechot and Benali, 2007). CTCs of epithelial cancers are thought to express markers of multiple cell lineages, including but not limited to stem cell genes or factors (SCFs), and are thought to be capable of proliferating and differentiating into the epithelial phenotype wherein not only cytokeratins (KRTs) are expressed but also cadherins (CDHs), mucins (MUCs), integrins (ITGs), epithelial membrane antigens (EMA) and tumor-associated antigens (TAAs). Although some of these differentiated epithelial markers have been used to isolate and identify CTCs and DTCs (Pantel et al., 2008), the true identity of the tumor progenitor cell population remains undefined for the majority of human cancers due to the lack of markers that are specific for that type of CTC (van't Veer and Bernards, 2008; Sawyers, 2008).

Current nucleic acid-testing by DNA microarray or quantitative real-time PCR (qPCR) has improved resolution in the detection of CTCs by means of cut-off values of "selected" marker transcript numbers, above which these transcripts can be considered as tumor cell-derived (Ignatiadis et al., 2008; Xenidis et al., 2006). There remains an unresolved quantification problem, however: there are no 'ideal' endogenous control genes; that is, genes that do not deviate between tumor and normal cells in blood from different individuals (de Kok et al., 2005).

Organ-specific markers (mammoglobulin, HER-2, CA-125, CEA and PSA) have been used to identify CTCs that have emigrated from their original organs such as breast, ovary, colon and prostate. However, false negative results can occur, since these antigens are not present in all the cells of a tumor (Paterlini-Brechot and Benali, 2007). In addition, these markers were not specific for a given organ. Gene expression analysis of a subpopulation of CTCs isolated by antibody against EpCAM from patients with metastatic cancer revealed that the KRT19 and AGR2 (hAG-2) genes were expressed in the majority of the metastatic samples, whereas S100A14, S100A16, and CEACAM5 genes showed expression restricted to the metastatic colorectal and breast cancer samples; FABP1 and KRT20 genes showed expression patterns associated with colorectal cancer; those of the SCGB2A1, SCGB2A2, and PIP genes were associated with breast cancer (Smirnov et al., 2005). Since EpCAM is commonly expressed on normal and malignant cells (Litvinov et al., 1994; Balzar et al., 1999; Winter et al., 2003) and EpCAM expression varies in different tumors (Braun et al., 1999; Thurm et al., 2003), the gene expression profiles of EpCAM-expressing circulating cells previously described (Smirnov et al., 2005) could target a subpopulation of circulating cells in metastatic cancer patients including normal inflammatory and lymphoid cells.

In cancer patients, the number of CTCs or exfoliated abnormal cells (neoplastic cells) in blood is generally very small compared to the number of non-neoplastic cells. Therefore, the detection of exfoliated abnormal cells by routine cytopathology is often limited. Further, exfoliated cells are frequently highly heterogeneous, being composed of many different cell types. Compounding this heterogeneity problem, the frequency of neoplastic cells present in each clinical specimen is variable, which biases and complicates the quantification of differential gene expression in randomized mixed populations. Apoptotic and necrotic cells are common in larger tumors, peripheral blood and ascites. These cells do not contain high quality RNA and thus present technical problems for molecular analyses (Karczewski et al., 1994).

The detection of metastatic cells is particularly challenging. Although primary cancers frequently shed neoplastic cells into the circulation at an early stage of metastases formation (Fidler, I. J., *European Journal of Cancer* 9:223-227, 1973; Liotta L. A. et al., Cancer Research 34:997-1004, 1974) in large numbers, only a minor subpopulation of such cells (one in a thousand to one in a million) are metastatic (Glaves, D., Br. J. Cancer 48:665-673, 1983), evidently because few shed cancer cells survive for long in the circulation (Weiss and Glaves, 1983; Karczewski et al., 1994)

A number of cell enrichment methods for circulating tumor cells have been described:

a) Microdissection can be used to isolate rare tumor cells one by one (Suarez-Quian et al., 1999). This method typically has several limitations: (1) the subsequent sample processing is complicated, (2) cell viability cannot readily be established, and (3) selection of the cells to be dissected is based mainly on morphological criteria, which has a high frequency of giving rise to false-positive results.

b) Physical characteristics of tumor cells, such as shape, size, density or electrical charge, can also be used (Vona et al., 2000). Several density gradient centrifugation methods have been developed to enrich tumor cells in nucleated blood cells (devoid of mature red blood cells). Density gradient centrifugation methods can achieve 500 to 1,000-fold cell enrichment. The enriched tumor cells can then be subjected to molecular analysis using highly sensitive assays such as immunocytochemistry and reverse transcriptase polymerase chain reaction (RT-PCR) which may be used to amplify putative tumor markers or epithelial markers such as prostate specific antigen (PSA) mRNA or cytokeratin 19 mRNA (Peck et al., 1998). However, these methods may not effectively enrich viable tumor cells from normal cells. That is, 500-1,000 fold cell enrichment is often found to be relatively modest enrichment which generates substantial background noise adversely affecting further molecular analysis. In addition, enrichment methods based on physical separation techniques are often cumbersome, lengthy, and involve steps (e.g. more than 2-3 rounds of centrifugation) that can result in cellular damage.

c) Antibody-based techniques are a more recent development. Immunoaffinity methods include affixing an antibody to a physical carrier or fluorescent label. Sorting steps can then be used to positively or negatively enrich for the desired cell type after the antibody binds to its target present on the surface of the cells of interest. Such methods include affinity chromatography, particle magnetic separation, centrifugation, or filtration, and flow cytometry (including fluorescence activated cell sorting; FACS).

Flow cytometry or a fluorescence activated cell sorter ("FACS") detects and separates individual cells one-by-one from background cells. In model experiments, this method can detect breast carcinoma cells (Gross et al., 1995) and endothelial progenitor cells (Hill et al., 2003) in the mononuclear cell fraction that had been enriched from the peripheral blood by density gradient centrifugation. Furthermore, FACS can detect naturally occurring breast and prostate tumor cells in blood after an enrichment step using antibody-coated magnetic microbeads (Racila et al., 1998; Beitsch and Clifford, 2000). However, cells that exist in clusters or clumps are discarded during the FACS process, and in some instances, for example, ovarian cancer, most of the cells are present as aggregates, making FACS CTC or CEC detection highly ineffective.

Approaches based on antibody-coated microbeads can use magnetic fields (Racila et al, 1998), column chromatography, centrifugation, filtration or FACS to achieve separation. Despite its great power for enrichment, there are also inherent limitations associated with all of the antibody-based cell separation methods. The most serious one is that cancer cells usually express putative tumor-specific antigens to variable degrees (Sabile et al., 1999); hence it is easy to lose a large and potentially non-random subset of tumor cells during the collection. Antibodies also tend to bind with significant non-specific affinity to damaged cells, leading to their co-purification with the cells of interest. Overall, such antibody-based cell separation methods have a higher than desired false-negative rate. Current antibody-initiated magnetic separation methods have detected CTC at much lower levels, i.e., 1-100 CTC per mL of blood from patients with breast and prostate cancer (Racila et al., 1998). There are approximately $5 \times 10^9$ red cells and $5 \times 10^6$ white nucleate cells present in one milliliter (ml) or gram of blood. Therefore, it is still a challenging task to detect the presence of thousands of cancer cells in one ml of blood (Gulati and Acaba, 1993).

Over the past 20 years, specialized complexes found on the surface of invasive tumor cells that facilitate their movement from the primary tumor to sites of metastasis have been characterized (Aoyama and Chen, 1990; Chen and Chen, 1987; Chen et al., 1994a; Chen et al., 1984; Chen et al., 1994b; Chen, 1996; Chen, 1989; Chen and Wang, 1999; Ghersi et al., 2002; Goldstein and Chen, 2000; Goldstein et al., 1997; Kelly et al., 1994; Monsky et at, 1994; Monsky et al., 1993; Mueller et al., 1999; Mueller and Chen, 1991; Mueller et al., 1992; Nakahara et al., 1996; Nakaliara et al., 1998; Nakahara et al., 1997; Pavlaki et al., 2002; Pineiro-Sanchez et al., 1997; Saga et al, 1988; Zucker et al, 2000; Zukowska-Grojec et al., 1998). These complexes, which we have denoted as "invadopodia", bind to and degrade multiple types of endothelial cell matrix (ECM) components. Invadopodia are not found on differentiated normal blood cells or on primary tumor cells, and they do not function effectively on dead or dying cells.

The applicant has recognized that an enrichment step based on invadopodia function would powerfully serve to separate viable metastatic tumor cells from the majority of cell types found in ascites, blood, and many other body fluids and would address the limitations of the other technologies described above. Apparatus and methods for conducting such an enrichment have been disclosed in U.S. Patent Application Publications 2002/0164825 published Nov. 7, 2002, 2003/0206901 published Nov. 6, 2003, 2005/0153342 published Jul. 14, 2005, 2005/0272103 published Dec. 8, 2005, all to Chen, and 2005/0244843 published Nov. 3, 2005, to Chen et al. All of the foregoing, and patents that issue therefrom, are incorporated herein in their entirety, by reference, for all purposes. The method employs a cell adhesion matrix ("CAM") especially adapted to retain cells having invadopodia. Since the method can achieve a one million fold enrichment of such cell types over their concentrations in whole blood, all manner of molecular biological measurements can be made on them that would be impossible absent the enrichment step.

It is to be noted that invadopodia are present on circulating endothelial progenitor cells (but absent in more than 99.999% of blood cells), and in fetal cells found in maternal blood of pregnant females. Circulating endothelial cells (CECs) are progenitors for the cells covering the internal surface of blood and lymphatic vessels that are involved in clinical complications including cancer, cardiovascular diseases, autoimmune diseases, and infectious diseases (Tarin, 2006; Beerepoot et al., 2004; Hill et al., 2003). CECs tend to be enriched along with CTCs in the methods described in the references cited above.

Thus, cell samples so enriched comprise various types of CTCs (based on tumor of origin and on relative pluripotency), and CECs as well. Recently, gene expression profiling (GEP) of immuno-magnetically isolated CECs based on an antibody against CD146 (Smirnov et al., 2006) showed a distinct set of CEC genes that were different from those of immuno-magnetically isolated CTCs described in a previous paper (Smirnov et al., 2005). However, it is not possible to resolve these cell types in a mixed population due to a lack of markers specific for these cell types, be they cancer cells or endothelial cell progenitors (van't Veer and Bernards, 2008; Sawyers, 2008). Enrichment makes any particular cell type highly accessible to genetic analysis, but leaves one uncertain about the cell to which the analysis should apply. What is needed is a means of resolving these cell types.

SUMMARY OF THE INVENTION

The invention relates to methods of finding a gene expression signature for a circulating tumor cell or other circulating cancer cell (particularly of epithelial lineage), or for a circulating endothelial cell, under conditions wherein the cells are selectively isolated from blood or other body fluid and highly enriched in concentration. In preferred embodiments, the signature is diagnostic of a particular type of cancer and is distinguishable from circulating endothelial cells.

In one embodiment, the invention enables the artisan to find a gene expression signature for a tumor cell by a method comprising providing (i) a reference tumor cell sample and (ii) a normal cell sample. The reference tumor cell sample is exposed to a cell-adhesion matrix ("CAM"), and a gene expression profile is determined for cells retained on the matrix ("CAM-avid"). In another step, a gene expression profile is determined for cells in a portion of the normal cell sample not exposed to a cell-adhesion matrix ("CAM_negative"). Next, the CAM-avid tumor cell gene expression profile is compared with the CAM-negative normal cell gene expression profile to identify a reference tumor cell gene signature comprising genes differentially expressed between said CAM-avid tumor cell gene expression profile and said CAM-negative normal cell gene expression profile.

In another aspect, the invention provides a reference tumor cell gene signature further refined by exposing another portion of the normal cell sample to the cell-adhesion matrix and determining a gene expression profile for normal cells retained on the matrix (i.e., a "CAM-avid" normal gene expression profile). The reference tumor gene signature is then compared to the CAM-avid normal cell gene expression profile to identify a first portion of the reference tumor cell gene signature attributable to expressed tumor cell genes and a second portion attributable to CAM-avid normal cell genes.

In one embodiment, the invention enables the artisan to find a gene expression signature for an endogenous tumor or cancer cell from a subject diagnosed as having that tumor or cancer. The method comprises: providing (i) a sample from the diagnosed subject and (ii) a normal cell sample. The sample from the diagnosed subject is exposed to a cell-adhesion matrix, and a gene expression profile is determined for cells retained on the matrix. In another step, a gene expression profile is determined for cells in a portion of the normal cell sample not exposed to a cell-adhesion matrix ("CAM-negative"). Additionally, a gene expression profile is determined for normal cells retained on a cell-adhesion matrix ("CAM-avid normal cells"). Next, the CAM-avid gene expression profile of the cells in the sample from the diagnosed subject is compared with the CAM-negative normal cell gene expression profile to identify an endogenous tumor or cancer cell gene signature comprising genes differentially expressed between said CAM-avid tumor or cancer cell gene expression profile and the CAM-negative normal cell gene expression profile to identify an initial endogenous tumor or cancer cell gene signature comprising genes differentially expressed between the CAM-avid endogenous tumor cell gene expression profile and the CAM-negative normal cell gene expression profile.

In a preferred embodiment, the invention provides a means of refining the initial endogenous tumor or cancer cell gene signature comprising: removing from the initial signature genes not known to upregulate in cells of epithelial lineage or in metastatic cells.

In an even more preferred embodiment, a further step is added: The artisan removes from the refined tumor gene signature genes wherein the differential expression between a gene of a CAM-avid tumor cell or a gene of a CAM-avid normal cell with respect to that gene in a CAM-negative normal cell gene is such that said differential expression indicates up-regulation of the gene in both the CAM-avid tumor and the CAM-avid normal cell, or down-regulation of the gene in both the CAM-avid tumor cell and the CAM-avid normal cell, to create an optimal tumor cell gene signature.

In one embodiment, the invention enables detection of an endogenous tumor or cancer cell in the blood or other body fluid of an undiagnosed subject by a method comprising comparing the undiagnosed subject's tumor cell gene signature for its similarity with a reference tumor cell gene signature or with a tumor cell signature of a diagnosed subject.

Some embodiments of the invention provide methods that depend upon the reference tumor cell selected or upon the type of tumor or cancer presented by the diagnosed subject, or upon the site in which the tumor originated or from which the tumor or cancer cells are collected. The reference tumor cell may be obtained, for example, from a cell line created from a neoplasm or tumor in a tissue, preferably a tissue of epithelial lineage. The tumor may be benign or malignant, primary or secondary to metastasis. Samples of cells for which the tumor cell signature of a diagnosed subject is sought may be collected by organ or tissue biopsy, or from blood, lymph or peritoneal fluid, or from any other site where cells of interest might be found. Samples of cells from undiagnosed subjects may also be collected from one of these sites. Preferably, cells from undiagnosed subjects are collected from blood, lymph, peritoneal fluid or other body fluid and are putative or actual "circulating tumor cells."

The methods that embody the invention provide tumor cell signatures that, in turn, enable methods of identifying, in an undiagnosed subject, a variety of tumor cell types, and distinguishing among them. The methods allow the artisan to distinguish between normal cells and benign, malignant, primary, metastatic, or metastasized cells. The methods also can distinguish between normal cells and tumor cells of epithelial lineage, including, without limitation, colorectal cancer, ovarian cancer, and breast cancer cells. The methods also allow the artisan to distinguish between benign vs. malignant cells, primary tumor vs. metastatic cells, and different tumor cells of epithelial lineage such as colorectal vs. breast cancer cells for example.

In one methodological embodiment of the invention, the method comprises a gene expression signature for metastatic tumor cells in ascites fluid obtained from ovarian cancer patients, which gene signature is effective in distinguishing samples of metastatic tumor cells in ascites from late stage primary ovarian tumor cells, and is also effective in distinguishing benign ovarian tumor cells from early stage malignant ovarian tumor cells.

In one embodiment, the method comprises, as a subset of the optimal gene signature, a gene signature effective for distinguishing circulating colon cancer cells from circulating normal cells, wherein the effective signature comprises ≥2, ≥3, ≥4, ≥5, or ≥6 of the constituents of Table I.

In one embodiment, the method comprises, as a subset of the optimal gene signature, a gene signature effective for distinguishing circulating breast cancer cells from circulating normal cells, wherein the effective signature comprises ≥2, ≥3, ≥4, ≥5, or ≥6 of the constituents of Table II.

In one embodiment, the method comprises, as a subset of the optimal gene signature, a gene signature effective for distinguishing circulating ovarian cancer cells from circulating normal cells, wherein the effective signature comprises ≥2, ≥3, ≥4, ≥5, or ≥6 of the constituents of FIG. 9A.

In one embodiment, the method comprises, as a subset of the optimal gene signature, a gene signature effective for distinguishing circulating ovarian cancer cells from circulating normal cells, wherein the effective signature comprises ≥7, ≥8, ≥9, ≥10, or ≥11 of the constituents of FIG. 9A.

In one embodiment, the method comprises, as a subset of the optimal gene signature, a gene signature effective for distinguishing circulating melanoma cells from circulating normal cells, wherein the effective signature comprises ≥2, ≥3, ≥4, ≥5, or ≥6 of the constituents of FIG. 1.

In one embodiment, the method distinguishes a circulating colon cancer cell from a different type of circulating cancer cell of epithelial origin comprising comparing an effective reference colon tumor cell gene signature or an effective colon tumor cell signature of a diagnosed subject to a gene expression signature of said different type of circulating cancer cell, wherein the effective colon tumor cell signature comprises ≥7, ≥8, ≥9, ≥10, or ≥11 of the constituents of Table I.

In one embodiment, the method distinguishes a circulating breast cancer cell from a different type of circulating cancer cell of epithelial origin comprising comparing an effective reference breast tumor cell gene signature or an effective breast tumor cell signature of a diagnosed subject to a gene expression signature of said different type of circulating cancer cell, wherein the effective breast tumor cell signature comprises ≥7, ≥8, ≥9, ≥10, or ≥11 of the constituents of Table II.

In one embodiment, the method distinguishes a circulating tumor cell from a circulating normal cell comprising comparing an effective reference tumor cell gene signature or an effective tumor cell signature of a diagnosed subject to a gene expression signature of said normal cell, wherein the effective tumor cell signature comprises at least one of the genes listed in Table 11 as upregulated in circulating tumor cells.

In one embodiment, the method detects a circulating tumor cell in a subject comprising:
a. providing a sample of blood from said subject;
b. enriching said sample;
c. finding a gene expression profile in said sample comprising at least one of the genes selected from the group consisting of KRT8, KRT16, KRT17, KRT18, KRT19 and KRT20.

In one embodiment, the method distinguishes a circulating tumor progenitor cell from a circulating normal normal progenitor cell comprising: comparing an effective reference tumor progenitor cell gene signature or an effective tumor progenitor cell signature of a diagnosed subject to a gene expression signature of said normal progenitor cell, wherein the effective tumor progenitor cell signature comprises at least one of the genes listed in Table 14 as upregulated in circulating tumor progenitor cells.

In one embodiment, the method the effective tumor progenitor cell signature comprises ≥7, ≥8, ≥9, ≥10, or ≥11 of the constituents listed in Table 14 as upregulated in circulating tumor progenitor cells.

In one embodiment, the method distinguishes a circulating colon cancer cell from a different type of circulating cancer cell of epithelial origin comprising: comparing an effective reference colorectal tumor cell gene signature or an effective tumor cell signature of a diagnosed subject to a gene expression signature of said different type of cancer cell, wherein the effective tumor cell signature comprises at least one of the genes listed in Table 15 as upregulated in circulating tumor progenitor cells.

In one embodiment, the method distinguishes a circulating endothelial cell from a circulating cancer cell of epithelial origin comprising: comparing an effective reference endothelial cell gene signature or an effective endothelial cell signature of a subject to an effective tumor cell gene signature or an effective tumor cell signature of a diagnosed subject, wherein the effective circulating endothelial cell signature comprises at least one of the genes listed in Table 16 as upregulated in circulating endothelial cells and not listed in Table 15 as upregulated in circulating tumor cells.

In one embodiment, the effective endothelial cell signature comprises ≥7, ≥8, ≥9, ≥10, or ≥11 of the constituents of Table 16.

In one embodiment, the invention provides method of internally controlling a comparison of gene expression signatures between or among circulating tumor cells of epithelial origin, circulating endothelial cells and other circulating cells, comprising: determining said expression signatures together with the expression of a gene selected from the group consisting of ITGA2, CD14 and ITGB.

BRIEF DESCRIPTION OF THE DRAWINGS

FIG. 2A. The 24-gene signature in tumor cells from six colon cancer patients cultured for over one day. FIG. 2B. The 24-gene signature in circulating breast tumor cells isolated from five patients with late stage breast cancer. FIG. 2C.

The 25-gene CTC signature for breast cancer that included components of putative tumor/epithelial lineage genes (CDH1, CEA, EMP2, GPR153, LENEP, MAP17, MUC1); proteases (CPM, seprase, ST14), protease inhibitors (SERPINA6), adhesion and chemokine receptors (BMPR1B, CMKLR1, ITGB1), and functional peptides (PLD1, S100A6, VIPR2). FIG. 3A. The 25-gene expression pattern in the breast tumor cells from seven breast cancer patients cultured for over one day. FIG. 3B. The breast signature in the circulating colon tumor cells isolated from five patients with late stage colon cancer. FIG. 3C.

FIG. 9A. Examination of the 37-gene expression pattern in the cells isolated by CAM from PTC of a stage IC serous adenocarcinoma of the ovary and other types of non-epithelial ovarian tumors. FIG. 9B. MTCA signature distinguished the tumors in ascites from primary tumors of late stages, from tumors of early stages, and from benign ovarian tumors. FIG. 9C.

FIG. 10A. Correlation between the MTCA score and tumor cells in the clinical specimens. FIG. 10B.

FIG. 12A. KRT marker genes (KRT8, KRT16 and KRT19) also showed minimal expression in the normal cell samples and significant expression in the breast and ovarian cancer cell samples. FIG. 12B.

FIG. 13A. Correlation of the CTC score and tumor cells in a blood sample based on patients' tumor type and stage, where the bars represent median values for each subgroup. FIG. 13B.

FIG. 15B.

FIG. 16 A-B. To validate the 17-candidate colorectal cancer CTC marker genes (DTR, PSCA, MUC3A, THRA, CD79B, NOTCH1, MUCDHL, NEUROG2, MDS028, KRT18, FOLH1, CD44, FCER2, SCF, CD7, SOX1 and TEKT3), the CTC score was used in testing the set of cellular samples that consists of 9 normal, 9 colorectal cancers and 20 breast cancers. FIG. 16B. A significant difference was observed in the mean±standard error CTC score between normal and cancer patients with colorectal and breast tumor types. FIG. 16C.

FIG. 18 shows the 29 genes known to be expressed cell of endothelial cell lineage that are preferable CEC and CTC markers. Colorgram depicts high (red) and low (blue) relative levels of gene expression. Red arrows indicate the internal control genes that exhibited no difference between normal and cancer cell samples. Endothelial genes that are upregulated in CECs and CTCs were identified by microarray analysis of RNA extracted from CAM bound cells of a training set that consists of 10 healthy donors and compared with the RNA extracted from CAM bound cells of 10 colon cancer patients. FIG. 18A. Selected genes were cross-examined using 7 normal samples and 9 breast cancer samples as well as 5 normal samples and 5 ovarian cancer samples. FIG. 18B.

FIG. 19 shows data validating the endothelial progenitor cell genes that are preferable CEC and CTC markers. The panels in FIG. 19A compare expression of the 29 endothelial progenitor cell genes and the 3-internal control genes as molecular markers for CECs and CTCs in samples from 9 normal, 9 colorectal cancer and 20 breast cancer samples. Columns represent catalogues of cell samples analyzed: circulating Normal (N) cells isolated with the one-step Vita-Cap™ assay from healthy donors with suffix M for Male and F for Female; CCa are circulating Colorectal Cancer (CCa) cells, and BCa being Breast Cancer (BCa) cells isolated by the one-step Vita-Cap™ assay with suffix I-IV being stages of the disease. Colorgram depicts high (red) and low (blue) relative levels of gene expression. Red arrows indicate the internal control genes that exhibited no difference between normal and cancer cell samples. The correlation between the CEC and CTC scores in a blood sample of healthy donors and cancer patients is graphed in FIG. 19B. The bars represent median values for each subgroup.

FIG. 20. Cell-based blood testing for detection of CECs and CTCs in a blood sample. Detection of CD31+/acLDL+/CAM- or CDH5+/acLDL+/CAM- cells in blood samples of a healthy donor and a patient with colon cancer as CECs (upper three panels, open arrows). Detection of CD31+/acLDL+/CAM+, CDH5+/acLDL+/CAM+, KRT8+/acLDL+/CAM+ or CD45-/acLDL+/CAM+ cells in blood samples of a patient with colon cancer as CTCs (lower four panels, single or double arrows). Bar=30 µm.

FIG. 21. Detection of CECs and CTCs by means of immuno-phenotyping of the cells isolated by magnetic beads coated with antibody to CD31 and CAM. Detection of CD31+/VWF+ and $CDH5^{low}/VWF+$ small spindle cells as CECs (upper two panels, open arrows). Detection of CD31+/VWF+, CDH5+/VWF+, KRT8+/VWF+ or CD45-/VWF+ large round cells as CTCs (four panels, single or double arrows). Bar=15 µm.

FIG. 22 Proliferation and differentiation of circulating progenitor cells isolated by CAM and CD31 immuno-magnetic cell separation methods from blood of cancer patients in vitro. FIG. 22A. Formation of blood vessel-like cellular network by the isolated circulating progenitor cells. Isolated cells were cultured on type I collagen gel for three days and live cells were photographed under phase contrast microscopy. Cells grew into interconnected network (double arrows) with canal-like structures in the center (single arrow). Bar=60 µm. FIG. 22B. Transmission electron micrograph of a cross-section of the cell shown in FIG. 22A. The canal-like structure (single arrow) is identified as a fold between two connecting cells (double arrows). Bar=0.1 µm. FIG. 22C. Colonies of spindle (endothelial) cells grown from the CD31-isolated cells in day 10. Bar=30 µm. FIG. 22D. Colonies of epithelioid cells grown from the CD31-isolated cells in day 10. Bar =30 µm. FIG. 22E. Colonies of epithelioid cells grown from the CD31-isolated cells in day 10 and doubly stained with pan-cytokeratin (CK) and VWF antibodies. In addition, Hoechst 33342 dye (Invitrogen, Carlsbad, CA) to locate the cell by labeling available nucleic acid (NA). Tumor cells (single and double arrows) are differentiated, shown as CK+, but lose expression of the endothelial marker (VWF), whereas spindle-shaped cells (open arrows) are CK-/VWF-. Bar=30 µm. FIG. 22F. Colonies of endothelial/epithelioid cells grown from the CD31-isolated cells in day 10 and stained with CD31 antibodies. Endothelial cells (open arrows) are CD31+/NA+. Bar=30 µm.

DEFINITIONS

Figure 1:
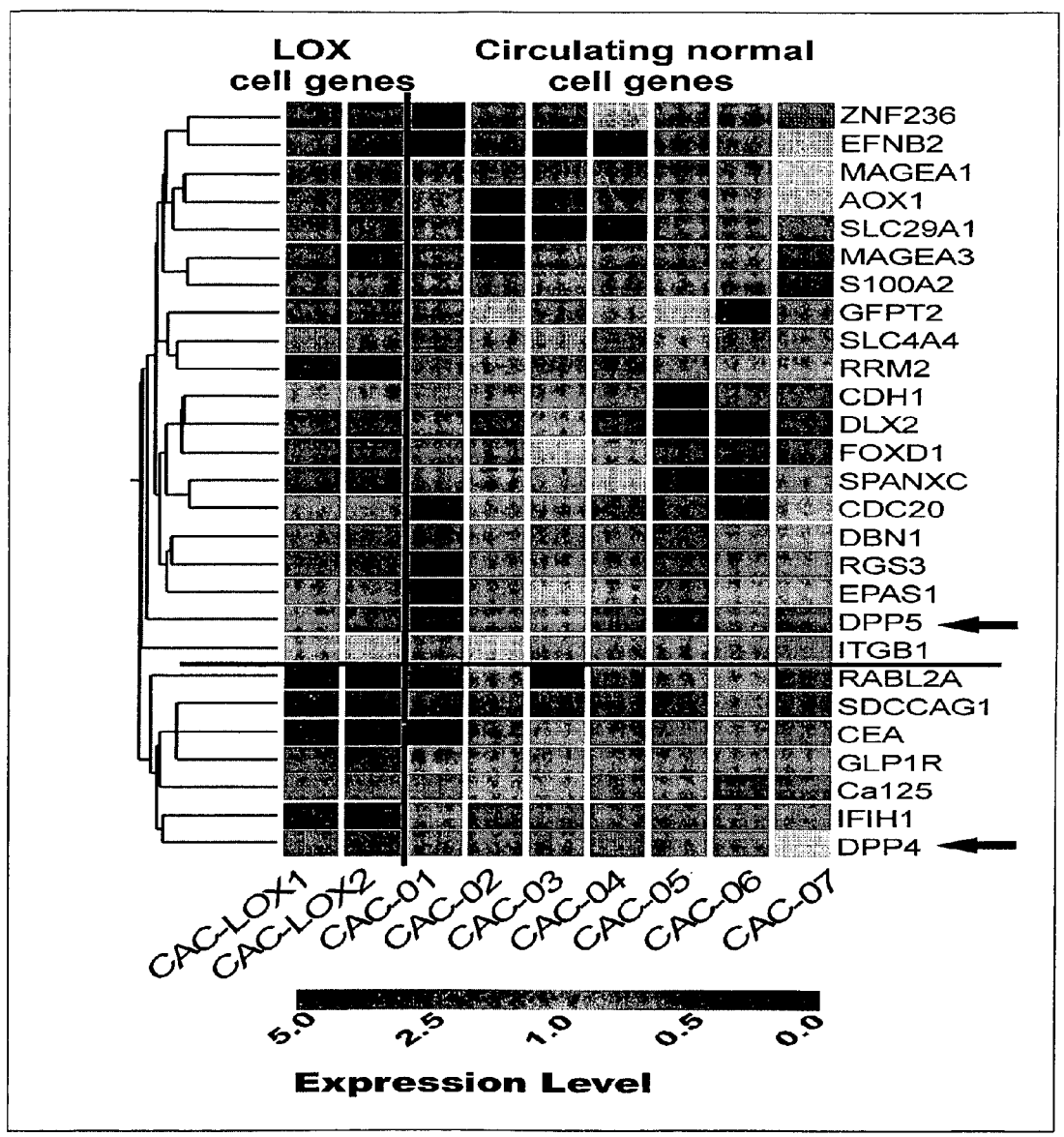
FIG. 1 shows the expression profile of 27 genes associated by hierarchical cluster analysis with LOX human malignant melanoma cells in blood compared with normal cells.

To facilitate the understanding of this invention a number of terms (set off in quotation marks in this Definitions section) are defined below. Terms defined herein (unless otherwise specified) have meanings as commonly understood by a person of ordinary skill in the areas relevant to the present invention. As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the invention, but their usage does not delimit the invention, except as outlined in the claims.

The phrase "chosen from A, B, and C" or "selected from the group consisting of A, B, and C" as used herein, means selecting one or more of A, B, C.

As used herein, absent an express indication to the contrary, the term "or" when used in the expression "A or B," where A and B refer to a composition, disease, product, etc., means one or the other, or both. As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, and c, a method of steps a, b, c, and x, as well as a method of steps x, a, b, and c. Furthermore, the term "comprising" when placed before the recitation of steps in a method does not (although it may) require sequential performance of the listed steps, unless the context clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weights, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (mRNA, etc.) or phenomenon (such as biological activity, biochemical activity, etc.) means that only the particularly named molecule or phenomenon is excluded.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively. By way of non-limiting example, where reference is made to the "upregulation" or "downregulation" of a gene, the phenomenon of its transcription into, for example, messenger RNA and/or its translation into protein is "altered."

The terms "increase," "elevate," "raise," and grammatical equivalents when used in reference to the level of a substance and/or phenomenon in a first sample relative to a second sample, mean that the quantity of the substance and/or phenomenon in the first sample is higher than in the second sample by any amount that is statistically significant using any art-accepted statistical method of analysis. In one embodiment, the increase may be determined subjectively, for example when a patient refers to his subjective perception of disease symptoms, such as pain, clarity of vision, etc. In another embodiment, the quantity of the substance and/or phenomenon in the first sample is at least 10% greater than the quantity of the same substance and/or phenomenon in a second sample. In another embodiment, the quantity of the substance and/or phenomenon in the first sample is at least 25% greater than the quantity of the same substance and/or phenomenon in a second sample. In yet another embodiment, the quantity of the substance and/or phenomenon in the first sample is at least 50% greater than the quantity of the same substance and/or phenomenon in a second sample. In a further embodiment, the quantity of the substance and/or phenomenon in the first sample is at least 75% greater than the quantity of the same substance and/or phenomenon in a second sample. In yet another embodiment, the quantity of the substance and/or phenomenon in the first sample is at least 90% greater than the quantity of the same substance and/or phenomenon in a second sample. Alternatively, a difference may be expressed as an "n-fold" difference.

The terms "reduce," "inhibit," "diminish," "suppress," "decrease," and grammatical equivalents when used in reference to the level of a substance and/or phenomenon in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to his subjective perception of disease symptoms, such as pain, clarity of vision, etc. In another embodiment, the quantity of substance and/or phenomenon in the first sample is at least 10% lower than the quantity of the same substance and/or phenomenon in a second sample. In another embodiment, the quantity of the substance and/or phenomenon in the first sample is at least 25% lower than the quantity of the same substance and/or phenomenon in a second sample. In yet another embodiment, the quantity of the substance and/or phenomenon in the first sample is at least 50% lower than the quantity of the same substance and/or phenomenon in a second sample. In a further embodiment, the quantity of the substance and/or phenomenon in the first sample is at least 75% lower than the quantity of the same substance and/or phenomenon in a second sample. In yet another embodiment, the quantity of the substance and/or phenomenon in the first sample is at least 90% lower than the quantity of the same substance and/or phenomenon in a second sample. Alternatively, a difference may be expressed as an "n-fold" difference.

A "sample" refers to a specimen taken from a normal subject, a diagnosed subject or an undiagnosed subject. A "diagnosed subject" relates to a subject known to have a cancer or tumor of interest. An "undiagnosed subject" may be healthy or may have a cancer. A "diagnosed subject sample" refers to a sample containing at least one cell suspended in a fluid such as blood, lymph or ascites, or saline, etc., which cell is a cancer cell of the type of cancer for which the diagnosed subject has been diagnosed. An "undiagnosed subject's sample" is the same except that, by definition, the cell therein can only be suspected of being a cancer cell. A "normal subject sample" does not contain a cancer cell. A sample is characterized herein not only by the subject's diagnosis but also by the site from which the sample is collected. Thus, in a subject diagnosed with ovarian cancer, for example, a sample comprising cells derived from a biopsy of the tumor, a sample comprising cells in ascites fluid drawn from the subject, and a sample obtained from a biopsy of a lymph node of the subject may be treated as different inasmuch as the cancer cell in each sample type may have its own gene expression signature.

An "enriched sample" refers to any one of the samples noted above after the bulk of cells in it have been removed by treating the sample on a cell-adhesion matrix or CAM as described herein.

A "gene expression signature" includes but is not limited to gene expression profiles as generally understood in the art. As used herein, however, a gene expression profile generally requires "editing" to become a gene expression "signature."

For example, a gene expression profile of circulating tumor cells in patients with late-stage colon cancer contained about 1200 genes differentially expressed in comparison to normal cells, whereas the gene signature ultimately derived therefrom comprised 24 genes only, because genes not known to upregulate in cells of epithelial lineage or in metastatic tumors were "edited out" as were some redundant upregulations and downregulations. A gene expression signature is referred to as an "initial signature" when less than all editing steps have been applied to the gene expression profile. In some contexts, reference is made to a "refined signature" simply to distinguish between two steps in the editing process. Thus, an "initial signature" may be refined by removing from it, for example, one or more genes not known to be upregulated in metastatic tumor cells, and further refined by removing one or more genes not known to be associated with cells of epithelial lineage. A signature that contains all the genes that survive editing is referred to herein as an "optimal signature," but less than all of the genes in an optimal signature may nevertheless constitute an "effective signature" herein. A gene that appears in a signature, whether by upregulation, downregulation, or otherwise, is said to be a "constituent" of the signature. For example, the constituent genes for an optimum signature for breast cancer cells are listed in Table II herein.

A number of terms herein relate to cancer. "Cancer" is intended herein to encompass all forms of abnormal or improperly regulated reproduction of cells in a subject. "Subject" and "patient" are used herein interchangeably, and a subject may be any mammal but is preferably a human. A "reference subject" herein refers to an individual who does not have cancer, and is used interchangeably with "healthy subject." The "reference subject" thereby provides a basis to which another cell (for example a cancer cell) can be compared.

The growth of cancer cells ("growth" herein referring generally to cell division but also to the growth in size of masses of cells) is characteristically uncontrolled or inadequately controlled, as is the death ("apoptosis") of such cells. Local accumulations of such cells result in a tumor. More broadly, and still denoting "tumors" herein, are accumulations ranging from a cluster of lymphocytes at a site of infection to vascularized overgrowths, both benign and malignant.

A "tumor" or "neoplasm" relates to any tissue that is growing abnormally because of uncontrolled or inadequately controlled, progressive multiplication of cells and that serves no discernible physiological function. The tumor or neoplasm may be benign if it has none of the properties of a cancer, that is, its growth is self-limited and its cells do not invade adjacent tissues or, by "metastasis," distant tissues. Tumors that grow sufficiently so as to encroach upon or invade adjacent tissues or that split off metastatic cells are said to be "malignant."

A "malignant" tumor (as opposed to a "benign" tumor) herein comprises cells that tend to migrate to nearby tissues, including cells that may travel through the circulatory system to invade or colonize tissues or organs at considerable remove from their site of origin in the "primary tumor," so-called herein. Metastatic cells are adapted to penetrate blood vessel wells to enter ("intravasate") and exit ("extravasate") blood vessels. Tumors capable of releasing such cells are also referred to herein as "metastatic." The term is used herein also to denote any cell in such a tumor that is capable of such travel, or that is en route, or that has established a foothold in a target tissue. For example, a metastatic breast cancer cell that has taken root in the lung is referred to herein as a "lung metastasis." Metastatic cells may be identified herein by their respective sites of origin and destination, such as "breast-to-bone metastatic." In the target tissue, a colony of metastatic cells can grow into a "secondary tumor," so called herein.

A "tumor cell" ("TC") relates to a cell derived from a tumor. The cell may be endogenous or exogenous. The cell may be split off from or harvested from a primary tumor or a secondary tumor; the cell may be a metastatic cell or a metastasized cell. The tumor of origin may be associated with any internal organ, including but not limited to colorectum, gastrointestinal tract and associated organs such as liver, pancreas and esophagus, ovary, uterus, prostate, lung, trachea kidney, bladder breast, brain and organs of the head and neck. A "circulating tumor cell" ("CTC") is a tumor cell actually circulating in the bloodstream, the lymphatic system or in other fluids such as peritoneal or cerebrospinal fluids.

A "reference tumor cell sample" relates to a normal cell sample to which cells from a tumor of interest have been added. The source of the tumor cells is preferably a cell line derived from the tumor-type that is of interest. The sample is said to be "spiked" with the tumor cells. Preferably, the sample is spiked only with the number of cells necessary to determine the cell's gene expression profile by whatever method is being employed to make the determination.

A cell of "epithelial lineage" herein refers to any pan-cytokeratin positive cell.

A "normal cell sample ("NC")" relates, without limitation, to a sample of blood, a blood fraction such as a leukocyte, epithelial cell, endothelial cell or hematopoietic progenitor cell fraction, another body fluid comprising cells, or a suspension of cells extracted from a tissue or organ such as breast, lung, intestine, ovary, etc., provided only that such sample is collected from a donor considered healthy by conventional standards Primary tumors are thought to derive from a benign or normal cell through a process referred to herein as "cancer progression." According to this view, the transformation of a normal cell to a cancer cell requires changes (usually many of them) in the cell's biochemistry. The changes are reflected clinically as the disease progresses through stages. Even if a tumor is "clonogenic" (as used herein, an accumulation of the direct descendants of a parent cell), the biochemistry of the accumulating cells changes in successive generations, both because the expression of the genes (controlled by so-called "epigenetic" systems) of these cells becomes unstable and because the genomes themselves change. In normal somatic cells, the genome (that is, all the genes of an individual) is stored in the chromosomes of each cell (setting aside the mitochondrial genome). The number of copies of any particular gene is largely invariant from cell to cell. By contrast, "genomic instability" is characteristic of cancer progression. A genome in a cancer cell can gain ("genomic gain") or lose ("genomic loss") genes, typically because an extra copy of an entire chromosome appears ("trisomy") or a region of a chromosome replicates itself ("genomic gain" or, in some cases, "genomic amplification") or drops out when the cell divides. Thus, the "copy number" of a gene or a set of genes, largely invariant among normal cells, is likely to change in cancer cells (referred to herein as a "genomic event"), which affects the total expression of the gene or gene set and the biological behavior ("phenotype") of descendent cells. Thus, in cancer cells, "gene activity" herein is determined not only by the multiple "layers" of epigenetic control systems and signals that call forth expression of the gene but by the number of times that gene appears in the genome. The term "epigenetic" herein refers to any process in an individual that, in operation, affects the expression of a gene or a set of genes in that individual, and stands in contrast to the "genetic" processes that govern the inheritance of genes in successive generations of cells or individuals.

It is thought that the emergence of metastatic cells entails its own distinct progression, referred to herein as "metastatic progression." The effect of disrupting a tumor on metastatic progression is unclear, but of interest because of "metastatic seeding," herein meaning a "surge" in metastasis that occurs, for example, when a tumor is surgically resected.

A number of terms herein relate to methods that enable the practitioner to examine many distinct genes at once. By these methods, sets of genes ("gene sets") have been identified wherein each set has biologically relevant and distinctive properties as a set. Devices (which may be referred to herein as "platforms") in which each gene in a significant part of an entire genome is isolated and arranged in an array of spots, each spot having its own "address," enable one to detect, quantitatively, many thousands of the genes in a cell. More precisely, these "microarrays" typically detect expressed genes (an "expressed" gene is one that is actively transmitting its unique biochemical signal to the cell in which the gene resides). Microarray data, inasmuch as they display the expression of many genes at once, permit the practitioner to view "gene expression profiles" in a cell and to compare those profiles cell-to-cell to perform so-called "comparative analyses of expression profiles." Such microarray-based "expression data" are capable of identifying genes that are "overexpressed" (or underexpressed) in, for example, a disease condition. An overexpressed gene may be referred to herein as having a high "expression score."

A gene expression profile may be "determined," without limitation, by means of DNA microarray analysis, PCR, quantitative RT-PCR, etc. These are referred to herein collectively as "nucleic-acid based: determinations or assays. Alternatively, methods as multiplexed immunofluorescence microscopy or flow cytometry may be used. These are referred to herein as "cell-based assays."

A "CAM-negative gene expression profile" refers to a profile acquired from cells in a sample that has not been exposed to a cell adhesion matrix ("CAM"). A "CAM-avid gene expression profile" refers to a profile acquired from cells in a sample that has been exposed to a CAM, which cells have adhered to the CAM. In some embodiments, the cells, or the RNAs therefrom, are "harvested" from the CAM before the gene expression profile is acquired. In some embodiments, the gene expression profile is acquired without first removing the RNAs from the CAM.

A gene in a cell from one sample is said to be "differentially expressed" with respect to the same gene in a cell from another sample if the expression level of the genes as between the two cells have, according to the GeneSpring 7.2 program, shows a fold-change ≥2 at a probability≤0.05 of that fold-change not being an actual difference, with the Multi-Testing Correction subroutine "on" to reduce false discover rate ("FDR"). The differential expression is an "up-regulation" if the fold-change is an increase (at least a doubling) and a "down-regulation" if the fold-change is a decrease (at least a 50% reduction).

Gene expression profiles may be "compared" by any of a variety of statistical analytic procedures including, without limitation, the use of GeneSpring 7.2 software (Silicon Genetics, Redwood City, Calif.) according to the manufacturer's instructions. One can establish a tumor cell score for each signature as a percentage of the genes in the signature that match the genes of a reference tumor cell signature or of a tumor cell signature of a subject known to bear said endogenous tumor cells A "gene expression signature" includes but is not limited to gene expression profiles as generally understood in the art. As used herein, however, a gene expression profile generally requires "editing" to become a gene expression "signature." For example, a gene expression profile of circulating tumor cells in patients with late-stage colon cancer contained about 1200 genes differentially expressed in comparison to normal cells, whereas the gene signature ultimately derived therefrom comprised 24 genes only, because genes not known to upregulate in cells of epithelial lineage or in metastatic tumors were "edited out" as were some redundant upregulations and downregulations. A gene expression signature is referred to as an "initial signature" when less than all editing steps have been applied to the gene expression profile. In some contexts, reference is made to a "refined signature" simply to distinguish between two steps in the editing process. Thus, an "initial signature" may be refined by removing from it, for example, one or more genes not known to be upregulated in metastatic tumor cells, and further refined by removing one or more genes not known to be associated with cells of epithelial lineage. A signature that contains all the genes that survive editing is referred to herein as an "optimal signature," but less than all of the genes in an optimal signature may nevertheless constitute an "effective signature" herein. A gene that appears in a signature, whether by upregulation, downregulation, or otherwise, is said to be a "constituent" of the signature.

The aforementioned methods for examining gene sets employ a number of well-known methods in molecular biology, to which references are made herein. A gene is a heritable chemical code resident in, for example, a cell, virus, or bacteriophage that an organism reads (decodes, decrypts, transcribes) as a template for ordering the structures of biomolecules that an organism synthesizes to impart regulated function to the organism. Chemically, a gene is a heteropolymer comprised of subunits ("nucleotides") arranged in a specific sequence. In cells, such heteropolymers are deoxynucleic acids ("DNA") or ribonucleic acids ("RNA"). DNA forms long strands. Characteristically, these strands occur in pairs. The first member of a pair is not identical in nucleotide sequence to the second strand, but complementary. The tendency of a first strand to bind in this way to a complementary second strand (the two strands are said to "anneal" or "hybridize"), together with the tendency of individual nucleotides to line up against a single strand in a complementarily ordered manner accounts for the replication of DNA.

Experimentally, nucleotide sequences selected for their complementarity can be made to anneal to a strand of DNA containing one or more genes. A single such sequence can be employed to identify the presence of a particular gene by attaching itself to the gene. This so-called "probe" sequence is adapted to carry with it a "marker" that the investigator can readily detect as evidence that the probe struck a target. As used herein, the term "marker" relates to any surrogate the artisan may use to "observe" an event or condition that is difficult or impossible to detect directly. In some contexts herein, the marker is said to "target" the condition or event. In other contexts, the condition or event is referred to as the target for the marker. Sequences used as probes may be quite small (e.g., "oligonucleotides" of <20 nucleotides) or quite large (e.g., a sequence of 100,000 nucleotides in DNA from a "bacterial artificial chromosome" or "BAC"). A BAC is a bacterial chromosome (or a portion thereof) with a "foreign" (typically, human) DNA fragment inserted in it. BACs are employed in a technique referred to herein as "fluorescence in situ hybridization" or "FISH." A BAC or a portion of a BAC is constructed that has (1) a sequence complementary to a region of interest on a chromosome and (2) a marker whose presence is discernible by fluorescence. The chromosomes of a cell or a tissue are isolated (on a glass slide, for example) and treated with the BAC construct. Excess construct is washed away and the chromosomes examined microscopically to find chromosomes or, more particularly, identifiable regions of chromosomes that fluoresce.

Alternatively, such sequences can be delivered in pairs selected to hybridize with two specific sequences that bracket a gene sequence. A complementary strand of DNA then forms between the "primer pair." In one well-known method, the "polymerase chain reaction" or "PCR," the formation of complementary strands can be made to occur repeatedly in an exponential amplification. A specific nucleotide sequence so amplified is referred to herein as the "amplicon" of that sequence. "Quantitative PCR" or "qPCR" herein refers to a version of the method that allows the artisan not only to detect the presence of a specific nucleic acid sequence but also to quantify how many copies of the sequence are present in a sample, at least relative to a control. As used herein, "qRT-PCR" may refer to "quantitative real-time PCR," used interchangeably with "qPCR" as a technique for quantifying the amount of a specific DNA sequence in a sample. However, if the context so admits, the same abbreviation may refer to "quantitative reverse transcriptase PCR," a method for determining the amount of messenger RNA present in a sample. Since the presence of a particular messenger RNA in a cell indicates that a specific gene is currently active (being expressed) in the cell, this quantitative technique finds use, for example, in gauging the level of expression of a gene.

Collectively, the genes of an organism constitute its genome. The term "genomic DNA" may refer herein to the entirety of an organism's DNA or to the entirety of the nucleotides comprising a single gene in an organism. A gene typically contains sequences of nucleotides devoted to coding ("exons"), and non-coding sequences that contribute in one way or another to the decoding process ("introns").

The term "gene" refers to a nucleic acid (e.g., DNA) comprising covalently linked nucleotide monomers arranged in a particular sequence that comprises a coding sequence necessary for the production of a polypeptide or precursor or RNA (e.g., tRNA, siRNA, rRNA, etc.). The polypeptide can be encoded by a full-length coding sequence or by any portion of the coding sequence so long as the desired activities or functional properties (e.g., enzymatic activity, ligand binding, signal transduction, etc.) of the full-length or fragment are retained. The term also encompasses the coding region together with the sequences located adjacent to the coding region on both the 5' and 3' ends, such that the gene corresponds to the length of the full-length mRNA (also referred to as "pre-mRNA," "nuclear RNA," or "primary transcript RNA") transcribed from it. The sequences that are located 5' of the coding region and are present on the mRNA are referred to as 5' untranslated sequences. The sequences that are located 3' or downstream of the coding region and that are present on the mRNA are referred to as 3' untranslated sequences. The term "gene" encompasses both cDNA (the coding region(s) only) and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

Encoding in DNA (and messenger RNA) is accomplished by 3-membered nucleotide sequences called "codons." Each codon encrypts an amino acid, and the sequence of codons encrypts the sequence of amino acids that identifies a particular protein. The code for a given gene is embedded in a (usually) much longer nucleotide sequence and is distinguishable to the cell's decoding system from the longer sequence by a "start codon" and a "stop" codon. The decoding system reads the sequence framed by these two codons (the so-called "open reading frame"). The readable code is transcribed into messenger RNA which itself comprises sites that ensure coherent translation of the code from nucleic acid to protein. In particular, the open reading frame is delimited by a so-called "translation initiation" codon and "translation termination" codon.

The term "recombinant DNA" refers to a DNA molecule that is comprised of segments of DNA joined together by means of molecular biology techniques. Similarly, the term "recombinant protein" refers to a protein molecule that is expressed from recombinant DNA.

Where an amino acid sequence is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Rather the terms "amino acid sequence" and "protein" encompass partial sequences, and modified sequences.

The term "wild type" refers to a gene or gene product that has the characteristics of that gene or gene product when isolated from a naturally occurring source. A wild type gene is the variant most frequently observed in a population and is thus arbitrarily designed the "normal" or "wild-type" form of the gene In contrast, the terms "modified," "mutant," and "variant" (when the context so admits) refer to a gene or gene product that displays modifications in sequence and or functional properties (i.e., altered characteristics) when compared to the wild-type gene or gene product. In some embodiments, the modification comprises at least one nucleotide insertion, deletion, or substitution.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to reduction in binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" when used in reference to a first and a second polypeptide means that the first polypeptide with an activity binds to the same substrate as does the second polypeptide with an activity. In one embodiment, the second polypeptide is a variant of the first polypeptide (e.g., encoded by a different allele) or a related (e.g., encoded by a homolog) or dissimilar (e.g., encoded by a second gene having no apparent relationship to the first gene) polypeptide. The efficiency (e.g., kinetics or thermodynamics) of binding by the first polypeptide may be the same as or greater than or less than the efficiency of substrate binding by the second polypeptide. For example, the equilibrium binding constant ($K_D$) for binding to the substrate may be different for the two polypeptides.

As used herein, the term "hybridization" refers to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41$ (% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with 85-100% identity, preferably 70-100% identity). With medium stringency conditions, nucleic acid base pairing will occur between nucleic acids with an intermediate frequency of complementary base sequences (e.g., hybridization under "medium stringency" conditions may occur between homologs with 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 100 to about 1000 nucleotides in length is employed.

"Medium stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 100 to about 1000 nucleotides in length is employed.

"Low stringency conditions" comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, *Adv. Appl. Math.*, 2: 482, 1981) by the homology alignment algorithm of Needleman and Wunsch (Needleman and Wunsch, *J. Mol. Biol.* 48:443, 1970), by the search for similarity method of Pearson and Lipman (Pearson and Lipman, *Proc. Natl. Acad. Sci., U.S.A.,* 85:2444, 1988), by computerized implementations of these algorithms (GAP, BESTFIT, FASTA, and TFASTA in the Wisconsin Genetics Software Package Release 7.0, Genetics Computer Group, Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having acidic side chains is glutamic acid and aspartic acid; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Amplification" is used herein in two different ways. A given gene typically appears in a genome once, on one chromosome. Since chromosomes in somatic cells of eukaryotes are in general paired, two copies or alleles of each gene are found. In some conditions, such as cancer, replication of chromosome pairs during cell division is disturbed so that multiple copies of a gene or chromosome accrue over successive generations. The phenomenon is referred to generally (and herein) as "amplification."

In the context of molecular biological experimentation, the term is used differently. Experimentally, "amplification" is used in relation to a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under the conditions in which they are used, will process only specific sequences of nucleic acids in a heterogeneous mixture of nucleic acids. In particular, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of Mullis (U.S. Pat. Nos. 4,683,195, 4,683,202, and 4,965,188, hereby incorporated by reference), that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the terms "restriction endonucleases" and "restriction enzymes" refer to bacterial enzymes, each of which cut double-stranded DNA at or near a specific nucleotide sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding gene includes, by way of example, such nucleic acid in cells ordinarily expressing gene where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

Besides nucleic acids, cells may be "isolated" from one another. In this context, isolation need not be physical. That is, two cells of different types resting side-by-side physically may be "isolated" from one another because each is distinguishable by a distinctive "marker." The marker may be anything uniquely associated with the cell-type of interest and instrumentally observable.

The terms "fragment" and "portion" when used in reference to a nucleotide sequence (as in "a portion of a given nucleotide sequence") refers to partial segments of that sequence. The fragments may range in size from four nucleotides to the entire nucleotide sequence minus one nucleotide (10 nucleotides, 20, 30, 40, 50, 100, 200, etc.).

Similarly, the terms "fragment" and "portion" when used in reference to a polypeptide sequence refers to partial segments of that sequence. In some embodiments, the portion has an amino-terminal and/or carboxy-terminal deletion as compared to the native protein, but where the remaining amino acid sequence is identical to the corresponding positions in the amino acid sequence deduced from a full-length cDNA sequence. Fragments are preferably at least 4 amino acids long, more preferably at least 50 amino acids long, and most preferably at least 50 amino acids long or longer (the entire amino acid sequence minus on amino acid). In particularly preferred embodiments, the portion comprises the amino acid residues required for intermolecular binding of the compositions of the present invention with its various ligands and/or substrates.

As used herein the term "portion" when in reference to a protein (as in "a portion of a given protein") refers to fragments of that protein. The fragments may range in size from four consecutive amino acid residues to the entire amino acid sequence minus one amino acid As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA As used herein, the term "purified" refers to molecules (polynucleotides or polypeptides) that are separated from other components with which they are naturally associated. "To purify" refers to a reduction (preferably by at least 10%, more preferably by at least 50%, and most preferably by at least 90%) of one or more contaminants from a sample.

The term "recombinant DNA molecule" as used herein refers to a DNA molecule that is comprised of segments of DNA joined together by means of molecular biological techniques. Similarly, the term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences, that is the native protein contains only those amino acids found in the protein as it occurs in nature. A native protein may be produced by recombinant means or may be isolated from a naturally occurring source.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual*, Cold Spring Harbor Press, N.Y., pp 9.31-9.58, 1989).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp 7.39-7.52, 1989).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies The terms "antigenic determinant" and "epitope" as used herein refer to that portion of an antigen that makes contact with a particular antibody and/or T cell receptor. When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

As used herein, the term "transgenic" refers to a cell or organism whose genome has been heritably altered by genetically engineering into the genome a gene ("transgene") not normally part of it or removing from it a gene ordinarily present (a "knockout" gene). The "transgene" or "foreign gene" may be placed into an organism by introducing it into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term host cell refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell in the sense that the foreign DNA will be passed on to daughter cells. The term encompasses transfections of foreign DNA into the cytoplasm only. In general, however, the foreign DNA reaches the nucleus of the transfected cell and persists there for several days. During this time the foreign DNA is subject to the regulatory controls that govern the expression of endogenous genes in the chromosomes. The term "transient transfectant" refers to cells that have taken up foreign DNA but have failed to integrate this DNA. The term "transient transfection" encompasses transfection of foreign DNA into the cytoplasm only.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of is modified to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding a particular protein or fragments thereof may be employed as hybridization probes. The polynucleotide sequences are typically employed in an aqueous solution containing salts (e.g., NaCl), detergents (e.g., SDS), and other components (e.g., Denhardt's solution, dry milk, salmon sperm DNA, etc.).

The terms "N-terminus" "$NH_2$-terminus" and "amino-terminus" refer to the amino acid residue corresponding to the methionine encoded by the start codon (e.g., position or residue 1). In contrast the terms "C-terminus" "COOH-terminus" and "carboxy terminus" refer to the amino acid residue encoded by the final codon (e.g., last or final residue prior to the stop codon).

The term "antibody" refers to polyclonal and monoclonal antibodies. Polyclonal antibodies which are formed in the animal as the result of an immunological reaction against a protein of interest or a fragment thereof, can then be readily isolated from the blood using well-known methods and purified by column chromatography, for example. Monoclonal antibodies can also be prepared using known methods (See, Winter and Milstein, Nature, 349, 293-299, 1991). As used herein, the term "antibody" encompasses recombinantly prepared, and modified antibodies and antigen-binding fragments thereof, such as chimeric antibodies, humanized antibodies, multifunctional antibodies, bispecific or oligo-specific antibodies, single-stranded antibodies and F(ab) or F(ab)$_2$ fragments. The term "reactive" when used in reference to an antibody indicates that the antibody is capable of binding an antigen of interest.

The terms "auto-antibody" or "auto-antibodies" refer to any immunoglobulin that binds specifically to an antigen that is native to the host organism that produced the antibody (i.e., the antigen is not synthetic and/or has not been artificially supplied to the host organism). However, the term encompasses antibodies originally produced in response to the administration or presence of a foreign and/or synthetic substance in the host, but also cross-react with "self" antigens. Exemplary auto-antibodies include, without limitation, anti-cholesterol ester transfer protein (CETP) antibody, anti-major histocompatibility complex class II antibody, anti-cytokine antibody, and anti amyloid-β-peptide antibody. The presence of auto-antibodies is termed "autoimmunity."

The term "B cell epitope" as used herein refers to an antigenic determinant (protein or carbohydrate) to which a single antibody molecule binds. B cell epitopes may comprise linear epitopes (amino acids adjacent to each other in the primary sequence) or conformational epitopes (moieties distant from each other in the primary sequence, but which are brought in proximity to one another during folding of the antigen) of at least four amino acid residues.

The term "T cell epitope" as used herein refers to an antigenic determinant presented by a MHC class I or class II molecule for binding to a single T cell receptor. T cell epitopes are linear epitopes comprising at least seven amino acid residues. In some embodiments of the present invention, the term T cell epitope comprises a T helper cell epitope which is an antigen fragment presented by an MHC class II molecule for binding to T cell receptor on the surface of a helper T cell (e.g., generally CD4$^+$).

The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.

The terms "antigen," "immunogen," "antigenic," "immunogenic," "antigenically active," and "immunologically active" refer to any substance that is capable of inducing a specific humoral and/or cell-mediated immune response. An immunogen generally contains at least one epitope. Immunogens are exemplified by, but not restricted to molecules which contain a peptide, polysaccharide, nucleic acid sequence, and/or lipid. Complexes of peptides with lipids, polysaccharides, or with nucleic acid sequences are also contemplated, including (without limitation) glycopeptide, lipopeptide, glycolipid, etc. These complexes are particularly useful immunogens where smaller molecules with few epitopes do not stimulate a satisfactory immune response by themselves.

A peptide sequence and nucleotide sequence may be "endogenous" or "heterologous" (i.e., "foreign"). The term "endogenous" refers to a sequence which is naturally found in the cell or virus into which it is introduced so long as it does not contain some modification relative to the naturally-occurring sequence. The term "heterologous" refers to a sequence which is not endogenous to the cell or virus into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell or virus into which it is introduced and which contains some modification relative to the naturally-occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc. In preferred embodiments, the terms "heterologous antigen" and "heterologous sequence" refer to a non-hepadna virus antigen or amino acid sequence including but not limited to microbial antigens, mammalian antigens and allergen antigens.

The terms "peptide," "peptide sequence," "amino acid sequence," "polypeptide," and "polypeptide sequence" are used interchangeably herein to refer to at least two amino acids or amino acid analogs which are covalently linked by a peptide bond or an analog of a peptide bond. The term peptide includes oligomers and polymers of amino acids or amino acid analogs. The term peptide also includes molecules which are commonly referred to as peptides, which generally contain from about two (2) to about twenty (20) amino acids. The term peptide also includes molecules which are commonly referred to as polypeptides, which generally contain from about twenty (20) to about fifty amino acids (50). The term peptide also includes molecules which are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide which is produced by artificial means in vitro The terms "oligosaccharide" and "OS" antigen refer to a carbohydrate comprising up to ten component sugars, either O or N linked to the next sugar. Likewise, the terms "polysaccharide" and "PS" antigen refer to polymers of more than ten monosaccharide residues linked glycosidically in branched or unbranched chains As used herein, the term "mammalian sequence" refers to synthetic, recombinant or purified sequences (preferably sequence fragments comprising at least one B cell epitope) of a mammal. Exemplary mammalian sequences include cytokine sequence, MHC class I heavy chain sequences, MHC class II alpha and beta chain sequences, and amyloid β-peptide sequences.

The terms "mammals" and "mammalian" refer animals of the class mammalia which nourish their young by fluid secreted from mammary glands of the mother, including human beings. The class "mammalian" includes placental animals, marsupial animals, and monotrematal animals. An exemplary "mammal" may be a rodent, primate (including simian and human) ovine, bovine, ruminant, lagomorph, porcine, caprine, equine, canine, feline, ave, etc. Preferred non-human animals are selected from the order Rodentia.

Preferred embodiments of the present invention are primarily directed to vertebrate (backbone or notochord) members of the animal kingdom.

The terms "patient" and "subject" refer to a mammal that may be treated using the methods of the present invention.

The term "control" refers to subjects or samples which provide a basis for comparison for experimental subjects or samples. For instance, the use of control subjects or samples permits determinations to be made regarding the efficacy of experimental procedures. For example, a "control gene" is equally likely to appear in two samples that are otherwise genically distinct, so that any variation in the control gene in the two samples indicates an error.

As used herein, the term "immune response" refers to the reactivity of an organism's immune system in response to an antigen. In vertebrates, this may involve antibody production, induction of cell-mediated immunity, and/or complement activation (e.g., phenomena associated with the vertebrate immune system's prevention and resolution of infection by microorganisms). In preferred embodiments, the term immune response encompasses but is not limited to one or more of a "lymphocyte proliferative response," a "cytokine response," and an "antibody response."

The term "antibody response" refers to the production of antibodies (e.g., IgM, IgA, IgG) which bind to an antigen of interest, this response is measured for instance by assaying sera by antigen ELISA.

The term "adjuvant" as used herein refers to any compound which, when injected together with an antigen, non-specifically enhances the immune response to that antigen. Exemplary adjuvants include but are not limited to incomplete Freunds adjuvant (IFA), aluminum-based adjuvants (e.g., AIOH, AlPO4, etc), and Montanide ISA 720.

The terms "diluent" and "diluting agent" as used herein refer to agents used to diminish the strength of an admixture. Exemplary diluents include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

The term "derived" when in reference to a peptide derived from a source (such as a microbe, cell, etc.) as used herein is intended to refer to a peptide which has been obtained (e.g., isolated, purified, etc.) from the source. Alternatively, or in addition, the peptide may be genetically engineered and/or chemically synthesized.

The terms "operably linked," "in operable combination," and "in operable order" as used herein refer to the linkage of nucleic acid sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. Similarly, operably linking a nucleic acid sequence encoding a protein of interest means linking the nucleic acid sequence to regulatory and other sequences in a manner such that the protein of interest is expressed. The term also refers to the linkage of amino acid sequences in such a manner so that a functional protein is produced.

The terms "C-terminal portion," "COOH-terminal portion," "carboxy terminal portion," "C-terminal domain," "COOH-terminal domain," and "carboxy terminal domain," when used in reference to an amino acid sequence of interest refer to the amino acid sequence (and portions thereof that is located from approximately the middle of the amino acid sequence of interest to the C-terminal-most amino acid residue of the sequence of interest. The terms "specific binding," "binding specificity," and grammatical equivalents thereof when made in reference to the binding of a first molecule (such as a polypeptide, glycoprotein, nucleic acid sequence, etc.) to a second molecule (such as a polypeptide, glycoprotein, nucleic acid sequence, etc.) refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule. "Specific binding" of a first molecule with a second molecule also means that the interaction between the first molecule and the second molecule is dependent upon the presence of a particular structure on or within the first molecule; in other words the second molecule is recognizing and binding to a specific structure on or within the first molecule rather than to nucleic acids or to molecules in general. For example, if a second molecule is specific for structure "A" that is on or within a first molecule, the presence of a third nucleic acid sequence containing structure A will reduce the amount of the second molecule which is bound to the first molecule.

The term "has the biological activity of a specifically named protein" when made in reference to the biological activity of a variant of the specifically named protein refers, for example, to a quantity of binding of an antibody that is specific for the specifically named protein to the variant which is preferably greater than 50% (preferably from 50% to 500%, more preferably from 50% to 200%, most preferably from 50% to 100%), as compared to the quantity of binding of the same antibody to the specifically named protein.

Reference herein to any specifically named nucleotide sequence includes within its scope fragments, homologs, and sequences that hybridize under stringent condition to the specifically named nucleotide sequence. The term "homolog" of a specifically named nucleotide sequence refers to an oligonucleotide sequence which exhibits greater than or equal to 50% identity to the sequence of interest. Alternatively, or in addition, a homolog of any specifically named nucleotide sequence is defined as an oligonucleotide sequence which has at least 95% identity with the sequence of the nucleotide sequence in issue. In another embodiment, the sequence of the homolog has at least 90% identity, and preferably at least 85% identity with the sequence of the nucleotide sequence in issue.

Exons, introns, genes and entire gene-sets are characteristically locatable with respect to one another. That is, they have generally invariant "genomic loci" or "genomic positions." Genes distributed across one or several chromosomes can be mapped to specific locations on specific chromosomes. The field of "cytogenetics" addresses several aspects of gene mapping. First, optical microscopy reveals features of chromosomes that are useful as addresses for genes. In humans, chromosomes are morphologically distinguishable from one another and each (except for the Y-chromosome) has two distinct arms separated by a "centromere." Each arm has distinctive "bands" occupied by specific genes. Disease-related changes in chromosome number, and changes in banding form the basis for diagnosing a number of diseases. "Microdissection" of chromosomes and DNA analysis of the microdissected fragments have connected specific DNA sequences to specific locations on chromosomes. In cancer, a region of a chromosome may duplicate or amplify itself or drop out entirely. FISH, mentioned above, and "comparative genomic hybridization" ("CGH") have extended the reach of cytogenetic analysis to the extent of measuring genome alterations within and between individuals. CGH, for example, in which chromosomes from a normal cell are hybridized with a corresponding preparation from a cancer cell provides a means of directly determining cancer-related differences in copy number of chromosomal regions.

A number of terms used herein relate to antibodies. Antibodies are globular proteins produced by cells of the immune system ("immunoglobulins"). A population of antibodies that all arose from one cell and its progeny is a "monoclonal antibody." Others are "polyclonal." Antibodies bind antigens. Antigens are compositions to which an immune system has adapted by acquiring the ability to synthesize an immunoglobulin that specifically binds to a given antigen in the sense that a "bound" antigen is no longer thermodynamically free in solution. Fragments of an antibody are capable of binding a (specific) antigen, and such fragments (e.g., Fv, Fab, Fab' and $F(ab')_2$) may be used in embodiments of the invention. Monoclonal antibodies are preferably produced in cells maintained and reproduced in vitro. Such cells are preferably hybridomas. Methods well known in the art are used to create hybridoma cells, a characteristic of which is to secrete a specific monoclonal antibody in quantity. Briefly, to create a hybridoma cell line (a "cell line" herein is any collection of cells proliferated in vitro), a mammal is immunized with the antigenic composition bound to a carrier. The carrier (e.g., protein, peptide, such as serum albumin or gamma globulin obtained from the mammal) is not recognized as a foreign molecule to the mammal. Preferably, however, the carrier is an antibody produced by the mammal. The carrier antibody can bind the hapten, but not with any specificity. Since the mammal produced the carrier antibody, the mammal will not necessarily recognize the carrier antibody as foreign and will likely produce antibodies having binding specificity only for the hapten. Splenocytes (typically) of the mammal are fused with immortalized cells to produce hybridomas and the hybridoma which produces a monoclonal antibody or antigen binding fragment thereof having the particular binding specificity for the hapten is selected. "Immortalized" cells herein are cells that reproduce indefinitely when cultured in vitro.

Monoclonal antibodies may be useful therapeutically in so-called "immunotherapy." Monoclonal antibodies typically are products of non-human cells and may therefore cause untoward immune responses when injected into human subjects. Methods of "humanizing" such antibodies are well-known in the art, however. In one method, the cells responsible for producing the antibody are genetically engineered to make and secrete a so-called "chimeric" protein. A usually small portion of such a protein is a fragment of the monoclonal antibody and the rest is a human immunoglobulin. Chimeric proteins are a particular kind of "fusion protein." As used herein, any protein expressed by a gene (typically, a recombinant gene) comprising the genetic code for two or more generally independent proteins is a fusion protein.

Monoclonal antibodies also find use herein to detect particular cells, subcellular bodies, etc. by "immunostaining." The antibody delivers a stainable (or otherwise detectable) element to its antigenic determinant. Thus, monoclonal antibodies are useful diagnostically for a countless number of conditions, not the least of which is their use in determining genomic changes in cancer cells.

The term "agent" is used herein in its broadest sense to refer to a composition of matter, a process or procedure, a device or apparatus employed to exert a particular effect. By way of non-limiting example, a surgical instrument may be employed by a practitioner as an "excising" agent to remove tissue from a subject; a chemical may be used as a pharmaceutical agent to remove, damage or neutralize the function of a tissue, etc. Such pharmaceutical agents are said to be "anti-cellular." Cells may be removed by an agent that promotes apoptosis. A variety of toxic agents, including other cells (e.g., cytotoxic T-cell lymphocytes) and their secretions, and a plethora of chemical species, can damage cells.

The term "by-stander", as used herein, refers to a process or event initiated or affected by another, causative event or process The term "class prediction", as used herein, refers to a method of making predictions about an individual outcome for an individual of a particular class based on historical outcomes in similarly classified individuals.

The term "knockdown", as used herein, refers to a method of selectively preventing the expression of a gene in an individual.

The term "oncogene", as used herein, refers to any gene that regulates a process affecting the suppression of abnormal proliferative events.

The term "integrative genomic analysis", as used herein, refers to any study of an individual's genome by analyzing data from at least two distinct methods of genomic analysis in combination.

The term "single nucleotide polymorphism" or "SNP", as used herein, refers to a DNA sequence variation occurring when a single nucleotide in the genome (or other shared sequence) differs between members of a species or between paired chromosomes in an individual. Single nucleotide polymorphisms may fall within coding sequences of genes, non-coding regions of genes, or in the intergenic regions between genes. Single nucleotide polymorphisms within a coding sequence will not necessarily change the amino acid sequence of the protein that is produced, due to degeneracy of the genetic code. A Single nucleotide polymorphism in which both forms lead to the same polypeptide sequence is termed synonymous (sometimes called a silent mutation)—if a different polypeptide sequence is produced they are non-synonymous. Single nucleotide polymorphisms that are not in protein-coding regions may still have consequences for gene splicing, transcription factor binding, or the sequence of non-coding RNA.

The term "algorithm", as used herein, refers to a step-by-step problem-solving procedure, especially an established, recursive computational procedure for solving a problem in a finite number of steps. The bioinformatics strategy referred to as "Analysis of CNAs by Expression data" (ACE) is one example of an algorithm that detects recurrent DNA copy number alterations (CNAs) that affect regional gene expression.

The term "tissue array" or "tissue microarray", as used herein, refers to high throughput platforms for the rapid analysis of protein, RNA, or DNA molecules as does the term "cell array" or "cell panel." These arrays or panels can be used to validate the clinical relevance of potential biological targets in the development of diagnostics, therapeutics and to study new disease markers and genes. Tissue arrays and cell arrays are suitable for genomics-based diagnostic and drug target discovery.

The term "fluorescent activated cell sorting" or "FACS", as used herein, refers to a technique for counting, examining, and sorting microscopic particles suspended in a stream of fluid. It allows simultaneous multiparametric analysis of the physical and/or chemical characteristics of single cells flowing through an optical and/or electronic detection apparatus. Generally, a beam of light (usually laser light) of a single wavelength is directed onto a hydro-dynamically focused stream of fluid. A number of detectors are aimed at the point where the stream passes through the light beam; one in line with the light beam (Forward Scatter, correlates to cell volume) and several perpendicular to the beam, (Side Scatter, correlates to the inner complexity of the particle and/or surface roughness) and one or more fluorescent detectors. Each suspended particle passing through the beam scatters the light in some way, and fluorescent chemicals found in the particle or attached to the particle may be excited into emitting light at a lower frequency than the light source. By analyzing the combinations of scattered and fluorescent light picked up by the detectors it is then possible to derive information about the physical and chemical structure of each individual particle.

The term "data mining", as used herein, refers to the automated or convenient extraction of patterns representing knowledge implicitly stored or captured in large databases, data warehouses, internet websites, other massive information repositories, or data streams.

The terms "overexpress", "overexpressing" and grammatical equivalents, as used herein, refer to the production of a gene product at levels that exceed production in normal or control cells. The term "overexpression" or "highly expressed" may be specifically used in reference to levels of mRNA to indicate a higher level of expression than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed, the amount of 28S rRNA (an abundant RNA transcript present at essentially the same amount in all tissues) present in each sample can be used as a means of normalizing or standardizing the mRNA-specific signal observed on Northern blots. Overexpression may likewise result in elevated levels of proteins encoded by said mRNAs.

The term "laser capture microdissection" or "LCM", as used herein, refers to a method for isolating specific cells of interest from tissue sections wherein a transparent transfer film is applied to the surface of a tissue section. A pulsed laser beam activates a precise spot on the transfer film, fusing the film with the underlying cells of choice. The transfer film with the bonded cells is then lifted off the thin tissue section, leaving all unwanted cells behind. This method is useful for collecting selected cells for DNA, RNA and/or protein analyses. LCM can be performed on a variety of tissue samples including blood smears, cytologic preparations, cultured cells and solid tissues.

The term "colorgram," as used herein, refers to a graphical representation of data where the values obtained from a variable two-dimensional map are represented as colors. As related to the field of molecular biology, heat maps typically represent the level of expression of multiple genes across a number of comparable samples as obtained from a microarray.

The term "apoptosis", as used herein, refers to a form of programmed cell death in multicellular organisms that involves a series of biochemical events that lead to a variety of morphological changes, including blebbing, changes to the cell membrane such as loss of membrane asymmetry and attachment, cell shrinkage, nuclear fragmentation, chromatin condensation, and chromosomal DNA fragmentation. Defective apoptotic processes have been implicated in an extensive variety of diseases; for example, defects in the apoptotic pathway have been implicated in diseases associated with uncontrolled cell proliferations, such as cancer.

The term "consensus region" or "consensus sequence", as used herein, refers to the conserved sequence motifs that show which nucleotide residues are conserved and which nucleotide residues are variable when comparing multiple DNA, RNA, or amino acid sequence alignments. When comparing the results of a multiple sequence alignment, where related sequences are compared to each other, and similar functional sequence motifs are found. The consensus sequence shows which residues are conserved (are always the same), and which residues are variable. A consensus sequence may be a short sequence of nucleotides, which is found several times in the genome and is thought to play the same role in its different locations. For example, many transcription factors recognize particular consensus sequences in the promoters of the genes they regulate. In the same way restriction enzymes usually have palindromic consensus sequences, usually corresponding to the site where they cut the DNA. Splice sites (sequences immediately surrounding the exon-intron boundaries) can also be considered as consensus sequences. In one aspect, a consensus sequence defines a putative DNA recognition site, obtained for example, by aligning all known examples of a certain recognition site and defined as the idealized sequence that represents the predominant base at each position. Related sites should not differ from the consensus sequence by more than a few substitutions.

The term "linkage", or "genetic linkage," as used herein, refers to the phenomenon that particular genetic loci of genes are inherited jointly. The "linkage strength" refers to the probability of two genetic loci being inherited jointly. As the distance between genetic loci increases, the loci are more likely to be separated during inheritance, and thus linkage strength is weaker.

The term "neighborhood score", as used herein, refers to the relative value assigned to a genomic locus based on a geometry-weighted sum of expression scores of all the genes on a given chromosome, as a measurement of the copy number status of the locus. A positive neighborhood score is indicative of an increase in copy number, whereas a negative neighborhood score is indicative of a decrease in copy number.

The term "expression score", as used herein, refers to the expression differences (i.e., the level of transcription (RNA) or translation (protein)) between comparison groups on a given chromosome. The expression score for a given gene is calculated by correlating the level of expression of said gene with a phenotype in comparison. For example, an expression score may represent a comparison of the expression differences of a given gene in normal vs. abnormal conditions, such as parental vs. drug-resistant cell lines. As used herein, the term "regional expression score" refers to the expression score of gene(s) in proximity to the locus in consideration. Since linkage strength between genetic loci decreases (i.e. decays) as the distance between them increases, the "regional expression score" more accurately reflects the expression differences between comparison groups by assigning greater weight to the expression scores of genes in proximity to the locus in consideration.

The terms "geometry-weighted" or "geometry-weighted sum", as used herein, refers to the significance attached to a given value, for example an "expression score," based on physical position, including but not limited to genomic position. Since linkage strength between genetic loci decreases (i.e. decays) as the distance between them increases, the "weight" assigned to a given value is adjusted accordingly.

The term "hierarchical clustering analysis" as used herein refers to any of several methods of statistical analysis of datasets that maps data into "clusters" according to their degree of similarity to one another. In the context of the instant invention, certain genes, whether or not they are functionally related, may be highly co-expressed (or poorly expressed) in a particular cell-type. That is, they "cluster" in that cell type in respect of their level of expression, whereas their expression is disparate in other cell types.

The term "matched samples", as used herein, as for example "matched cancer samples" refers to a sample in which individual members of the sample are matched with every other sample by reference to a particular variable or quality other than the variable or quality immediately under investigation. Comparison of dissimilar groups based on specified characteristics is intended to reduce bias and the possible effects of other variables. Matching may be on an individual (matched pairs) or a group-wide basis.

The term "genomic segments", as used herein, refers to any defined part or region of a chromosome, and may contain zero, one or more genes.

The term "diagnose" or "diagnosis", as used herein, refers to the determination, recognition, or identification of the nature, cause, or manifestation of a condition based on signs, symptoms, and/or laboratory findings.

DETAILED DESCRIPTION

Embodiments of the present invention relate to methods of finding gene expression signatures in cancerous cells and in circulating endothelial cells, both of which circulate at very low concentrations in blood and other body fluids, and using those signatures to detect such cells. In some embodiments, cells that originate from tumors of diverse epithelial lineage are detected. The methods yield gene expression signatures that are capable of distinguishing among different types of cancer cells, normal cells and circulating endothelial cells. The methods that embody the invention are practical for use with samples of cells that have been highly enriched on a collagen-based cell adhesion matrix or other material to which the cells adhere. Accordingly, circulating cancer cells, although exceedingly rare, are amenable to detection and characterization by the methods.

The applicant, while not intending to be bound by any mechanistic explanation or construction of the embodiments of the invention herein described, believes that certain cells of epithelial lineage, metastatic cancer cells prominent among them, and circulating endothelial progenitor cells, have a peculiar adhesive property mediated by so-called invadopodia. Invadopodia evidently bind to extracellular matrices tightly, specifically, and invasively (Aoyama and Chen, 1990; Chen and Chen, 1987; Chen et al., 1994a; Chen et al., 1984; Chen et al., 1994b; Chen, 1996; Chen, 1989; Chen and Wang, 1999; Ghersi et al., 2002; Goldstein and Chen, 2000; Goldstein et al., 1997; Kelly et al., 1994; Monsky et al., 1994; Monsky et al., 1993; Mueller et al., 1999; Mueller and Chen, 1991; Mueller et al., 1992; Nakahara et al., 1996; Nakahara et al., 1998; Nakahara et al., 1997; Pavlaki et al., 2002; Pineiro-Sanchez et al., 1997; Saga et al., 1988; Zucker et al., 2000; Zukowska-Grojec et al., 1998).

The applicant has devised, and continues to improve, an artificial extracellular matrix or "cell adhesion matrix" (hereinafter "CAM") that selectively captures tumor cells circulating in blood or other body fluids such as lymph and ascites. Depending upon the specific design of the CAM, it may capture a few other cell types, but it leaves behind in solution nearly all leukocytes/monocytes, red cells and dead or dying tumor cells. A CAM suitable for use in embodiments of the instant invention is provided in, for example, Vita-Assay™, Vitatex Inc., Stony Brook, N.Y. as a collagen-based film, or in Vita-Cap™, Vitatex Inc., Stony Brook, N.Y. as a collagen-based coating on the inside of a tube. U.S. Patent Application Publication 2005/0244843 (incorporated herein by reference in its entirety for all purposes, together with any patent that issues thereon) describes in detail the use of these matrices, and devices in which they may be conveniently used, to extract endogenous or exogenous circulating tumor cells from blood.

The applicant and others have noted that genes are present in both primary tumor cells and CTCs, and in CECs, that could be used to resolve the tissue-site of origin of CTCs, determine specific cancer subtypes, predict the metastatic potential of a patient, reduce or prevent the misidentification of a CEC as a CTC and diagnose and monitor cardiovascular diseases that involve CECs. With the advent of multiplex techniques such as micro-array and Real-Time PCR for analyzing biomolecules, and suitable cell enrichment techniques, it is now convenient to embody the instant invention in methods that provide the artisan with the means to organize these genes into diagnostic sets or "signatures" and exploit those signatures for such purposes.

In preliminary work, the applicant extracted RNA from CTC fractions prepared from the blood of cancer patients and compared it with the RNA extracted from circulating normal cells (CNC) from healthy individuals. The applicant identified CTC gene expression signatures specific for colon and breast cancers, in which 42 genes for colon cancer and 62 genes for breast cancer are expressed in specific patterns for each type of cancer. The CTC signatures proved to be useful in discriminating normal from cancer samples when they were represented by selection of any reducing number of genes from the 42 colon breast cancer and 62 breast cancer genes down to the minimum of two (one gene upregulated and one gene downregulated) that retained the expression pattern, in which approximately ⅗ genes were upregulated and ⅖ down-regulated. Importantly, the CTC signatures for colon cancer were useful in discriminating cancer from normal samples using only a pair of upregulated (MUC8) and down-regulated (CEACAM1, IL6ST or COL4A3BP) genes selected from the colon CTC signature genes. Similarly, the CTC signatures for breast cancer were useful in discriminating cancer from normal samples using only a pair of upregulated (CDH1 or ST14) and down-regulated (SDCCAG1 or EPAS1) genes selected from the breast CTC signature genes.

The CTC signatures found in the preliminary work for each cancer type were particularly useful in differentiating blood samples of one type of cancer patient from another, when each was represented by selection of reducing numbers of genes down to 25, in which approximately ⅗ genes were upregulated and ⅖ were down-regulated.

The CTC score of a sample was determined as the percentage of genes whose expression patterns matched that of the total number of selected genes in a CTC signature. Blood samples were identified as cancer samples by their CTC scores (greater than 40 cut-off) using the CTC signatures of a specific type of cancer. It was predicted that the CTC signatures consisting of 65 to 24 genes can signify metastatic cells in blood of patients with a specific type of malignant solid tumors, whereas signatures consisting of 65 to 2 genes can be used to discriminate blood samples between normal and a specific type of cancer. The CTC signatures could thus greatly aid in the understanding of cellular origin of tumor metastasis in the peripheral blood, the discovery of new therapeutic and diagnostic targets, and the diagnosis and management of cancer patients.

Figure 17:
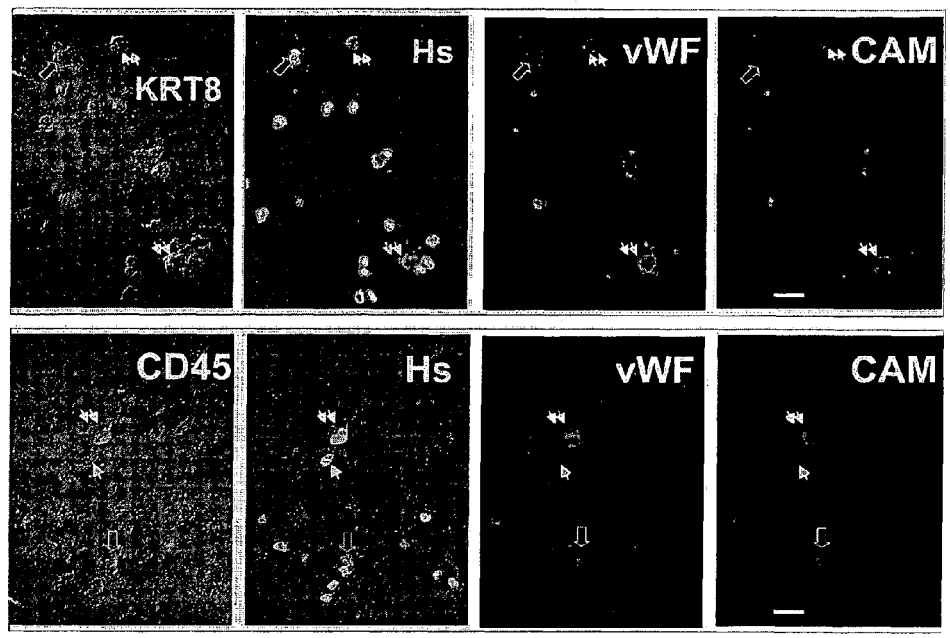
FIG. 17. shows results from a cell-based blood testing kit for detection of CTCs in a patient with epithelial ovarian cancer. Detection of $KRT8^+/Hs^+/VWF^+/CAM^+$ cells (upper panel, double arrows) and $CD45^-/HS^{30}/VWF^+/CAM^+$ cells (lower panel, double arrows) as CTCs in a patient with epithelial ovarian cancer. Other CAM-avid circulating cells are $KRT8^+/Hs^+/VWF^-/CAM^-$ (upper panel, open arrows) or $CD45^-/Hs^+/VWF^-/CAM^-$ (lower panel, open arrows) and leukocytes are $CD45^+/Hs^+/VWF^-/CAM^-$ (lower panel, single arrows). Bar=20 µm.

In one aspect, the invention provides, by means of a discovery platform generated by the inventor, an unique set of bio-markers that define CAM-avid CTCs. The micro-environmental niche for tumor stem cells comprises a collagen-based extracellular matrix that supports the cells as they develop into progenitor and differentiated states (Braun et al., 2007; Shipitsin et al., 2007; Boccaccio and Comoglio, 2006). Accordingly, a collagen-based matrix can be used to isolate and concentrate putative tumor progenitor cell populations from whole blood so that their gene expression profiles (GEP) can be measured. The applicant isolated these cells from 3 mL of blood using functional cell separation devices (as noted above) in which the inner wall was coated with collagen-based cell adhesion matrix (CAM) scaffolds. Any other device that is able to enrich CTCs is within the scope of the invention, however. The CAM isolation method enriched CTCs approximately 100,000-fold directly from whole blood, as judged by their immuno-reactivity against the standard pan-epithelial cell marker cytokeratins (CK) and CAM ingestion, as shown in FIG. 17. Consequently, these cells come to represent 1-10% of the final cell population, with the remainder of the cells being CD45+ leukocytes. Based on the assumption that CTCs are lacking in the blood of healthy subjects, global GEP of the circulating cells isolated by CAM from 3 mL blood of 10 healthy subjects (0 CTCs) and 10 colorectal cancer patients (approximately 300-1,000 CTCs) was used to define CTC markers using the Affymetrix HG U133 Plus2 chip (containing 54,675 gene probes). In addition, the selected genes were cross-examined using 2 additional healthy subjects, 9 patients with breast cancer, and 5 patients with ovarian cancer. Finally, resulting lists of bio-markers were then tested using a validation set of blood samples that consisted of samples from 9 healthy subjects, 9 colorectal cancer patients, and 20 breast cancer patients. Table 10 lists the number of healthy subjects and that of cancer patients with their corresponding cancer type and stage used in this analysis.

TABLE 10

Blood samples from healthy subjects and cancer patients used in the gene expression analysis[note 1].

| Training set | | | | | |
|---|---|---|---|---|---|
| subject | Key | subject | Key | subject | Key |
| 222525 | N01-F | 222525 | N01-F | 222525 | N01-F |
| 222526 | N02-F | 222526 | N02-F | 222526 | N02-F |
| 222527 | N03-M | 222528 | N04-F | 222528 | N04-F |

TABLE 10-continued

Blood samples from healthy subjects and cancer patients used in the gene expression analysis[note 1].

| 222528 | N04-F | 222529 | N05-F | 222529 | N05-F |
|---|---|---|---|---|---|
| 222529 | N05-F | 222530 | N06-F | 222530 | N06-F |
| 222530 | N06-F | 222531 | N20-F | SB351 | OCa01-IV |
| 222533 | N07-M | 222532 | N21-F | SB369 | OCa02-IIIc |
| 222534 | N08-M | SA145 | BCa01-II | SB374 | OCa03-IIIc |
| 222535 | N09-M | SA149 | BCa02-III | SB376 | OCa04-IIIc |
| 222536 | N10-M | SA160 | BCa03-II | SB379 | OCa05-IIIc |
| SA183 | CCa01-IV | SA161 | BCa04-I | | |
| SA184 | CCa02-IV | SA162 | BCa05-III | | |
| SA185 | CCa03-IV | SA163 | BCa06-II | | |
| SA186 | CCa04-IV | SA166 | BCa07-III | | |
| SA187 | CCa05-IV | SA169 | BCa08-II/III | | |
| SA188 | CCa06-IV | SA170 | BCa09-II | | |
| SA189 | CCa07-IV | | | | |
| VA352 | CCa08-IV | | | | |
| VA353 | CCa09-II | | | | |
| VA354 | CCa10-II | | | | |

| Validation set | | | |
|---|---|---|---|
| subject | Key | subject | Key |
| 222488f | N11-F | 222488f | N11-F |
| 222490f | N12-F | 222490f | N12-F |
| 222492m | N13-M | 222492m | N13-M |
| 222495m | N14-M | 222495m | N14-M |
| 222496m | N15-M | 222496m | N15-M |
| 222497m | N16-M | 222497m | N16-M |
| 222537m | N17-M | 222537m | N17-M |
| 222538m | N18-M | 222538m | N18-M |
| 222539m | N19-M | 222539m | N19-M |
| SA187 | CCa11-IV | SA171 | BCa10-I |
| SA190 | CCa12-IV | SA172 | BCa11-II |
| SA205 | CCa13-IV | SA173 | BCa12-II |
| SA206 | CCa14-IV | SA175 | BCa13-III |
| SA207 | CCa15-III | SA176 | BCa14-III |
| SA218 | CCa16-IV | SA177 | BCa15-I |
| SA220 | CCa17-II | SA178 | BCa16-I |
| SA224 | CCa18-IV | SA179 | BCa17-II |
| SA225 | CCa19-III | SA180 | BCa18-III |
| | | SA181 | BCa19-III |
| | | SA182 | BCa20-I |
| | | SA196 | BCa21-II |
| | | SA201 | BCa22-III |
| | | SA202 | BCa23-III |
| | | SA203 | BCa24-III |
| | | SA204 | BCa25-III |
| | | SA208 | BCa26-IV |
| | | SA209 | BCa27-III |
| | | SA210 | BCa28-I |
| | | SA211 | BCa29-I |

[note 1] Samples from Stony Brook University Hospital were labeled SB or SA; those from Veteran Administration Medical Center at Northport, NY were labeled VA. Prefix: N01, normal subject 1; CCa01, colorectal cancer patient 1; BCa01, breast cancer patient 1; OCa01, ovarian cancer patient 1. Suffix: N01-F, normal subject 1-female; CCa01-IV, colorectal cancer patient 1-stage IV.

Figure 11:
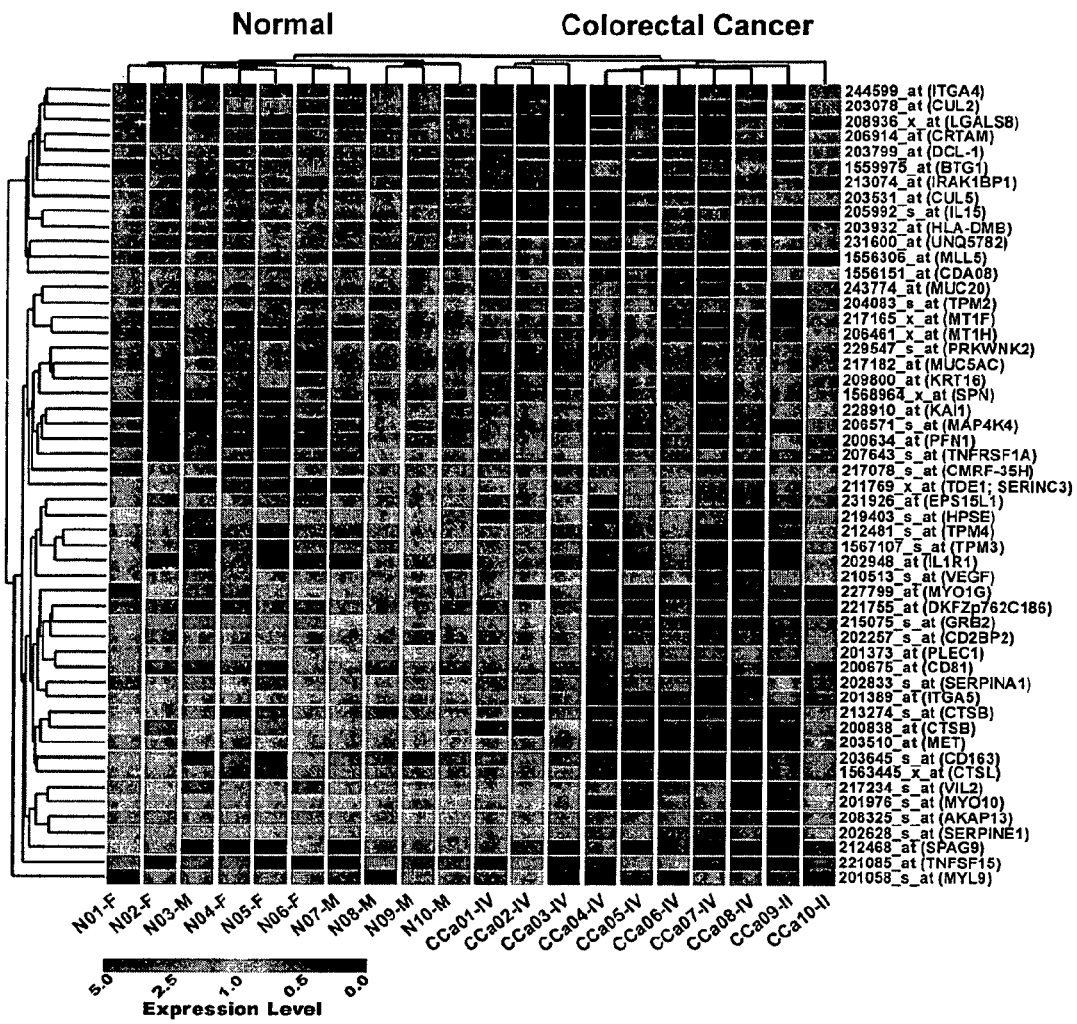
FIG. 11. shows the 53 genes associated with circulating cells isolated by CAM from 10 healthy subjects and 10 patients with colorectal cancer. Colorgram depicts high (red) and low (blue) relative levels of gene expression.

Using the GeneSpring 7.2 program, 2,272 gene probes showed a fold-change >2 at a probability<0.05 of that fold-change not being an actual difference, with the Multi-Testing Correction subroutine "on" to reduce false discovery rate ("FDR"). Among these genes, 53 probes were selected based on >80% matches of differential expression these genes in normal samples as compared to cancer samples. Table 11 lists the 53 probes and corresponding genes with Genbank numbers cited that were results of global gene expression profiling of CAM-enriched circulating cells isolated from normal and colorectal cancer samples. Using condition tree clustering, 13 genes that were upregulated in normal samples clustered in the top panel and 40 genes that were upregulated in cancer samples clustered in the bottom panel (FIG. 11 and Table 11). In addition, hierarchical clustering placed each sample into an order of normal or cancer groups (FIG. 11 and Table 11). This analysis provides a platform necessary for CTC and CEC bio-marker discovery.

TABLE 11

53 gene probes selected using global gene expression profiling of CAM-enriched circulating cells isolated from normal and colorectal cancer samples[note 1].

| Gene ID | Common | Genbank | Description |
| --- | --- | --- | --- |
| | | | Genes upregulated in normal samples |
| 244599_at | ITGA4 | AW770102 | integrin, alpha 4 (antigen CD49D, alpha 4 subunit of VLA-4 receptor) |
| 203078_at | CUL2 | U83410 | Cullin 2 |
| 208936_x_at | LGALS8 | AF074000 | Lectin, galactoside-binding, soluble, 8 (galectin 8); synonyms: Gal-8, PCTA1, PCTA-1, Po66-CBP; isoform b is encoded by transcript variant 2; Po66 carbohydrate binding protein; prostate carcinoma tumor antigen 1; go_component: extracellular space [goid 0005615] [evidence TAS] [pmid 8692978]; go_function: sugar binding [goid 0005529] [evidence IEA]; go_function: sugar binding [goid 0005529] [evidence TAS] [pmid 8692978]; *Homo sapiens* lectin, galactoside-binding, soluble, 8 (galectin 8) (LGALS8), transcript variant 2, mRNA.; isoform b is encoded by transcript variant 3; *Homo sapiens* lectin, galactoside-binding, soluble, 8 (galectin 8) (LGALS8), transcript variant 3, mRNA.; isoform a is encoded by transcript variant 4; *Homo sapiens* lectin, galactoside-binding, soluble, 8 (galectin 8) (LGALS8), transcript variant 4, mRNA. |
| 206914_at | CRTAM | NM_019604 | Class-I MHC-restricted T cell associated molecule |
| 203799_at | DCL-1 | NM_014880 | CD302 antigen |
| 1559975_at | BTG1 | BC009050 | B-cell translocation gene 1, anti-proliferative |
| 213074_at | IRAK1BP1 | BG545769 | interleukin-1 receptor-associated kinase 1 binding protein 1 |
| 203531_at | CUL5 | BF435809 | cullin 5 |
| 205992_s_at | IL15 | NM_000585 | Interleukin 15; synonyms: IL-15, MGC9721; isoform 1 precursor is encoded by transcript variant 1; go_component: endosome [goid 0005768] [evidence TAS] [pmid 10851076]; go_component: Golgi apparatus [goid 0005794] [evidence TAS] [pmid 10851076]; go_component: membrane fraction [goid 0005624] [evidence TAS] [pmid 10851076]; go_component: extracellular space [goid 0005615] [evidence TAS] [pmid 10851076]; go_component: integral to plasma membrane [goid 0005887] [evidence TAS] [pmid 10851076]; go_function: signal transducer activity [goid 0004871] [evidence TAS] [pmid 8178155]; go_function: signal transducer activity [goid 0004871] [evidence TAS] [pmid 10851076]; go_function: hematopoietin/interferon-class (D200-domain) cytokine receptor binding [goid 0005126] [evidence IEA]; go_process: immune response [goid 0006955] [evidence TAS] [pmid 8178155]; go_process: cell-cell signaling [goid 0007267] [evidence TAS] [pmid 7759105]; go_process: signal transduction [goid 0007165] [evidence TAS] [pmid 8178155]; go_process: |
| 203932_at | HLA-DMB | NM_002118 | Major histocompatibility complex, class II, DM beta |
| 231600_at | UNQ5782 | AI657064 | macrophage antigen h |
| 1556306_at | MLL5 | AA082707 | myeloid/lymphoid or mixed-lineage leukemia 5 (trithorax homolog, *Drosophila*) |
| 1556151_at | CDA08 | AI077660 | T-cell immunomodulatory protein |
| | | | Genes upregulated in cancer samples |
| 243774_at | MUC20 | AA132448 | zo20a03.s1 Stratagene colon (#937204) *Homo sapiens* cDNA clone IMAGE: 587404 3', mRNA sequence. |
| 204083_s_at | TPM2 | NM_003289 | Tropomyosin 2 (beta) |
| 217165_x_at | MT1F | M10943 | Metallothionein 1F (functional) |
| 206461_x_at | MT1H | NM_005951 | Metallothionein 1H |

TABLE 11-continued 53 gene probes selected using global gene expression profiling of CAM-enriched circulating cells isolated from normal and colorectal cancer samples[note 1].

| Gene ID | Common | Genbank | Description |
|---|---|---|---|
| 229547_s_at | PRKWNK2 | AI832477 | at69b10.x1 Barstead colon HPLRB7 *Homo sapiens* cDNA clone IMAGE: 2377243 3', mRNA sequence. |
| 217182_at | MUC5AC | Z34282 | *H. sapiens* (MAR11) MUC5AC mRNA for mucin (partial). |
| 209800_at | KRT16 | AF061812 | Keratin 16 (focal non-epidermolytic palmoplantar keratoderma) |
| 1568964_x_a | SPN | BC035510 | Sialophorin (gpL115, leukosialin, CD43) |
| 228910_at | KAI1 | AI870617 | kangai 1 (suppression of tumorigenicity 6, prostate; CD82 antigen (R2 leukocyte antigen, antigen detected by monoclonal and antibody IA4)) |
| 206571_s_at | MAP4K4 | NM_004834 | Mitogen-activated protein kinase kinase kinase kinase 4; synonyms: HGK, NIK, FLH21957, FLJ20373, KIAA0687; isoform 2 is encoded by transcript variant 2; HPK/GCK-like kinase; hepatocyte progenitor kinase-like/germinal center kinase-like kinase; go_component: cellular component unknown [goid 0008372] [evidence ND]; go_function: ATP binding [goid 0005524] [evidence IEA]; go_function: ATP binding [goid 0005524] [evidence IDA] [pmid 9890973]; go_function: nucleotide binding [goid 0000166] [evidence IEA]; go_function: transferase activity [goid 0016740] [evidence IEA]; go_function: small GTPase regulator activity [goid 0005083] [evidence IEA]; go_function: protein-tyrosine kinase activity [goid 0004713] [evidence IEA]; go_function: protein serine/threonine kinase activity [goid 0004674] [evidence IEA]; go_function: protein serine/threonine kinase activity [goid 0004674] [evidence IDA] [pmid 9890973]; go_process: response to stress [goid 0006950] [evidence IDA] [pmid 9890973]; go_process: protein kinase cascade [goi |
| 200634_at | PFN1 | NM_005022 | Profilin 1 |
| 207643_s_at | TNFRSF1A | NM_001065 | Tumor necrosis factor receptor superfamily, member 1A |
| 217078_s_at | CMRF-35H | AJ010102 | CD300A antigen |
| 211769_x_at | TDE1; SERINC3 | BC006088 | Serine incorporator 3; synonyms: TDE, TDE1, AIGP1, TMS-1, DIFF33, SBBI99; placental transmembrane protein (mouse testicular tumor differentially expressed); transmembrane protein SBBI99; tumour differentially expressed 1; tumor differentially expressed 1; go_component: membrane [goid 0016020] [evidence IEA]; go_component: integral to membrane [goid 0016021] [evidence TAS] [pmid 10559794]; *Homo sapiens* serine incorporator 3 (SERINC3), transcript variant 2, mRNA. |
| 231926_at | EPS15L1 | AK023744 | Epidermal growth factor receptor pathway substrate 15-like 1 |
| 219403_s_at | HPSE | NM_006665 | Heparanase |
| 212481_s_at | TPM4 | AI214061 | tropomyosin 4 |
| 1567107 s at | TPM3 | AF362887 | Tropomyosin 3; synonyms: TRK, NEM1, MGC72094; isoform 2 is encoded by transcript variant 2; go_component: cytoskeleton [goid 0005856] [evidence NAS] [pmid 3418707]; go_component: muscle thin filament tropomyosin [goid 0005862] [evidence TAS] [pmid 3018581]; go_function: actin binding [goid 0003779] [evidence IEA]; go_process: muscle development [goid 0007517] [evidence IEA]; go_process: regulation of muscle contraction [goid 0006937] [evidence NAS]; *Homo sapiens* tropomyosin 3 (TPM3), transcript variant 2, mRNA. |
| 202948_at | IL1R1 | NM_000877 | Interleukin 1 receptor, type I |
| 210513_s_at | VEGF | AF091352 | vascular endothelial growth factor |

TABLE 11-continued 53 gene probes selected using global gene expression profiling of CAM-enriched circulating cells isolated from normal and colorectal cancer samples[note 1].

| Gene ID | Common | Genbank | Description |
| --- | --- | --- | --- |
| 227799_at | MYO1G | AI693688 | myosin IG |
| 221755_at | DKFZp762C186 | BG334196 | tangerin |
| 215075_s_at | GRB2 | L29511 | Growth factor receptor-bound protein 2; synonyms: ASH, Grb3-3, MST084, MSTP084, EGFRBP-GRB2; isoform 2 is encoded by transcript variant 2; HT027; growth factor receptor-bound protein 3; epidermal growth factor receptor-binding protein GRB; abundant SRC homology; go_component: cytosol [goid 0005829] [evidence TAS] [pmid 14722116]; go_function: protein binding [goid 0005515] [evidence IPI] [pmid 14722116]; go_function: SH3/SH2 adaptor activity [goid 0005070] [evidence TAS] [pmid 8253073]; go_function: epidermal growth factor receptor binding [goid 0005154] [evidence IPI] [pmid 12577067]; go_process: cell-cell signaling [goid 0007267] [evidence TAS] [pmid 8253073]; go_process: intracellular signaling cascade [goid 0007242] [evidence IEA]; go_process: Ras protein signal transduction [goid 0007265] [evidence TAS] [pmid 8253073]; go_process: epidermal growth factor receptor signaling pathway [goid 0007173] [evidence TAS] [pmid 1322798]; *Homo sapiens* growth factor receptor-bound protein 2 (GRB2), transcript variant |
| 202257_s_at | CD2BP2 | NM_006110 | CD2 antigen (cytoplasmic tail) binding protein 2 |
| 201373_at | PLEC1 | NM_000445 | Plectin 1, intermediate filament binding protein 500 kDa; synonyms: HD1, PCN, EBS1, EBSO, PLTN, PLEC1b; isoform 2 is encoded by transcript variant 2; plectin 1, intermediate filament binding protein, 500 kD; hemidesmosomal protein 1; epidermolysis bullosa simplex 1 (Ogna); go_component: cytoskeleton [goid 0005856] [evidence IEA]; go_component: plasma membrane [goid 0005886] [evidence NAS] [pmid 8633055]; go_component: intermediate filament [goid 0005882] [evidence NR]; go_function: actin binding [goid 0003779] [evidence IEA]; go_function: structural constituent of muscle [goid 0008307] [evidence TAS] [pmid 8696340]; go_function: structural constituent of cytoskeleton [goid 0005200] [evidence NR]; go_process: cytoskeletal anchoring [goid 0007016] [evidence NR]; *Homo sapiens* plectin 1, intermediate filament binding protein 500 kDa (PLEC1), transcript variant 2, mRNA.; isoform 3 is encoded by transcript variant 3; *Homo sapiens* plectin 1, intermediate filament binding protein 500 kDa (PLEC1), transcript variant 3, mR |
| 200675_at | CD81 | NM_004356 | CD81 antigen (target of antiproliferative antibody 1) |
| 202833_s_at | SERPINA1 | NM_000295 | Serpin peptidase inhibitor, clade A (alpha-1 antiproteinase, antitrypsin), member 1 |
| 201389_at | ITGA5 | NM_002205 | Integrin, alpha 5 (fibronectin receptor, alpha polypeptide) |
| 213274_s_at | CTSB | AA020826 | ze64b04.s1 Soares retina N2b4HR *Homo sapiens* cDNA clone IMAGE: 363727 3' similar to gb: M14221 CATHEPSIN B PRECURSOR (HUMAN);, mRNA sequence. |
| 200838_at | CTSB | NM_001908 | Cathepsin B; synonyms: APPS, CPSB; APP secretase; preprocathepsin B; cathepsin B1; amyloid precursor protein secretase; cysteine protease; go_component: lysosome [goid 0005764] [evidence IEA]; |

TABLE 11-continued 53 gene probes selected using global gene expression profiling of CAM-enriched circulating cells isolated from normal and colorectal cancer samples[note 1].

| Gene ID | Common | Genbank | Description |
| --- | --- | --- | --- |
| | | | go_component: intracellular [goid 0005622] [evidence TAS] [pmid 1645961]; go_function: cathepsin B activity [goid 0004213] [evidence TAS] [pmid 1645961]; go_process: proteolysis [goid 0006508] [evidence TAS] [pmid 3463996]; *Homo sapiens* cathepsin B (CTSB), transcript variant 2, mRNA.; *Homo sapiens* cathepsin B (CTSB), transcript variant 3, mRNA.; *Homo sapiens* cathepsin B (CTSB), transcript variant 4, mRNA.; *Homo sapiens* cathepsin B (CTSB), transcript variant 5, mRNA. |
| 203510_at | MET | BG170541 | met proto-oncogene (hepatocyte growth factor receptor) |
| 203645_s_at | CD163 | NM_004244 | CD163 antigen; synonyms: M130, MM130; isoform b is encoded by transcript variant 2; macrophage-associated antigen; go_component: membrane [goid 0016020] [evidence IEA]; go_component: extracellular region [goid 0005576] [evidence NAS]; go_component: integral to plasma membrane [goid 0005887] [evidence TAS] [pmid 8370408]; go_function: scavenger receptor activity [goid 0005044] [evidence NAS] [pmid 8370408]; go_function: scavenger receptor activity [goid 0005044] [evidence TAS] [pmid 8370408]; go_process: antimicrobial humoral response (sensu Vertebrata) [goid 0019735] [evidence TAS] [pmid 8370408]; *Homo sapiens* CD163 antigen (CD163), transcript variant 2, mRNA. |
| 1563445_x_at | CTSL | L25629 | Human cathepsin-L-like (CTSLL3) mRNA. |
| 217234_s_at | VIL2 | AF199015 | Villin 2 (ezrin) |
| 201976_s_at | MYO10 | NM_012334 | Myosin X |
| 208325_s_at | AKAP13 | NM_006738 | A kinase (PRKA) anchor protein 13; synonyms: BRX, LBC, HA-3, Ht31, c-lbc, AKAP-Lbc, FLJ11952, PROTO-LB, PROTO-LBC; isoform 2 is encoded by transcript variant 2; A-kinase anchoring protein; guanine nucleotide exchange factor Lbc; breast cancer nuclear receptor-binding auxiliary protein; lymphoid blast crisis oncogene; go_component: membrane fraction [goid 0005624] [evidence TAS] [pmid 9891067]; go_function: kinase activity [goid 0016301] [evidence IEA]; go_function: metal ion binding [goid 0046872] [evidence IEA]; go_function: receptor activity [goid 0004872] [evidence IEA]; go_function: diacylglycerol binding [goid 0019992] [evidence IEA]; go_function: signal transducer activity [goid 0004871] [evidence TAS] [pmid 8290273]; go_function: cAMP-dependent protein kinase activity [goid 0004691] [evidence NAS] [pmid 1618839]; go_function: guanyl-nucleotide exchange factor activity [goid 0005085] [evidence IEA]; go_function: Rho guanyl-nucleotide exchange factor activity [goid 0005089] [evidence NR]; go_process: int |
| 202628_s_at | SERPINE1 | NM_000602 | Serpin peptidase inhibitor, Glade E (nexin, plasminogen activator inhibitor type 1), member 1 |
| 212468_at | SPAG9 | AK023512 | Sperm associated antigen 9; synonyms: HSS, JLP, HLC4, PHET, PIG6, FLJ13450, FLJ14006, FLJ34602, KIAA0516, MGC14967, MGC74461, MGC117291; isoform 2 is encoded by transcript variant 2; sperm surface protein; JNK/SAPK-associated protein; JNK interacting protein; sperm specific protein; c-Jun NH2-terminal kinase-associated leucine zipper protein; |

TABLE 11-continued

53 gene probes selected using global gene expression profiling of CAM-enriched circulating cells isolated from normal and colorectal cancer samples[note 1].

| Gene ID | Common | Genbank | Description |
|---|---|---|---|
| | | | Max-binding protein; JNK-associated leucine-zipper protein; HLC-4 protein; lung cancer oncogene 4; proliferation-inducing gene 6; sperm associated antigen 9 transcript variant 1; go_component: integral to membrane [goid 0016021] [evidence TAS] [pmid 9480848]; go_function: protein binding [goid 0005515] [evidence IPI] [pmid 14743216]; go_process: spermatogenesis [goid 0007283] [evidence TAS] [pmid 9480848]; *Homo sapiens* sperm associated antigen 9 (SPAG9), transcript variant 2, mRNA. |
| 221085_at | TNFSF15 | NM_005118 | Tumor necrosis factor (ligand) superfamily, member 15 |
| 201058_s_at | MYL9 | NM_006097 | Myosin, light polypeptide 9, regulatory; synonyms: LC20, MLC2, MRLC1, MYRL2, MGC3505; isoform b is encoded by transcript variant 2; myosin RLC; myosin regulatory light chain 2, smooth muscle isoform; go_component: myosin [goid 0016459] [evidence IEA]; go_component: muscle myosin [goid 0005859] [evidence TAS] [pmid 2526655]; go_function: motor activity [goid 0003774] [evidence IEA]; go_function: calcium ion binding [goid 0005509] [evidence IEA]; go_function: structural constituent of muscle [goid 0008307] [evidence TAS] [pmid 2526655]; go_process: muscle development [goid 0007517] [evidence IEA]; go_process: regulation of muscle contraction [goid 0006937] [evidence TAS] [pmid 2526655]; *Homo sapiens* myosin, light polypeptide 9, regulatory (MYL9), transcript variant 2, mRNA. |

[note 1] 53 gene probes were selected from 2,272 probes in the Affymetrix HG_U133_Plus_2 chip containing 54,675 probes that showed fold change >2; P > 0.05, and >80% sample match of expression pattern, as well as with Multi Testing Correction on to reduce FDR rate (GeneSpring 7.2). Both samples and genes were hierarchically clustered by Condition Tree Clustering.

Tumor cell identifiers. In comparison with the CTC gene list published by Smirnov et al. (2005), the initial GEP analysis shown in FIG. 11 and Table 11 reveals an unique panel of tumor genes, including MUC20 PRKWNK2, MUC5AC, KRT16, CMRF-35H, GRB2, PLEC1, CD81, MET and AKAP13, that were upregulated in CAM-enriched cells from blood of colorectal cancer patients but downregulated in CAM-enriched cells from healthy subjects. However, the analysis also shows putative normal cell genes including TPM2, MT1F, MT1H, SPN, HPSE, TPM4, TPM3, SERPINA1, CTSB, CD163, CTSL, and SERPINE1 that were upregulated in CAM-enriched cells from blood of colorectal cancer patients but downregulated in CAM-enriched cells from healthy subjects (FIG. 11 and Table 11).

KRT Tumor Cell Identifiers. In another aspect, as a result of screening the set of cell samples shown in FIG. 11, the invention provides an unique set of KRT biomarkers that define CAM-avid CTCs. To screen KRT and internal control genes for CTC bio-markers, hierarchical clustering was performed between the training set of cell samples shown in FIG. 11 and 99 probes representative of the KRT family (Table 12), 7 probes of leukocyte and monocyte genes and 188 probes of the integrin family that might be related with a common property of CAM-avid cells. FIG. 12A and Table 12 show a set of candidate KRT marker genes (KRT8, KRT16, KRT19, KRT17, KRT18 and KRT20) that exhibited minimal expression in the normal cell samples and significant expression in the colorectal cancer cell samples. The 3 KRT marker genes (KRT8, KRT16 and KRT19) also showed minimal expression in the normal cell samples and significant expression in the breast and ovarian cancer cell samples (FIG. 12B), suggesting that KRT8, KRT16 and KRT19 were in the marker gene set common to the three cancer types. Despite common expression by immune cells, KRT19 has been used as a marker for qPCR detection of CTCs by many groups (Smirnov et al., 2005; Xenidis et al., 2003; Xenidis et al., 2006; Xenidis et al., 2007; Stathopoulou et al., 2006; Iakovlev et al., 2008; Xi et al., 2007; Ignatiadis et al., 2007). Importantly, this study reveals that CAM-cell separation has excluded KRT19+ immune cells and allows the determination of KRT19 as a marker specific for CAM-avid CTCs.

Figure 13:
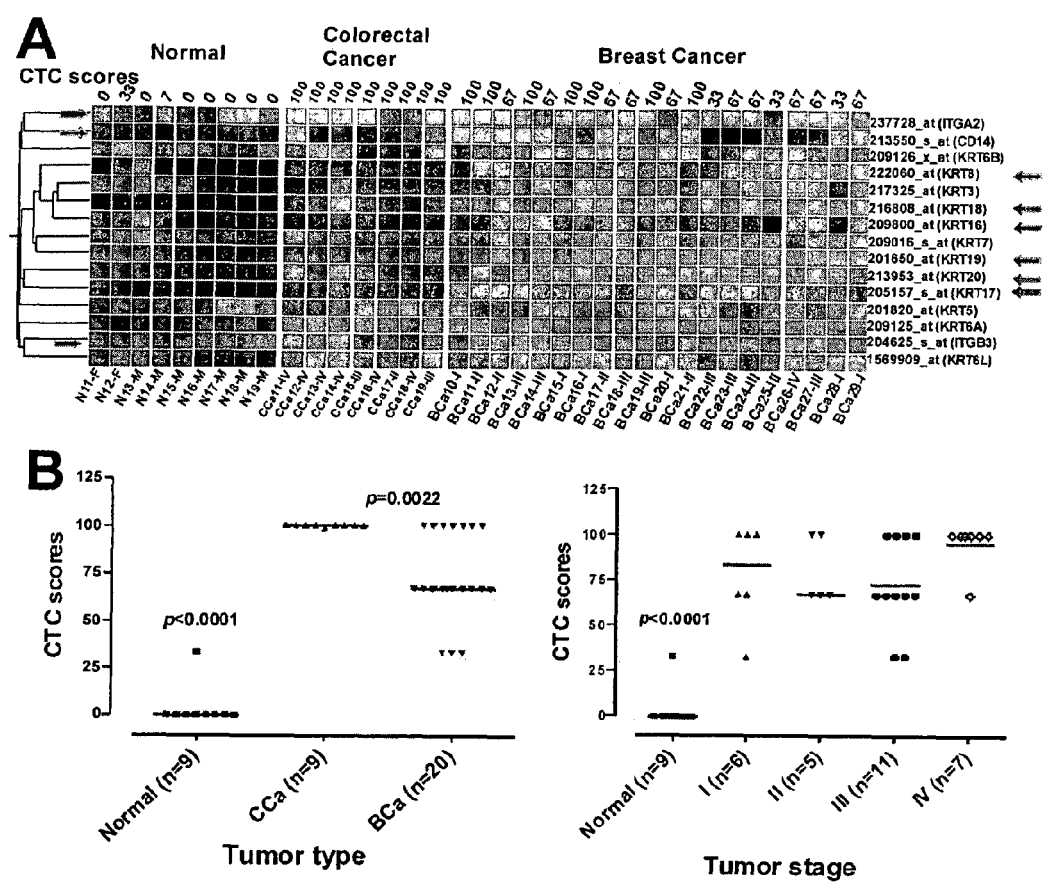
FIG. 13. shows data for the validation of the candidate KRT and internal control genes associated with circulating tumor cells isolated by CAM. Columns represent catalogues of cell samples analyzed. Circulating Normal (N) cells were isolated from healthy donors with suffix M for Male and F for Female. Isolated Circulating Colorectal Cancer (CCa) cells and Breast Cancer (BCa) cells with suffix I-IV being stages of the disease. The CTC score in percentage of each sample is given on the top of each column. Colorgram depicts high (red) and low (blue) relative levels of gene expression. Green arrows point to KRT8, KRT16 and KRT19 that were in the marker gene set common to the three cancer types. Blue arrows indicate KRT17, KRT18 and KRT20 that exhibited minimal expression in the normal cell samples and significant expression in one type of the three cancer cell samples. Red arrows indicate the internal control genes that exhibited no difference between normal and cancer cell samples.

Referring to FIG. 13, where the columns represent catalogues of cell samples analyzed, circulating Normal (N) cells were isolated with the one-step Vita-Cap™ assay from healthy donors with suffix M for Male and F for Female; CCa are circulating Colorectal Cancer (CCa) cells, and BCa being Breast Cancer (BCa) cells isolated by the one-step Vita-Cap™ assay with suffix I-IV being stages of the disease. The CTC score in percentage of each sample is given on the top of each column. Colorgram depicts high (red) and low (blue) relative levels of gene expression. Green arrows point to KRT8, KRT16 and KRT19 that were in the marker gene set common to the three cancer types. Blue arrows indicate KRT17, KRT18 and KRT20 that exhibited minimal expression in the normal cell samples and significant expression in one type of the three cancer cell samples. Red arrows indicate the internal control genes that exhibited no difference between normal and cancer cell samples. FIG. 13B correlates the CTC score and tumor cells in a blood sample based on patients' tumor type and stage. The bars represent median values for each subgroup.

TABLE 12

99 KRT gene probes examined[note 1].

| Gene ID | Common | Genbank | Description |
|---|---|---|---|
| 99 KRT gene probes in Affymetrix HG_U133_Plus_2 chip | | | |
| 1555673_at | KRTAP2-1 | BC012486 | *Homo sapiens* keratin associated protein 2-1, mRNA (cDNA clone IMAGE: 4472166), with apparent retained intron. |
| 1556410_a_at | KRTAP19-1 | AJ457067 | Keratin associated protein 19-1 |
| 1558393_at | KRT7 | BC042076 | Keratin 7 |
| 1558394_s_at | KRT7 | BC042076 | Keratin 7 |
| 1560897_a_at | KRTAP18-11 | AF086314 | keratin associated protein 18-11 |
| 1564803_at | KRTAP11-1 | AJ457065 | Keratin associated protein 11-1 |
| 1564921_at | KRTAP13-1 | AJ457066 | Keratin associated protein 13-1 |
| 1564960_at | KRTAP7-1 | AJ457063 | keratin associated protein 7-1 |
| 1564974_at | KRTAP8-1 | AJ457064 | Keratin associated protein 8-1 |
| 1569909_at | KRT6L | BC039148 | Keratin 6L |
| 201596_x_at | KRT18 | NM_000224 | Keratin 18; synonyms: K18, CYK18; cytokeratin 18; cell proliferation-inducing protein 46; go_component: intermediate filament [goid 0005882] [evidence TAS] [pmid 2434380]; go_function: structural constituent of cytoskeleton [goid 0005200] [evidence NR]; go_process: morphogenesis [goid 0009653] [evidence TAS] [pmid 2434380]; *Homo sapiens* keratin 18 (KRT18), transcript variant 2, mRNA. |
| 201650_at | KRT19 | NM_002276 | Keratin 19 |
| 201820_at | KRT5 | NM_000424 | Keratin 5 (epidermolysis bullosa simplex, Dowling-Meara/Kobner/Weber-Cockayne types) |
| 204734_at | KRT15 | NM_002275 | Keratin 15 |
| 205157_s_at | KRT17 | NM_000422 | Keratin 17 |
| 205900_at | KRT1 | NM_006121 | Keratin 1 (epidermolytic hyperkeratosis) |
| 206677_at | KRTHA1 | NM_002277 | Keratin, hair, acidic, 1 |
| 206969_at | KRTHA4 | NM_021013 | Keratin, hair, acidic, 4 |
| 207023_x_at | KRT10 | NM_000421 | Keratin 10 (epidermolytic hyperkeratosis; keratosis palmaris et plantaris) |
| 207146_at | KRTHA2 | NM_002278 | Keratin, hair, acidic, 2 |
| 207649_at | KRTHA7 | NM_003770 | Keratin, hair, acidic, 7 |
| 207669_at | KRTHB3 | NM_002282 | Keratin, hair, basic, 3 |
| 207670_at | KRTHB5 | NM_002283 | Keratin, hair, basic, 5 |
| 207716_at | KRTHA8 | NM_006771 | Keratin, hair, acidic, 8 |
| 207787_at | KRTHA3B | NM_002279 | Keratin, hair, acidic, 3B |
| 207811_at | KRT12 | NM_000223 | Keratin 12 (Meesmann corneal dystrophy) |
| 207908_at | KRT2A | NM_000423 | Keratin 2A (epidermal ichthyosis bullosa of Siemens) |
| 207935_s_at | KRT13 | NM_002274 | Keratin 13; synonyms: K13, CK13, MGC3781; isoform a is encoded by transcript variant 1; keratin, type I cytoskeletal 13; cytokeratin 13; go_component: intermediate filament [goid 0005882] [evidence IEA]; go_function: structural molecule activity [goid 0005198] [evidence IEA]; go_function: structural constituent of cytoskeleton [goid 0005200] [evidence NR]; go_process: epidermis development [goid 0008544] [evidence TAS] [pmid 7493031]; *Homo sapiens* keratin 13 (KRT13), transcript variant 1, mRNA. |
| 208188_at | KRT9 | NM_000226 | Keratin 9 (epidermolytic palmoplantar keratoderma) |
| 208483_x_at | KRTHA3A | NM_004138 | Keratin, hair, acidic, 3A |
| 209008_x_at | KRT8 | U76549 | Keratin 8 |
| 209016_s_at | KRT7 | BC002700 | Keratin 7 |
| 209125_at | KRT6A | J00269 | unnamed protein product; keratin; Human messenger fragment encoding cytoskeletal keratin (type II). mRNA from cultured epidermal cells from human foreskin. |
| 209126_x_at | KRT6B | L42612 | Keratin 6B |
| 209351_at | KRT14 | BC002690 | Keratin 14 (epidermolysis bullosa simplex, Dowling-Meara, Koebner) |
| 209800_at | KRT16 | AF061812 | Keratin 16 (focal non-epidermolytic palmoplantar keratoderma) |

TABLE 12-continued

99 KRT gene probes examined[note 1].

| Gene ID | Common | Genbank | Description |
|---|---|---|---|
| 210633_x_at | KRT10 | M19156 | Keratin 10 (epidermolytic hyperkeratosis; keratosis palmaris et plantaris) |
| 212236_x_at | KRT17 | Z19574 | Keratin 17 |
| 213240_s_at | KRT4 | X07695 | Keratin 4 |
| 213287_s_at | KRT10 | X14487 | Keratin 10 (epidermolytic hyperkeratosis; keratosis palmaris et plantaris) |
| 213680_at | KRT6B | AI831452 | keratin 6B |
| 213711_at | KRTHB1 | NM_002281 | Keratin, hair, basic, 1 |
| 213953_at | KRT20 | AI732381 | keratin 20 |
| 214031_s_at | KRT7 | AI920979 | keratin 7 |
| 214399_s_at | KRT4 | BF588953 | keratin 4 |
| 214576_at | KRTHA6 | NM_003771 | Keratin, hair, acidic, 6 |
| 214580_x_at | KRT6A | AL569511 | keratin 6A |
| 215189_at | KRTHB6 | X99142 | Keratin, hair, basic, 6 (monilethrix) |
| 216568_x_at | KRT8 | Z83821 | Human DNA sequence from clone RP1-296K21 on chromosome Xq13, complete sequence. |
| 216581_at | KRT18 | AL022068 | Human DNA sequence from clone RP1-167F1 on chromosome 6p22.1-22.3, complete sequence. |
| 216808_at | KRT18 | AL354915 | |
| 216810_at | KRTAP4-7 | AJ406939 | Keratin associated protein 4-7 |
| 216821_at | KRT8 | AL137067 | |
| 216921_s_at | KRTHA5 | X90763 | Keratin, hair, acidic, 5 |
| 217031_at | KRTHB4 | Y19209 | Keratin, hair, basic, 4 |
| 217325_at | KRT3 | X05421 | Keratin 3 |
| 217351_at | KRT8 | AL024458 | Human DNA sequence from clone RP3-344I7 on chromosome Xp11.21-11.3, complete sequence. |
| 218963_s_at | KRT23 | NM_015515 | Keratin 23 (histone deacetylase inducible); synonyms: K23, CK23, HAIK1, MGC26158, DKFZP434G032; isoform b is encoded by transcript variant 2; histone deacetylase inducible keratin 23; hyperacetylation-inducible type I keratin; keratin, type I cytoskeletal 23; cytokeratin 23; type I intermediate filament cytokeratin; go_component: intermediate filament [goid 0005882] [evidence IEA]; go_function: structural molecule activity [goid 0005198] [evidence IEA]; *Homo sapiens* keratin 23 (histone deacetylase inducible) (KRT23), transcript variant 2, mRNA. |
| 220267_at | KRT24 | NM_019016 | Keratin 24 |
| 220970_s_at | KRTAP2-4 | NM_030977 | |
| 220972_s_at | KRTAP9-9 | NM_030975 | |
| 220976_s_at | KRTAP1-1 | NM_030967 | Keratin associated protein 1-3 |
| 220978_at | KRTAP1-3 | NM_030966 | Keratin associated protein 1-3 |
| 222060_at | KRT8 | AI357616 | hypothetical protein LOC90133 |
| 224269_at | KRTAP4-12 | BC004180 | Keratin associated protein 4-12 |
| 224885_s_at | KRTCAP2 | BE260771 | keratinocyte associated protein 2 |
| 228491_at | KRT19 | AW662246 | keratin 19 |
| 230116_at | KRT8 | AL133645 | hypothetical protein LOC90133 |
| 231018_at | KRT18L1 | BF195936 | Hypothetical LOC342979 (LOC342979), mRNA |
| 231461_at | KRT6IRS | AI190071 | keratin 6 irs |
| 233122_at | KRTCAP2 | AU147619 | keratinocyte associated protein 2 |
| 233158_at | KRTHB2 | AI082251 | keratin, hair, basic, 2 |
| 233533_at | KRTAP1-5 | AJ406928 | Keratin associated protein 1-5 |
| 233534_at | KRTAP3-2 | AJ406932 | Keratin associated protein 3-2 |
| 233537_at | KRTAP3-1 | AJ406931 | Keratin associated protein 3-1 |
| 233631_x_at | KRTAP9-2 | AJ406946 | Keratin associated protein 9-2 |
| 233640_x_at | KRTAP9-4 | AJ406948 | Keratin associated protein 9-4 |
| 233681_at | KRTAP3-3 | AJ406933 | Keratin associated protein 3-3 |
| 234631_at | KRTAP4-14 | AJ406940 | LOC388384 (LOC388384), mRNA |
| 234633_at | KRTAP4-14 | AJ406944 | Keratin associated protein 4-14 |
| 234635_at | KRTAP4-10 | AJ406942 | Keratin associated protein 4-10 |
| 234637_at | KRTAP4-5 | AJ406937 | Keratin associated protein 4-5 |
| 234639_x_at | KRTAP9-2 | AJ406950 | keratin associated protein 9-8 |
| 234671_at | KRTAP4-2 | AJ406934 | Keratin associated protein 4-2 |
| 234678_at | KRTAP4-3 | AJ406935 | keratin associated protein 4-3 |
| 234679_at | KRTAP9-3 | AJ406947 | Keratin associated protein 9-3 |
| 234680_at | KRTAP17-1 | AJ406952 | Keratin associated protein 17-1 |
| 234683_at | KRTAP4-15 | AJ406945 | keratin associated protein 4-15 |
| 234684_s_at | KRTAP4-4 | AJ296168 | Keratin associated protein 4-4 |
| 234685_x_at | KRTAP4-9 | AJ406941 | keratin associated protein 4-9 |
| 234691_at | KRTAP2-1 | AJ296345 | keratin associated protein 2-1 |
| 234772_s_at | KRTAP2-2 | AJ406929 | keratin associated protein 2-4 |
| 234880_x_at | KRTAP1-3 | X63338 | *H. sapiens* HB2B gene for high sulfur keratin. |
| 235148_at | KRTCAP3 | BF680458 | keratinocyte associated protein 3 |

TABLE 12-continued

99 KRT gene probes examined[note 1].

| Gene ID | Common | Genbank | Description |
|---|---|---|---|
| 237120_at | KRT1B | AI186548 | keratin 1B |
| 237853_x_at | KRTAP18-4 | BF057369 | keratin associated protein 18-12 |
| 237905_at | KRT25A | AI150703 | keratin 25A |
| 240388_at | KRT25C | AI160083 | keratin 25C |
| 240967_at | KRTAP19-3 | AI288919 | keratin associated protein 19-3 |

[note 1] 99 KRT gene probes in Affymetrix HG_U133_Plus_2 chip were examined in this study and only a single oligo probe from each gene that showed the best gene match, i.e., up-regulated in tumor cells and down-regulated in normal cells from >80% of all samples were selected.

The aforementioned screening revealed another embodiment of the invention wherein cells being characterized as either normal circulating cells or CTCs can be characterized under conditions wherein the data are internally controlled. FIG. 12A and Table 13 show a set of internal control genes (ITGA2, CD14 and ITGB3) that exhibited no deviation between normal and colorectal cancer cell samples. The 3 internal control genes also showed no difference between normal cell samples and breast/ovarian cancer cell samples (FIG. 12B), suggesting that ITGA2, CD14 and ITGB3 were internal control genes useful in nucleic acid testing (DNA microarray or qPCR) for CTCs.

Figure 14:
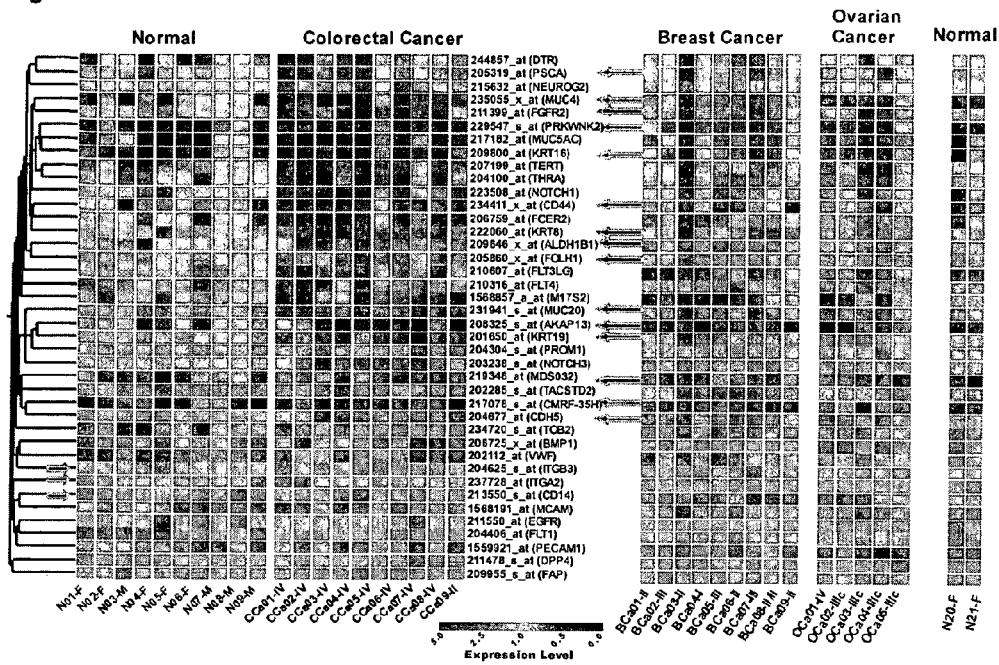
FIG. 14. shows the tumor progenitor cell markers that are preferable CTC markers to be included in a panel for identifying different types of epithelial cancer.

FIG. 11 and >1,000 probes representative of stem cell genes or factors (SCFs), as well as cytokeratins (KRTs), cadherins (CDHs), mucins (MUCs), integrins (ITGs), epithelial membrane antigens (EMA) and tumor-associated antigens (TAAs). FIG. 14A-B and Table 14 show a set of 15 candidate tumor progenitor marker genes (PSCA, CD44, FOLH1, CDH5, MUC4, FGFR2, PRKWNK2, KRT16, KRT8, ALDH1B1, CMRF-35H, CDH5, MDS032, MUC20, AKAP13 and KRT19) upregulated in >90% of colorectal, breast and ovarian cancer samples but in <10% of the normal cell samples; a set of 14 TP genes (DTR, NEUROG2, MUC5AC, TERT, THRA, NOTCH1, FCER2, FLT3LG,

TABLE 13

Selection of KRT genes and internal control genes for CTC markers[note 1].

| Gene ID | Common | Genbank | Description |
|---|---|---|---|
| *Internal control genes[note 2]* | | | |
| 237728_at | ITGA2 | AI733222 | integrin, alpha 2 (CD49B, alpha 2 subunit of VLA-2 receptor) |
| 213550_s_at | CD14 | AA993683 | CD14 antigen |
| 204625_s_at | ITGB3 | BF115658 | integrin, beta 3 (platelet glycoprotein IIIa, antigen CD61) |
| *KRT genes upregulated in cancer samples[Note 3]* | | | |
| 222060_at | KRT8 | AI357616 | hypothetical protein LOC90133 |
| 209800_at | KRT16 | AF061812 | Keratin 16 (focal non-epidermolytic palmoplantar keratoderma) |
| 201650_at | KRT19 | NM_002276 | Keratin 19 |
| 205157_s_at | KRT17 | NM_000422 | Keratin 17 |
| 216808_at | KRT18 | AL354915 | |
| 213953_at | KRT20 | AI732381 | keratin 20 |
| *KRT genes do not deviate between normal and cancer samples[Note 4]* | | | |
| 217325_at | KRT3 | X05421 | Keratin 3 |
| 201820_at | KRT5 | NM_000424 | Keratin 5 (epidermolysis bullosa simplex, Dowling-Meara/Kobner/Weber-Cockayne types) |
| 209125_at | KRT6A | J00269 | unnamed protein product; keratin; Human messenger fragment encoding cytoskeletal keratin (type II). mRNA from cultured epidermal cells from human foreskin. |
| 209126_x_at | KRT6B | L42612 | Keratin 6B |
| 1569909_at | KRT6L | BC039148 | Keratin 6L |
| 209016_s_at | KRT7 | BC002700 | Keratin 7 |

[note 1] Only a single oligo probe from each gene that showed the best gene match, i.e., upregulated in tumor cells and downregulated in normal cells from >80% of all samples were selected.
[note 2] endogenous control genes (CD14, ITGA2, ITGB3) that do not deviate between tumor and normal cells from different individuals were used to assist sorting up-regulated tumor-associated genes in CTCs.
[Note 3] KRT genes were upregulated in cancer samples but downregulated in normal cell samples.
[Note 4] KRT genes did not deviate between normal and cancer cell samples and were clustered with the 3 control genes.

Tumor progenitor cell identifiers. Screening revealed yet another embodiment of the invention wherein tumor progenitor cells in a sample comprising CTCs may be identified by another unique set of biomarkers. Hierarchical clustering was performed between the training set of cell samples shown in FLT4, M17S2; CA125; MUC16, PROM1; CD133, NOTCH3, TACSTD2; GA733 and TOB2) that were upregulated in >70% of colorectal cancer, breast cancer and ovarian cancer samples and in <30% of normal samples; another set of 8-progenitor cell marker genes (BMP1, VWF, MCAM;

CD146; MUC18, EGFR, FLT1, PECAM1; CD31, DPP4; CD26 and FAP; DPP5; seprase; APCE) that expressed at various levels in the normal cell samples and in the cell samples of colorectal, breast and ovarian cancer, and tended to cluster with internal control genes (ITGA2, CD14 and ITGB3) (FIG. 14A-B). The majority of >1,000 genes known to be involved in stem cells and the developmental epithelial lineage showed minimal differences between CAM-enriched cellular samples from cancer patients and healthy donors. Therefore, the 15-tumor progenitor genes are in the CTC marker gene set common to the three cancer types and any one of this gene set can be used in sorting of cancer progenitor cells from normal stem cells present in the circulation. Alternatively, the 7-normal progenitor cell genes are useful in the determination of multiple developmental potentials of CTCs in cell-based assays, as shown in FIG. 17.

The validity of using the identified tumor progenitor cell marker genes to detect tumor progenitor cells in a sample of enriched CTCs was established as summarized in Example 2.

TABLE 14

Selection of tumor progenitor cell genes as CTC markers[note 1].

| Gene ID | Common | Genbank | Description |
| --- | --- | --- | --- |
| Internal control genes (3) - Note 2 | | | |
| 237728_at | ITGA2 | AI733222 | integrin, alpha 2 (CD49B, alpha 2 subunit of VLA-2 receptor) |
| 213550_s_at | CD14 | AA993683 | CD14 antigen |
| 204625_s_at | ITGB3 | BF115658 | integrin, beta 3 (platelet glycoprotein IIIa, antigen CD61) |
| Tumor progenitor genes upregulated in >90% of cancer samples and <10% of normal samples (15) - Note 3 | | | |
| 205319_at | PSCA | NM_005672 | Prostate stem cell antigen |
| 235055_x_at | MUC4 | BF913667 | mucin 4, tracheobronchial |
| 211399_at | FGFR2 | AB030077 | Fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome); synonyms: BEK, JWS, CEK3, CFD1, ECT1, KGFR, TK14, TK25, BFR-1, K-SAM; isoform 2 precursor is encoded by transcript variant 2; hydroxyaryl-protein kinase; protein tyrosine kinase, receptor like 14; FGF receptor; fibroblast growth factor receptor BEK; tyrosylprotein kinase; K-sam protein; transmembrane protein tyrosine kinase; fibroblast growth factor receptor, BEK protein; BEK fibroblast growth factor receptor; go_component: membrane [goid 0016020] [evidence NAS] [pmid 8676562]; go_component: integral to membrane [goid 0016021] [evidence NAS]; go_component: integral to membrane [goid 0016021] [evidence NAS] [pmid 1697263]; go_function: ATP binding [goid 0005524] [evidence IEA]; go_function: heparin binding [goid 0008201] [evidence IEA]; go_function: receptor activity [goid 0004872] [evidence IEA]; go_function: nucleotide bi |
| 229547_s_at | PRKWNK2 | AI832477 | at69b10.x1 Barstead colon HPLRB7 Homo sapiens cDNA clone IMAGE: 2377243 3', mRNA sequence. |
| 209800_at | KRT16 | AF061812 | Keratin 16 (focal non-epidermolytic palmoplantar keratoderma) |
| 234411_x_at | CD44 | U94903 | CD44 antigen (homing function and Indian blood group system) |
| 222060_at | KRT8 | AI357616 | hypothetical protein LOC90133 |
| 209646_x_at | ALDH1B1 | BC001619 | Aldehyde dehydrogenase 1 family, member B1 |
| 205860_x_at | FOLH1 | NM_004476 | Folate hydrolase (prostate-specific membrane antigen) 1 |

TABLE 14-continued

Selection of tumor progenitor cell genes as CTC markers[note 1].

| Gene ID | Common | Genbank | Description |
| --- | --- | --- | --- |
| 231941_s_at | MUC20 | AB037780 | Start codon is not identified.; *Homo sapiens* mRNA for KIAA1359 protein, partial cds. |
| 208325_s_at | AKAP13 | NM_006738 | A kinase (PRKA) anchor protein 13; synonyms: BRX, LBC, HA-3, Ht31, c-lbc, AKAP-Lbc, FLJ11952, PROTO-LB, PROTO-LBC; isoform 2 is encoded by transcript variant 2; A-kinase anchoring protein; guanine nucleotide exchange factor Lbc; breast cancer nuclear receptor-binding auxiliary protein; lymphoid blast crisis oncogene; go_component: membrane fraction [goid 0005624] [evidence TAS] [pmid 9891067]; go_function: kinase activity [goid 0016301] [evidence IEA]; go_function: metal ion binding [goid 0046872] [evidence IEA]; go_function: receptor activity [goid 0004872] [evidence IEA]; go_function: diacylglycerol binding [goid 0019992] [evidence IEA]; go_function: signal transducer activity [goid 0004871] [evidence TAS] [pmid 8290273]; go_function: cAMP-dependent protein kinase activity [goid 0004691] [evidence NAS] [pmid 1618839]; go_function: guanyl-nucleotide exchange factor activity [goid 0005085] [evidence IEA]; go_function: Rho guanyl-nucleotide exchange factor activity [goid 0005089] [evidence NR]; go_process: int |
| 201650_at | KRT19 | NM_002276 | Keratin 19 |
| 219348_at | MDS032 | NM_018467 | Uncharacterized hematopoietic stem/progenitor cells protein MDS032 |
| 217078_s_at | CMRF-35H | AJ010102 | CD300A antigen |
| 204677_at | CDH5 | NM_001795 | Cadherin 5, type 2, VE-cadherin (vascular epithelium) |
| Tumor progenitor genes upregulated in >70% of cancer samples and <30% of normal samples (14) - Note 4 | | | |
| 244857_at | DTR | BE550321 | diphtheria toxin receptor (heparin-binding epidermal growth factor-like growth factor) |
| 215632_at | NEUROG2 | AF303002 | Neurogenin 2 |
| 217182_at | MUC5AC | Z34282 | *H. sapiens* (MAR11) MUC5AC mRNA for mucin (partial). |
| 207199_at | TERT | NM_003219 | Telomerase reverse transcriptase; synonyms: TP2, TRT, EST2, TCS1, hEST2; isoform 3 is encoded by transcript variant 3; telomerase catalytic subunit; go_component: nucleus [goid 0005634] [evidence IEA]; go_component: chromosome, telomeric region [goid 0000781] [evidence IC] [pmid 12135483]; go_component: telomerase holoenzyme complex [goid 0005697] [evidence IDA] [pmid 12135483]; go_function: DNA binding [goid 0003677] [evidence IEA]; go_function: RNA binding [goid 0003723] [evidence IEA]; go_function: transferase activity [goid 0016740] [evidence IEA]; go_function: telomeric DNA binding [goid 0042162] [evidence TAS] [pmid 9288757]; go_function: RNA-directed DNA polymerase activity [goid 0003964] [evidence IEA]; go_function: telomeric template RNA reverse transcriptase activity |

TABLE 14-continued

Selection of tumor progenitor cell genes as CTC markers[note 1].

| Gene ID | Common | Genbank | Description |
|---|---|---|---|
| 204100_at | THRA | NM_003250 | [goid 0003721] [evidence IEA]; go_function: telomeric template RNA reverse transcriptase activity [goid 0003721] [evidence TAS] [pmid 14991929]; go_process: telomere maintenance [goid 0000723] [evidence TAS] [pmid 12135483]; go_process: Thyroid hormone receptor, alpha (erythroblastic leukemia viral (v-erb-a) oncogene homolog, avian); synonyms: AR7, EAR7, ERBA, ERBA1, NR1A1, THRA1, THRA2, THRA3, EAR-7.1, EAR-7.2, ERB-T-1, MGC43240, c-ERBA-1, MGC000261, ERBA-ALPHA, TR-ALPHA-1, c-ERBA-ALPHA-2; isoform 1 is encoded by transcript variant 1; EAR-7.1/EAR-7.2; thyroid hormone receptor, alpha (avian erythroblastic leukemia viral (v-erb-a) oncogene homolog); thyroid hormone receptor, alpha 1; ERBA-related 7; thyroid hormone receptor, alpha-2; thyroid hormone receptor, alpha-3; triiodothyronine receptor; go_component: nucleus [goid 0005634] [evidence IEA]; go_function: zinc ion binding [goid 0008270] [evidence IEA]; go_function: metal ion binding [goid 0046872] [evidence IEA]; go_function: protein binding [goid 0005515] [evidence IPI] [pmid 10866662]; go_function: steroid hormone receptor activity [goid 0003707] [evidence IEA]; go_function: transcription factor activity [goid 0003700] [evidence TAS] [pmid 2879242]; go_function: thyroid hormone receptor |
| 223508_at | NOTCH1 | AF308602 | Notch homolog 1, translocation-associated (*Drosophila*) |
| 206759_at | FCER2 | NM_002002 | Fc fragment of IgE, low affinity II, receptor for (CD23A) |
| 210607_at | FLT3LG | U03858 | Fms-related tyrosine kinase 3 ligand |
| 210316_at | FLT4 | U43143 | Fms-related tyrosine kinase 4; synonyms: PCL, FLT41, VEGFR3; isoform 1 is encoded by transcript variant 1; fms-related tyrosine kinase-4 (vascular endothelial growth factor receptor 3); Vascular endothelial growth factor receptor 3; go_component: membrane [goid 0016020] [evidence IEA]; go_component: integral to plasma membrane [goid 0005887] [evidence TAS] [pmid 8386825]; go_function: ATP binding [goid 0005524] [evidence IEA]; go_function: receptor activity [goid 0004872] [evidence IEA]; go_function: nucleotide binding [goid 0000166] [evidence IEA]; go_function: transferase activity [goid 0016740] [evidence IEA]; go_function: protein-tyrosine kinase activity [goid 0004713] [evidence IEA]; go_function: protein serine/threonine kinase activity [goid 0004674] [evidence IEA]; go_function: vascular endothelial growth factor receptor activity [goid 0005021] |

TABLE 14-continued

Selection of tumor progenitor cell genes as CTC markers[note 1].

| Gene ID | Common | Genbank | Description |
|---|---|---|---|
| | | | [evidence IEA]; go_function: vascular endothelial growth factor receptor activity [goid 0005021] [evidence TAS] [pmid 10835628]; go_process: protein amino acid |
| 1568857_a_at | M17S2; CA125; MUC16 | BC012591 | membrane component, chromosome 17, surface marker 2 (ovarian carcinoma antigen CA125) |
| 204304_s_at | PROM1; CD133 | NM_006017 | Prominin 1; CD133; PROML1; MSTP061; RP41; AC133; CD133 was initially shown to be expressed on primitive hematopoietic stem and progenitor cells and retinoblastoma. CD133 has been shown to be expressed on hemangioblasts, and neural stem cells as well as on developing epithelium. |
| 203238_s_at | NOTCH3 | NM_000435 | Notch homolog 3 (*Drosophila*) |
| 202285_s_at | TACSTD2; GA733 | AI627697 | tumor-associated calcium signal transducer 2; GA733 antigen |
| 234720_s_at | TOB2 | AB051450 | Transducer of ERBB2, 2 |
| Genes that do not deviate between normal and cancer samples (8) - Note 5 | | | |
| 206725_x_at | BMP1 | NM_006128 | Bone morphogenetic protein 1; synonyms: TLD, PCOLC; splice variant BMP1-2; splice variant BMP-1/His isoform 2, precursor is encoded by transcript variant BMP1-2; PCP; procollagen C-endopeptidase; go_component: extracellular space [goid 0005615] [evidence IEA]; go_function: astacin activity [goid 0008533] [evidence IEA]; go_function: zinc ion binding [goid 0008270] [evidence IEA]; go_function: cytokine activity [goid 0005125] [evidence IEA]; go_function: calcium ion binding [goid 0005509] [evidence IEA]; go_function: growth factor activity [goid 0008083] [evidence IEA]; go_function: metallopeptidase activity [goid 0008237] [evidence NAS] [pmid 7798260]; go_function: procollagen C-endopeptidase activity [goid 0017026] [evidence IEA]; go_process: proteolysis [goid 0006508] [evidence IEA]; go_process: ossification [goid 0001503] [evidence IEA]; go_process: cell differentiation [goid 0030154] [evidence IEA]; go_process: cartilage condensation [goid 0001502] [evidence TAS] [pmid 3201241]; *Homo sapiens* bone morphoge |
| 202112_at | VWF | NM_000552 | Von Willebrand factor |
| 1568191_at | MCAM; CD146; MUC18 | AJ297452 | CD146; MUC18; S-ENDO; melanoma cell adhesion molecule |
| 211550_at | EGFR | AF125253 | Epidermal growth factor receptor (erythroblastic leukemia viral (v-erb-b) oncogene homolog, avian); synonyms: ERBB, mENA, ERBB1; isoform b is encoded by transcript variant 2; epidermal growth factor receptor (avian erythroblastic leukemia viral (v-erb-b) oncogene homolog); truncated epidermal growth factor receptor; cell growth inhibiting protein 40; go_component: nucleus [goid 0005634] [evidence IDA] [pmid 12828935]; |

TABLE 14-continued

Selection of tumor progenitor cell genes as CTC markers[note 1].

| Gene ID | Common | Genbank | Description |
|---|---|---|---|
|  |  |  | go_component: endosome [goid 0005768] [evidence IDA] [pmid 14702346]; go_component: plasma membrane [goid 0005886] [evidence IDA] [pmid 15465819]; go_component: integral to membrane [goid 0016021] [evidence IEA]; go_component: extracellular space [goid 0005615] [evidence NAS] [pmid 9103388]; go_component: AP-2 adaptor complex [goid 0030122] [evidence TAS] [pmid 14702346]; go_function: ATP binding [goid 0005524] [evidence IEA]; go_function: nucleotide binding [goid 0000166] [evidence IEA]; go_function: protein binding [goid 0005515] [evidence IPI] [pmid 2790960]; go_function: protein binding [goi |
| 204406_at | FLT1 | NM_002019 | Fms-related tyrosine kinase 1 (vascular endothelial growth factor/vascular permeability factor receptor) |
| 1559921_at | PECAM1; CD31 | AW138916 | platelet/endothelial cell adhesion molecule; CD31 antigen |
| 211478_s_at | DPP4; CD26 | M74777 | Dipeptidylpeptidase 4 (CD26, adenosine deaminase complexing protein 2); DPPIV |
| 209955_s_at | FAP; DPP5; seprase; APCE | U76833 | Fibroblast activation protein, alpha; seprase; DPP5; antiplasmin cleaving enzyme (APCE) |

[note 1] Only a single oligo probe from each gene that shows the best sample match, i.e., differentially regulated in cancer and normal samples.
Note 2 endogenous control genes (CD14, ITGA2, ITGB3) that do not deviate between cancer and normal samples from different individuals.
Note 3 15 tumor progenitor (TP) genes upregulated in >90% of colorectal cancer, breast cancer and ovarian cancer samples and in <10% of normal samples.
Note 4 14 tumor progenitor (TP) genes upregulated in >70% of colorectal cancer, breast cancer and ovarian cancer samples and in <30% of normal samples.
Note 5 8 genes that do not deviate between normal and cancer samples. Expression of these genes in CTCs and CECs was observed at the single-cell level.

Figure 16:
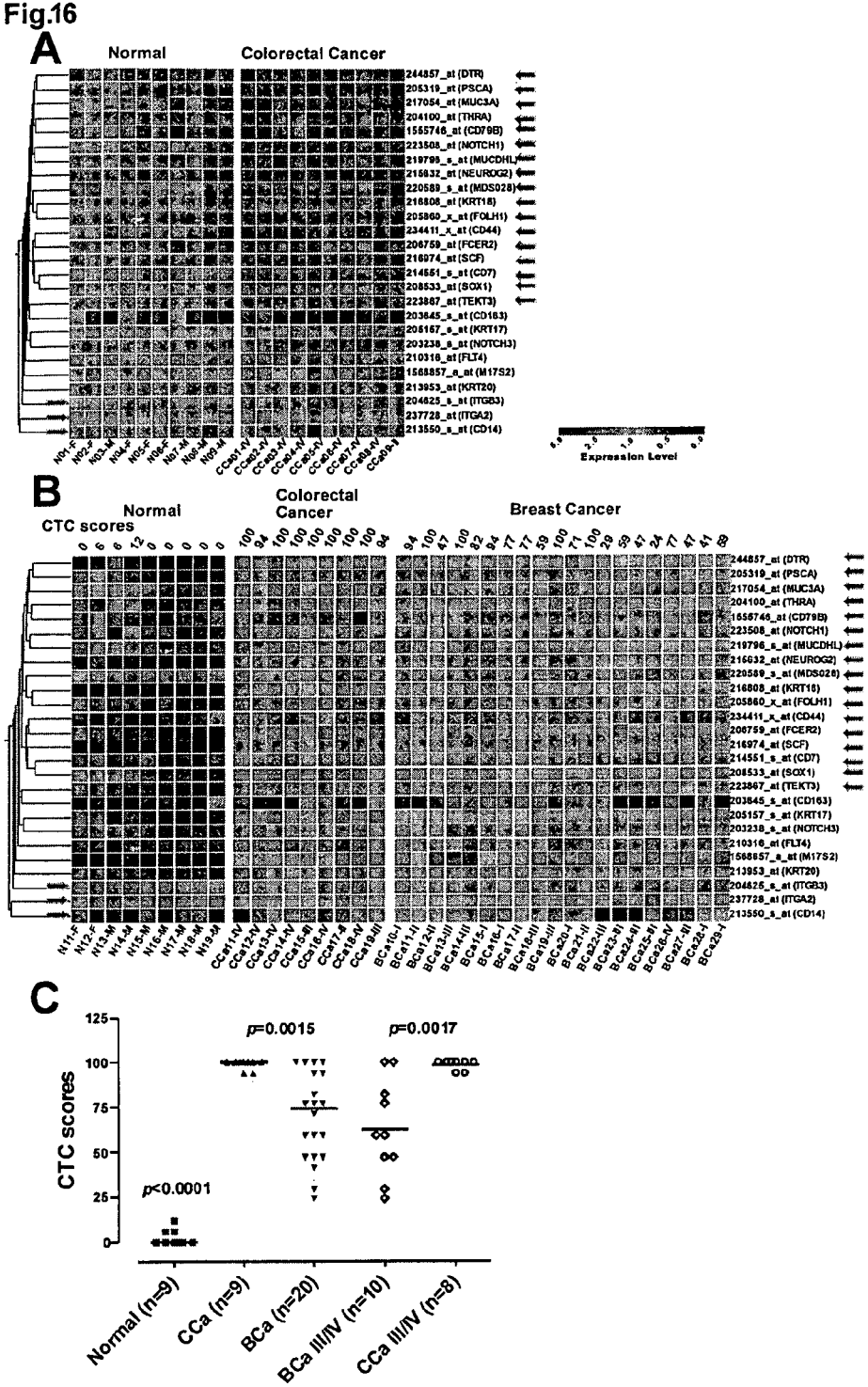
FIG. 16 shows data from nucleic acid-based blood testing for tumor-associated genes as CTC bio-markers of colorectal cancer. Colorgram depicts high (red) and low (blue) relative levels of gene expression. Green arrows point to the 17-candidate colorectal cancer CTC marker genes that were in the CTC marker gene set specific for the colorectal tumor type. Red arrows indicate the internal control genes that exhibited no difference between normal and cancer cell samples.

Colorectal CTC Identifiers. Screening of another training set of patient samples resulted in another embodiment of the invention, wherein circulating colorectal cells may be distinguished from other CTCs of epithelial origin. To determine gene expression markers that distinguish a circulating colon cancer cell from a different type of circulating cancer cell of epithelial origin, an effective reference set of circulating colon tumor cell gene markers and corresponding CTC scores were used to distinguish CTCs of patients with colon tumors from these with breast tumors using hierarchical clustering analysis of a training set that consists of 10 healthy subjects and 10 patients with colorectal cancer (FIG. 16; Table 15). A set of 17-candidate colorectal cancer CTC marker genes (DTR, PSCA, MUC3A, THRA, CD79B, NOTCH1, MUCDHL, NEUROG2, MDS028, KRT18, FOLH1, CD44, FCER2, SCF, CD7, SOX1 and TEKT3) exhibited minimal expression in the normal cell samples and significant expression in the cell samples of colorectal cancer (FIG. 16A; Table 15). Another set of 6-tumor associated marker genes (CD163, KRT17, NOTCH3, FLT4, M17S2 and KRT20) expressed at various levels in the normal cell samples and in the cell samples of colorectal cancer, and tended to cluster with internal control genes (ITGA2, CD14 and ITGB3) (FIG. 16A). The validation of the 17-gene set is discussed in Example 3.

TABLE 6

Selection of tumor-associated genes for CTC markers of patients with colorectal cancer[note 1].

| Gene ID | Common | Genbank | Description |
|---|---|---|---|
| Internal control genes (3)[Note 2] | | | |
| 237728_at | ITGA2 | AI733222 | integrin, alpha 2 (CD49B, alpha 2 subunit of VLA-2 receptor) |
| 213550_s_at | CD14 | AA993683 | CD14 antigen |
| 204625_s_at | ITGB3 | BF115658 | integrin, beta 3 (platelet glycoprotein IIIa, antigen CD61) |

TABLE 6-continued

Selection of tumor-associated genes for CTC markers of patients with colorectal cancer[note 1].

| Gene ID | Common | Genbank | Description |
|---|---|---|---|

Tumor-associated genes upregulated in CTCs of patients with colorectal cancer (17)[Note 3]

| Gene ID | Common | Genbank | Description |
|---|---|---|---|
| 244857_at | DTR | BE550321 | diphtheria toxin receptor (heparin-binding epidermal growth factor-like growth factor) |
| 205319_at | PSCA | NM_005672 | Prostate stem cell antigen |
| 217054_at | MUC3A | AF007194 | mucin 3B |
| 204100_at | THRA | NM_003250 | Thyroid hormone receptor, alpha (erythroblastic leukemia viral (v-erb-a) oncogene homolog, avian); synonyms: AR7, EAR7, ERBA, ERBA1, NR1A1, THRA1, THRA2, THRA3, EAR-7.1, EAR-7.2, ERB-T-1, MGC43240, c-ERBA-1, MGC000261, ERBA-ALPHA, TR-ALPHA-1, c-ERBA-ALPHA-2; isoform 1 is encoded by transcript variant 1; EAR-7.1/EAR-7.2; thyroid hormone receptor, alpha (avian erythroblastic leukemia viral (v-erb-a) oncogene homolog); thyroid hormone receptor, alpha 1; ERBA-related 7; thyroid hormone receptor, alpha-2; thyroid hormone receptor, alpha-3; triiodothyronine receptor; go_component: nucleus [goid 0005634] [evidence IEA]; go_function: zinc ion binding [goid 0008270] [evidence IEA]; go_function: metal ion binding [goid 0046872] [evidence IEA]; go_function: protein binding [goid 0005515] [evidence IPI] [pmid 10866662]; go_function: steroid hormone receptor activity [goid 0003707] [evidence IEA]; go_function: transcription factor activity [goid 0003700] [evidence TAS] [pmid 2879242]; go_function: thyroid hormone receptor |
| 1555746_at | CD79B | BC030210 | CD79B antigen (immunoglobulin-associated beta); synonyms: B29, IGB; isoform 2 precursor is encoded by transcript variant 2; B-cell-specific glycoprotein B29; immunoglobulin-associated protein (B29); go_component: membrane [goid 0016020] [evidence IEA]; go_component: integral to plasma membrane [goid 0005887] [evidence TAS] [pmid 8486355]; go_function: transmembrane receptor activity [goid 0004888] [evidence IEA]; go_process: immune response [goid 0006955] [evidence TAS] [pmid 8486355]; go_process: cell surface receptor linked signal transduction [goid 0007166] [evidence IEA]; Homo sapiens CD79B antigen (immunoglobulin-associated beta) (CD79B), transcript variant 2, mRNA. |
| 223508_at | NOTCH1 | AF308602 | Notch homolog 1, translocation-associated (Drosophila) |
| 219796_s_at | MUCDHL | NM_021924 | Mucin and cadherin-like; synonyms: MU-PCDH, FLJ20219; isoform 1 is encoded by transcript variant 1; mucin and cadherin-like protein; MUCDHL-FL; MUCDHL-ALT; go_component: membrane [goid 0016020] [evidence NAS]; go_component: integral to membrane [goid 0016021] [evidence ISS]; go_function: protein binding [goid 0005515] [evidence IEA]; go_function: calcium ion binding [goid 0005509] [evidence ISS]; go_process: cell adhesion [goid 0007155] [evidence ISS]; go_process: homophilic cell adhesion [goid 0007156] [evidence IEA]; go_process: calcium-dependent cell-cell adhesion [goid 0016339] [evidence NAS]; Homo sapiens mucin and cadherin-like (MUCDHL), transcript variant 1, mRNA.; isoform 3 is encoded by transcript variant 3; Homo sapiens mucin and cadherin-like (MUCDHL), transcript variant 3, mRNA.; isoform 4 is encoded by transcript variant 4; Homo sapiens mucin and cadherin-like (MUCDHL), transcript variant 4, mRNA. |
| 215632_at | NEUROG2 | AF303002 | Neurogenin 2 |
| 220589_s_at | MDS028 | NM_018463 | Uncharacterized hematopoietic stem/progenitor cells protein MDS028 |
| 216808_at | KRT18 | AL354915 | |
| 205860_x_at | FOLH1 | NM_004476 | Folate hydrolase (prostate-specific membrane antigen) 1 |
| 234411_x_at | CD44 | U94903 | CD44 antigen (homing function and Indian blood group system) |

TABLE 6-continued

Selection of tumor-associated genes for CTC markers of patients with colorectal cancer[note 1].

| Gene ID | Common | Genbank | Description |
|---|---|---|---|
| 206759_at | FCER2 | NM_002002 | Fc fragment of IgE, low affinity II, receptor for (CD23A) |
| 216974_at | SCF | S80491 | Stem cell factor {alternatively spliced} [human, preimplantation embryos, blastocysts, mRNA Partial, 180 nt] |
| 214551_s_at | CD7 | NM_006137 | CD7 antigen (p41) |
| 208533_at | SOX1 | NM_005986 | SRY (sex determining region Y)-box 1 |
| 223867_at | TEKT3 | AF334676 | Tektin 3 |
| Tumor-associated genes in CTCs of patients with other types of cancer (6)[Note 4] | | | |
| 203645_s_at | CD163 | NM_004244 | CD163 antigen; synonyms: M130, MM130; isoform b is encoded by transcript variant 2; macrophage-associated antigen; go_component: membrane [goid 0016020] [evidence IEA]; go_component: extracellular region [goid 0005576] [evidence NAS]; go_component: integral to plasma membrane [goid 0005887] [evidence TAS] [pmid 8370408]; go_function: scavenger receptor activity [goid 0005044] [evidence NAS] [pmid 8370408]; go_function: scavenger receptor activity [goid 0005044] [evidence TAS] [pmid 8370408]; go_process: antimicrobial humoral response (sensu Vertebrata) [goid 0019735] [evidence TAS] [pmid 8370408]; *Homo sapiens* CD163 antigen (CD163), transcript variant 2, mRNA. |
| 205157_s_at | KRT17 | NM_000422 | Keratin 17 |
| 203238_s_at | NOTCH3 | NM_000435 | Notch homolog 3 (*Drosophila*) |
| 210316_at | FLT4 | U43143 | Fms-related tyrosine kinase 4; synonyms: PCL, FLT41, VEGFR3; isoform 1 is encoded by transcript variant 1; fms-related tyrosine kinase-4 (vascular endothelial growth factor receptor 3); Vascular endothelial growth factor receptor 3; go_component: membrane [goid 0016020] [evidence IEA]; go_component: integral to plasma membrane [goid 0005887] [evidence TAS] [pmid 8386825]; go_function: ATP binding [goid 0005524] [evidence IEA]; go_function: receptor activity [goid 0004872] [evidence IEA]; go_function: nucleotide binding [goid 0000166] [evidence IEA]; go_function: transferase activity [goid 0016740] [evidence IEA]; go_function: protein-tyrosine kinase activity [goid 0004713] [evidence IEA]; go_function: protein serine/threonine kinase activity [goid 0004674] [evidence IEA]; go_function: vascular endothelial growth factor receptor activity [goid 0005021] [evidence IEA]; go_function: vascular endothelial growth factor receptor activity [goid 0005021] [evidence TAS] [pmid 10835628]; go_process: protein amino acid |
| 1568857_a_at | M17S2 | BC012591 | membrane component, chromosome 17, surface marker 2 (ovarian carcinoma antigen CA125) |
| 213953_at | KRT20 | AI732381 | keratin 20 | note 1 Only a single oligo probe from each gene that shows the best gene match, upregulated in tumor cells and downregulated in normal cells from >80% of all samples was shown.
Note 2 endogenous control genes (CD14, ITGA2, ITGB3) that do not deviate between tumor and normal cells from different individuals were used to assist sorting upregulated tumor-associated genes in CTCs.
Note 3 17 tumor-associated genes upregulated in colorectal cancer.
Note 4 6 tumor-associated genes upregulated in other types of cancer.

Cell-based diagnostic kit. In another aspect, the invention is embodied in a kit useful for detecting CTCs in patients having or suspected of having a cancer of epithelial origin. The proclivity of a tumor cell to invade collagenous matrices is one of the hallmarks of metastatic cells (Friedl and Wolf, 2003; Mareel and Leroy, 2003; Chen, 1989; Coopman et al., 1996; Mueller and Chen, 1991; Chen et al., 1985). Thus, the preferred detection method for CTCs involves: rare cell enrichment from patients' blood by CAM, and co-localization of at least two of the tumor progenitor cell markers described above. Preferably, colocalization is accomplished using antibodies against the markers. The CTCs can then be validated for cell invasiveness by assessment of cellular ability to locally ingest the collagenous substrata. The CTC detection method and associated reagent kits are intended for cell-based assays including microscopy and flow cytometry.

To effectively detect a CTC, at least two preferred CTC markers can be selected from the CTC markers described in Tables I-VII: at least one marker can be selected from the candidate tumor progenitor marker genes (MUC4, FGFR2, PRKWNK2, MUC5AC, KRT16, TERT, KRT8, ALDH1B1, CMRF-35H, CDH5, MDS032, FLT3LG, MUC20, AKAP13 and KRT19) and another one can be from the progenitor cell marker genes (TACSTD2, PROM1, VWF, MCAM, PECAM1, DTR, PSCA, MUC3A, THRA, CD79B, NOTCH1, MUCDHL, NEUROG2, MDS028, KRT18, FOLH1, CD44, FCER2, SCF, CD7, SOX1, TEKT3, CD163, KRT17, NOTCH3, FLT4, MI 7S2, KRT20, FLT4, DTR, FOLH1, NEUROG2, FLT3LG, TEK, NOTCH3, DPP4, FAP, SORT1, BMP1, FLT1, FGF4, FGF5, FGF6, FGFR1, EGFR, SOX2, CDC2, NRG1, and NAALAD2).

Antibodies directed against protein products of the CTC progenitor gene markers are currently available and can be purchased through various companies. For examples, antibodies against protein products of CDH5, MUC4, MUC5AC, MUC16, TERT, FGFR2, FLT3LG, AKAP13, TACSTD2, PROM1, VWF, MCAM, PECAM1, KRT8, KRT16 and KRT19 genes can be purchase from Santo Cruz Biotech., CA, Abcam Inc., BD Biosciences, Beckman Coulter, and Dako. Useful antibodies are: fluorescein-anti-VWF antibodies (US Biological, Swampscott, Mass.); antibodies against EpCAM/TACSTD2 (Dako, Carpinteria, Calif.); antibodies against pan cytokeratins (Sigma, St. Louis, Mo.); antibodies against ESA (Biomeda, Foster City, Calif.); carcinoembryonic antigen (CEA, clone 11-7, Dako, Carpinteria, Calif.), antibodies against DPP4 and FAP proteins (Vitatex Inc. N.Y.). In some instances, the cells can be co-stained with Hoechst 33342 dye (Invitrogen, Carlsbad, Calif.) to label available DNA of the cell. CAM-captured cells have been shown to be >99.9% viable using the Molecular Probes LIVE/DEAD Viability Kit #4 (Invitrogen, Carlsbad, Calif.: dead cells stain with ethidium homodimer-1 exhibit give red fluorescence, whereas live cells stain with calcein AM and exhibit green fluorescence).

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.)

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. In other embodiments, the immunoassay described in U.S. Pat. Nos. 5,599,677 and 5,672,480, each of which is herein incorporated by reference, may be used. An example of above-described method is summarized in Example 4.

Endothelial progenitor cell identifiers. The applicant has provided another embodiment of the invention by screening still another set of patient samples for markers distinctive for CECs. To identify endothelial genes that are upregulated in CECs and CTCs, microarray analysis was performed using RNA extracted from CAM bound cells of a training set that consists of 10 healthy donors (containing >100 CD31+ cells/mL blood) in comparison with the RNA extracted from CAM bound cells of 10 colon cancer patients (containing >100 CD31+ and >100 CK+ cells/mL blood) (FIG. 18A). Selected genes were cross-examined using 7 normal samples (2 were new) and 9 breast cancer samples (FIG. 18B), as well as 5 normal samples and 5 ovarian cancer samples (FIG. 18B). Resulting gene markers that were upregulated in normal and cancer samples were then validated using a testing set that consists of 9 normal samples, 9 colorectal cancer samples and 20 breast cancer samples (FIG. 19A-B).

Figure 12:
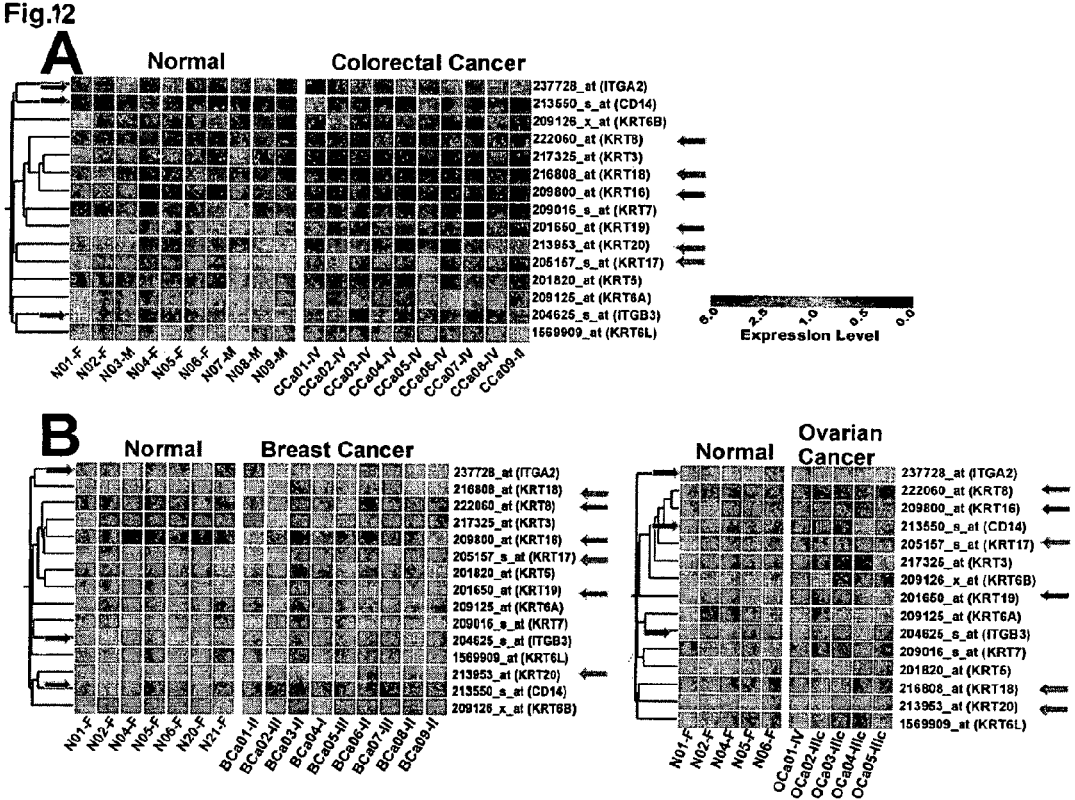
FIG. 12 shows the KRT and internal control genes associated with circulating tumor cells isolated by CAM. A set of candidate KRT marker genes (KRT8, KRT16, KRT19, KRT17, KRT18 and KRT20) exhibited minimal expression in the normal cell samples and significant expression in the colorectal cancer cell samples.

Among 29 genes known to be expressed in the cell of the endothelial lineage, a set of 13 endothelial genes were found to be upregulated in normal blood samples and a set of 12 endothelial genes were found to be upregulated in cancer blood samples (FIGS. 18 & 19; Table 16). In addition, CAM-enriched cells allowed the determination of internal marker controls (CD14 and integrins) that are necessary for cellular and molecular analyses of blood-borne cellular samples from subjects (FIG. 12). FIG. 16A-B and Table 16 show a set of 12-CDH5 endothelial marker genes (CDH5, FLT4, FGFR2, DTR, FOLH1, NEUROG2, FLT3LG, TEKT3, SOX1, NOTCH1, NOTCH3 and DPP4) that exhibited downregulated expression in the normal cell samples and significantly upregulated expression in the cell samples of colorectal, breast and ovarian cancer, indicating that these genes express at higher levels in CTCs than CECs. Another set of 13-CD31 endothelial cell marker genes (CD31/PECAM1, VWF, MCAM, BMP1, FLT1, FGF4, FGF5, FGF6, FGFR1, EGFR, SOX2, CDC2 and NRG1) exhibited significantly upregulated expression in the normal cell samples and downregulated expression in the cell samples of colorectal, breast and ovarian cancer (FIG. 18A-B and Table 16), indicating that these genes express in both CECs and CTCs. The majority of >1,000 genes known to be involved in stem cells and the developmental endothelial cell lineage, i.e., TEK, NAALAD2, FAP and SORT1 (Table 16), showed minimal differences between CAM-enriched cellular samples from cancer patients and healthy donors. This finding indicates that the selected 29 endothelial lineage genes are of progenitor cell markers, among which the 12-genes including CDH5 et al could be potential markers for CTCs common to the three cancer types and any one of this gene set can be used in sorting of cancer progenitor cells from normal endothelial progenitor cells present in the circulation.

Using the percentage of genes matching the 13-CD31 endothelial genes as the CEC score of a sample, significant differences of the mean±standard error CEC scores in normal and cancer samples were found: 96.44±1.41 CEC scores in normal and 32.14±3.87 CEC scores in cancer (FIG. 19A-B, p-value<0.0001). This result confirms the suggestion that the 13-endothelial cell marker genes (CD31/PECAM1, VWF, MCAM, BMP1, FLT1, FGF4, FGF5, FGF6, FGFR1, EGFR, SOX2, CDC2 and NRG1) express in both CECs and CTCs. Using the percentage of genes matching the 12-CDH5 endothelial genes as the CTC score of a sample, significant differences of the CTC scores in normal control and cancer samples were also found: 1.78±1.18 CTC scores in normal and 83.34±2.81 CTC scores in cancer (FIG. 19A-B, p-value<0.0001). These data further indicate that the 12-CDH5 endothelial cell marker genes (CDH5, FLT4, FGFR2, DTR, FOLH1, NEUROG2, FLT3LG, TEKT3, SOX1, NOTCH1, NOTCH3 and DPP4) express in both CECs and CTCs. The GEP comparison identifies the CEC and CTC endothelial progenitor genes in cells recovered from blood using CAM (Table 16), although it does not provide specific markers for individual CECs and CTCs due to the co-isolation of both cell types from cancer samples.

TABLE 16

Endothelial lineage genes upregulated in CAM-enriched CECs and CTCs[note 1].

| Gene ID | Common | Genbank | Description |
|---|---|---|---|
| | | | Internal control genes[note 2] |
| 237728_at | ITGA2 | AI733222 | integrin, alpha 2 (CD49B, alpha 2 subunit of VLA-2 receptor) |
| 213550_s_at | CD14 | AA993683 | CD14 antigen |
| 204625_s_at | ITGB3 | BF115658 | integrin, beta 3 (platelet glycoprotein IIIa, antigen CD61) |
| | | | Endothelial lineage genes upregulated in CECs (13)[note 3] |
| 1559921_at | PECAM1 | AW138916 | CD31 antigen; platelet/endothelial cell adhesion molecule |
| 202112_at | VWF | NM_000552 | Von Willebrand factor |
| 1568191_at | MCAM | AJ297452 | CD146; MUC18; S-ENDO; melanoma cell adhesion molecule |
| 206725_x_at | BMP1 | NM_006128 | Bone morphogenetic protein 1; synonyms: TLD, PCOLC; splice variant BMP1-2; splice variant BMP-1/His isoform 2, precursor is encoded by transcript variant BMP1-2; PCP; procollagen C-endopeptidase; go_component: extracellular space [goid 0005615] [evidence IEA]; go_function: astacin activity [goid 0008533] [evidence IEA]; go_function: zinc ion binding [goid 0008270] [evidence IEA]; go_function: cytokine activity [goid 0005125] [evidence IEA]; go_function: calcium ion binding [goid 0005509] [evidence IEA]; go_function: growth factor activity [goid 0008083] [evidence IEA]; go_function: metallopeptidase activity [goid 0008237] [evidence NAS] [pmid 7798260]; go_function: procollagen C-endopeptidase activity [goid 0017026] [evidence IEA]; go_process: proteolysis [goid 0006508] [evidence IEA]; go_process: ossification [goid 0001503] [evidence IEA]; go_process: cell differentiation [goid 0030154] [evidence IEA]; go_process: cartilage condensation [goid 0001502] [evidence TAS] [pmid 3201241]; Homo sapiens bone morphoge |
| 204406_at | FLT1 | NM_002019 | Fms-related tyrosine kinase 1 (vascular endothelial growth factor/vascular permeability factor receptor) |
| 1552982_a_at | FGF4 | NM_002007 | Fibroblast growth factor 4 (heparin secretory transforming protein 1, Kaposi sarcoma oncogene) |
| 208378_x_at | FGF5 | NM_004464 | Fibroblast growth factor 5; synonyms: HBGF-5, Smag-82; isoform 2 precursor is encoded by transcript variant 2; heparin-binding growth factor 5; go_component: extracellular space [goid 0005615] [evidence TAS] [pmid 9786939]; go_function: growth factor activity [goid 0008083] [evidence IEA]; go_process: cell proliferation [goid 0008283] [evidence TAS] [pmid 3211147]; go_process: cell-cell signaling [goid 0007267] [evidence TAS] [pmid 9786939]; go_process: nervous system development [goid 0007399] [evidence TAS] [pmid 9786939]; go_process: regulation of progression through cell cycle [goid 0000074] [evidence IEA]; go_process: fibroblast growth factor receptor signaling pathway [goid 0008543] [evidence TAS] [pmid 9786939]; Homo sapiens fibroblast growth factor 5 (FGF5), transcript variant 2, mRNA. |
| 208417_at | FGF6 | NM_020996 | Fibroblast growth factor 6 |
| 207937_x_at | FGFR1 | NM_023110 | Fibroblast growth factor receptor 1 (fms-related tyrosine kinase 2, Pfeiffer syndrome); synonyms: H2, H3, H4, H5, CEK, FLG, FLT2, KAL2, BFGFR, C-FGR, N-SAM; isoform 2 precursor is encoded by transcript variant 2; hydroxyaryl-protein kinase; fms-related tyrosine kinase-2; heparin-binding growth factor receptor; FMS-like tyrosine kinase 2; basic fibroblast growth factor receptor 1; protein-tyrosine kinase; N-sam tyrosine kinase; tyrosylprotein kinase; go_component: membrane fraction [goid 0005624] [evidence NAS]; go_component: integral to plasma membrane [goid 0005887] [evidence TAS] [pmid 10918587]; go_function: ATP binding [goid 0005524] [evidence IEA]; go_function: ATP binding [goid 0005524] [evidence NAS]; go_function: heparin binding [goid 0008201] [evidence NAS]; go_function: receptor activity [goid 0004872] [evidence IEA]; go_function: nucleotide binding [goid 0000166] [evidence [IEA]; go_function: protein binding [goid 0005515] [evidence IPI] [pmid 9660748]; go_function: transferase activity [goid 001674 |
| 211550_at | EGFR | AF125253 | Epidermal growth factor receptor (erythroblastic leukemia viral (v-erb-b) oncogene homolog, avian); synonyms: ERBB, mENA, ERBB1; isoform b is encoded by transcript variant 2; epidermal growth factor receptor (avian erythroblastic leukemia viral (v-erb-b) oncogene homolog); truncated epidermal growth factor receptor; cell growth inhibiting |

TABLE 16-continued

Endothelial lineage genes upregulated in CAM-enriched CECs and CTCs[note 1].

| Gene ID | Common | Genbank | Description |
|---|---|---|---|
| | | | protein 40; go_component: nucleus [goid 0005634] [evidence IDA] [pmid 12828935]; go_component: endosome [goid 0005768] [evidence IDA] [pmid 14702346]; go_component: plasma membrane [goid 0005886] [evidence IDA] [pmid 15465819]; go_component: integral to membrane [goid 0016021] [evidence IEA]; go_component: extracellular space [goid 0005615] [evidence NAS] [pmid 9103388]; go_component: AP-2 adaptor complex [goid 0030122] [evidence TAS] [pmid 14702346]; go_function: ATP binding [goid 0005524] [evidence IEA]; go_function: nucleotide binding [goid 0000166] [evidence IEA]; go_function: protein binding [goid 0005515] [evidence IPI] [pmid 2790960]; go_function: protein binding [goi |
| 214178_s_at | SOX2 | AI356682 | SRY (sex determining region Y)-box 2 |
| 210559_s_at | CDC2 | D88357 | Cell division cycle 2, G1 to S and G2 to M; synonyms: CDK1, MGC111195, DKFZp686L20222; isoform 2 is encoded by transcript variant 2; cell division control protein 2 homolog; cyclin-dependent kinase 1; p34 protein kinase; cell cycle controller CDC2; go_component: nucleus [goid 0005634] [evidence TAS] [pmid 10767298]; go_function: ATP binding [goid 0005524] [evidence IEA]; go_function: nucleotide binding [goid 0000166] [evidence IEA]; go_function: protein binding [goid 0005515] [evidence IPI] [pmid 9001210]; go_function: protein binding [goid 0005515] [evidence IPI] [pmid 9988268]; go_function: transferase activity [goid 0016740] [evidence IEA]; go_function: cyclin-dependent protein kinase activity [goid 0004693] [evidence NR]; go_process: mitosis [goid 0007067] [evidence IEA]; go_process: cell division [goid 0051301] [evidence IEA]; go_process: protein amino acid phosphorylation [goid 0006468] [evidence IEA]; go_process: regulation of progression through cell cycle [goid 0000074] [evidence NAS] [pmid 10825186] |
| 208241_at | NRG1 | NM_004495 | Neuregulin 1; synonyms: GGF, HGL, HRG, NDF, ARIA, GGF2, HRG1, HRGA, SMDF; isoform HRG-beta1 is encoded by transcript variant HRG-beta1; heregulin, alpha (45 kD, ERBB2 p185-activator); glial growth factor; neu differentiation factor; sensory and motor neuron derived factor; go_component: membrane [goid 0016020] [evidence NAS]; go_component: membrane [goid 0016020] [evidence NAS] [pmid 8096067]; go_component: integral to membrane [goid 0016021] [evidence IEA]; go_component: extracellular region [goid 0005576] [evidence NAS] [pmid 1348215]; go_component: extracellular region [goid 0005576] [evidence NAS] [pmid 1350381]; go_component: extracellular region [goid 0005576] [evidence NAS] [pmid 8096067]; go_function: receptor binding [goid 0005102] [evidence IEA]; go_function: growth factor activity [goid 0008083] [evidence IEA]; go_function: growth factor activity [goid 0008083] [evidence NAS] [pmid 8096067]; go_function: transcription cofactor activity [goid 0003712] [evidence IDA] [pmid 15073182]; go_function: rece |
| not validated: | | | |
| 206702_at | TEK | NM_000459 | TEK tyrosine kinase, endothelial (venous malformations, multiple cutaneous and mucosal) |
| 1554506_x_at | NAALAD2 | BC038840 | N-acetylated alpha-linked acidic dipeptidase 2 |

Endothelial lineage genes upregulated in CTCs (12)[note 4]

| Gene ID | Common | Genbank | Description |
|---|---|---|---|
| 204677_at | CDH5 | NM_001795 | Cadherin 5, type 2, VE-cadherin (vascular epithelium) |
| 210316_at | FLT4 | U43143 | Fms-related tyrosine kinase 4; synonyms: PCL, FLT41, VEGFR3; isoform 1 is encoded by transcript variant 1; fms-related tyrosine kinase-4 (vascular endothelial growth factor receptor 3); Vascular endothelial growth factor receptor 3; go_component: membrane [goid 0016020] [evidence IEA]; go_component: integral to plasma membrane [goid 0005887] [evidence TAS] [pmid 8386825]; go_function: ATP binding [goid 0005524] [evidence IEA]; go_function: receptor activity [goid 0004872] [evidence IEA]; go_function: nucleotide binding [goid 0000166] [evidence IEA]; go_function: transferase activity [goid 0016740] [evidence IEA]; go_function: protein-tyrosine kinase activity [goid 0004713] [evidence IEA]; go_function: protein serine/threonine kinase activity [goid 0004674] [evidence |

TABLE 16-continued

Endothelial lineage genes upregulated in CAM-enriched CECs and CTCs[note 1].

| Gene ID | Common | Genbank | Description |
|---|---|---|---|
| | | | IEA]; go_function: vascular endothelial growth factor receptor activity [goid 0005021] [evidence IEA]; go_function: vascular endothelial growth factor receptor activity [goid 0005021] [evidence TAS] [pmid 10835628]; go_process: protein amino acid |
| 211399_at | FGFR2 | AB030077 | Fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome); synonyms: BEK, JWS, CEK3, CFD1, ECT1, KGFR, TK14, TK25, BFR-1, K-SAM; isoform 2 precursor is encoded by transcript variant 2; hydroxyaryl-protein kinase; protein tyrosine kinase, receptor like 14; FGF receptor; fibroblast growth factor receptor BEK; tyrosylprotein kinase; K-sam protein; transmembrane protein tyrosine kinase; fibroblast growth factor receptor, BEK protein; BEK fibroblast growth factor receptor; go_component: membrane [goid 0016020] [evidence NAS] [pmid 8676562]; go_component: integral to membrane [goid 0016021] [evidence NAS]; go_component: integral to membrane [goid 0016021] [evidence NAS] [pmid 1697263]; go_function: ATP binding [goid 0005524] [evidence IEA]; go_function: heparin binding [goid 0008201] [evidence IEA]; go_function: receptor activity [goid 0004872] [evidence IEA]; go_function: nucleotide bi |
| 244857_at | DTR | BE550321 | diphtheria toxin receptor (heparin-binding epidermal growth factor-like growth factor) |
| 205860_x_at | FOLH1 | NM_004476 | Folate hydrolase (prostate-specific membrane antigen) 1 |
| 215632_at | NEUROG2 | AF303002 | Neurogenin 2 |
| 210607_at | FLT3LG | U03858 | Fms-related tyrosine kinase 3 ligand |
| 223867_at | TEKT3 | AF334676 | Tektin 3 |
| 208533_at | SOX1 | NM_005986 | SRY (sex determining region Y)-box 1 |
| 223508_at | NOTCH1 | AF308602 | Notch homolog 1, translocation-associated (*Drosophila*) |
| 203238_s_at | NOTCH3 | NM_000435 | Notch homolog 3 (*Drosophila*) |
| 211478_s_at | DPP4 | M74777 | Dipeptidylpeptidase 4 (CD26, adenosine deaminase complexing protein 2); DPPIV |
| not validated: | | | |
| 209955_s_at | FAP | U76833 | Fibroblast activation protein, alpha; seprase; DPP5; antiplasmin cleaving enzyme (APCE) |
| 212807_s_at | SORT1 | BF447105 | sortilin 1 |

[note 1] Only a single oligo probe from each gene that shows the best gene match, up-regulated in tumor cells and down-regulated in normal cells from >80% of all subjects, is presented.
[note 2] endogenous control genes (CD14, ITGA2, ITGB3) that do not deviate between tumor and normal cells from different individuals were used to assist sorting up-regulated tumor-associated genes in CTCs.
[note 3] 13 out of 15 endothelial lineage genes (except TEK and NAALAD2) were validated in FIG. 9A; the 13 upregulated genes in normal samples were used to calculate the CEC score of a sample.
[note 4] 12 out of 14 endothelial lineage genes (except SORT1 and FAP) were validated in FIG. 9A; the 12 genes were used to calculate the CTC score of a sample.

CEC/CTC discrimination. GEP of cells isolated by CAM from the blood (FIGS. 18 & 19) indicates that CTCs express both epithelial and endothelial progenitor markers. Methods were established to discriminate CTCs from CECs using cell-based molecular analyses, including florescence microscopic imaging and flow cytometry. To identify CECs, CAM-isolated cells were immuno-phenotyped using antibodies against gene products selected from the 13-CD31 endothelial genes (Table 16), in combination with a cellular function specific for endothelial progenitor cells (uptake of fluorescein-acetylated low density lipoprotein, acLDL) (Asahara et al., 1997). In addition to recognizing the cell with the endothelial progenitor markers and the functional evidence, CTCs were identified by immuno-phenotyping using antibodies against gene products selected from the epithelial lineage genes (Table 14) and the 12-CDH5 endothelial genes (Table 16), in combination with observing a cellular function specific for invasive tumor cells (ingestion of extracellular CAM).

To determine the phenotype of CECs and CTCs, a mononucleate cell (MNC) fraction (obtained by Ficoll Paque density gradient centrifugation) from 0.5 ml whole blood aliquots was seeded onto one well of a red fluorescent CAM-coated 16-well chamber slide (Vita-Assay™, Vitatex Inc., Stony Brook, N.Y.) and 0.1 μg/mL of fluorescein-conjugated acLDL (Invitrogen) was added into the culture. Cells were incubated for 12-18 hours to label the cells in vitro. This step labels tumor cells by making use of their ability to ingest red fluorescent CAM fragments, and endothelial cells by uptake of acLDL. Cells were then fixed with 3.5% paraformaldehyde/PBS, permeabilized with 0.1% Triton X-100, and subsequently immuno-stained using a mixture of green fluorescent antibodies against CD31 (Dynal, Lake Success), CDH5, KRT8 (Santa Cruz Biotechnology, Inc., Santa Cruz, Calif.) or an anti-CD45 antibody (clone T29/33, DakoCytomation, Carpinteria, Calif.) and followed by red color alkaline-phosphatase-anti-alkaline-phosphatase (APAAP) conjugated secondary antibodies (DakoCytomation, Carpinteria, Calif.). CD45 antibody staining was used for internal control of cells with common leukocyte markers and normalization of fluorescence signal. A Nikon E-400 inverted fluorescence microscope equipped with a Microfire digital camera system and Image Pro Plus software were used to examine and analyze the image results.

Functional assays and immuno-phenotyping of CAM-isolated cells from blood samples of a healthy donor and a patient with colon cancer shows CD31+/acLDL+/CAM− or CDH5+/acLDL+/CAM− cells being CECs (FIG. 20, upper three panels, open arrows). CD31+/acLDL+/CAM+, CDH5+/acLDL+/CAM+, KRT8+/acLDL+/CAM+ or CD45−/acLDL+/CAM+ large (>12 μm in diameter) cells in blood samples of a patient with colon cancer were identified as CTCs (FIG. 20, lower four panels, single or double arrows). The preferred method of detecting CTCs is to identify CDH5+/acLDL+/CAM+ or KRT8+/acLDL+/CAM+ large cells (FIG. 20).

The method for discriminating CECs from CTCs is used, as described in Example 5, to isolate and detect CECs and CTCs in peripheral blood.

EXAMPLES

Example 1

Gene Expression Signatures of Metastatic Tumor Cells in Blood of Patients with Malignant Solid Tumors Patients and Healthy Blood Donors. Prior to treatment, cancer patients, including patients with colorectal and breast cancers, as well as healthy individuals were admitted to the study after written, informed consent was obtained. Fresh blood samples and relevant pathological data were obtained from the Stony Brook University Medical Center and the Veteran Administration Medical Center at Northport, N.Y., respectively. The clinical follow-up data included tumor type and stage, as assessed by the treating physician.

Blood Sample Preparation. Between 4 to 16 ml (median=8 ml) of peripheral blood were collected in Vacutainer™ tubes (Becton Dickinson, Franklin Lakes, N.J.; green top, lithium heparin as anticoagulant). Blood samples were delivered to the laboratory at room temperature within one to four hours from collection, and processed immediately. The CAM-initiated rare cell enrichment involves two basic methods. One-step CAM method (Vita-Cap™, Vitatex Inc., Stony Brook, N.Y.): Cell samples were transferred into a CAM-coated tube, Vita-Cap™, and incubated for three hours at 37° C. while rotating at 10 rpm to imitate blood flow and maximize the contact between cells and the CAM substrate. The tubes were washed with warm media to remove non-adherent cells (as CAM⁻ cells not captured by CAM). RNA of CAM-bound cells was extracted for Affymetrix DNA microarray and q-PCR analyses. Two-step CAM method (Vita-Assay™, Vitatex Inc., Stony Brook, N.Y.): Cell samples were subjected to density gradient centrifugation to obtain the nucleated cells containing potential tumor cells, which were then seeded onto a 16-well chamber slide or 96-well microtiter plate coated with CAM containing fluorescently labeled type I collagen films. After culturing for 12 hours, the non-adherent cells were washed away, and the remaining cells were either extracted for RNA preparations.

GEP and bioinformatic analysis. Total RNAs of the cells adherent to CAM or antibody-coated solid supports were purified by RNeasy® Mini Kit (Qiagen, Valencia, Calif.) and then subjected to DNA microarraying. Generation of cRNA, labelling, hybridization, and scanning of the Affymetrix high-density oligonucleotide microarray chip (Hu133A, 22,283 probe sets or Hu133A 2.0 chip) according to the manufacturer's specifications (Affymetrix, Santa Clara, Calif.). Analysis of each chip was performed using the Affymetrix Microarray Suite 5.1 Software to generate raw expression data. GeneSpring 7.2 software (Silicon Genetics, Redwood City, Calif.) was used to perform statistical analysis and investigate the variation in gene expression. Bioinformatics comparison was performed between GEP of the CTC, CNC and leukocytes from patients with malignant tumors and healthy individuals. This comparison resulted in about 30 genes that were differentially expressed in CTC and CNC cells (fold change ≥2; P≤0.05, with Multi Testing Correction on to reduce FDR rate, GeneSpring 7.2). CTC scores were then used to determine the fitness of a sample to a signature. The CTC score of a sample is the percentage of genes that match the signature. Each gene was given equal weight in distinguishing a cancer sample from a normal sample. The presence of any specific gene is neither required nor sufficient. Assuming the CTC score of 40% as a cutoff, the specificity of the CTC signature in detecting a cancer is the percentage of normal blood samples that have a CTC score less than 40%. The sensitivity of the CTC signature in detecting a cancer is defined as the percentage of cancer blood samples that have a CTC score greater than 40%.

GEP of CTC and CNC enriched by CAM from blood An experimental microarray model was used to determine if the CAM platform could enable gene expression profiling of 300 rare tumor cells in 3 ml of blood. Currently, the concentration of CTC in patients with metastatic epithelial cancers is reported having an average of 100 CTC per ml of blood; CTC were defined by pan-cytokeratin positivity (Allard et al., 2004). Cells from a tumor cell line, i.e., LOX human melanoma, SB247 human ovarian serous adenocarcinoma, MDA-MB-231 human breast ductal carcinoma, HCT116 human colon or PC3 human prostate carcinoma lines, were spiked into blood samples from healthy individuals and the tumor cells enriched by one-step, Vita-Cap™ CAM method for global gene expression profiling. CTC and CNC were separated from other normal cells by the CAM function-affinity enrichment from blood.

A hierarchical clustering analysis was performed to select a list of 27 genes signifying LOX cells in blood (FIG. 1). Columns represent catalogues of cell samples analyzed: CAC are CAM-Avid Circulating (CAC) cells isolated with the one-step CAM assay from seven healthy donors (each cell sample is named from 01 to 07); CAC-LOX1 and CAC-LOX2 are LOX cells spiked into blood samples of two independent healthy donors (each cell sample is named 1 or 2) captured by the one-step CAM assay. Rows represent the 20 upregulated LOX melanoma genes and 7 upregulated CAC cell genes. Colorgram depicts high (red) and low (blue) relative levels of gene expression. Arrowheads point to the expression of DPP4 and DPP5 in different cell samples. Note that DPP4/CD26 is a T cell activation antigen that may express differently in various individuals. For example, blood samples from healthy donors were divided into two-3 ml aliquots: experimental groups were spiked with 100 LOX cells per ml, and the control aliquot had no melanoma cells spiked. Cell samples were subjected to Vita-Cap™ enrichment for collection of the three cell fractions: CAM⁺CTC and CAM⁻ normal cells from experimental samples and CAM⁺ CNC from control samples. RNA was extracted from each cell fraction and then subjected to DNA microarray analysis using Affymetrix Hu133A 2.0 chip.

Bioinformatics comparison was performed first between the CAM⁺CTC and CAM⁻ normal cells; then between the CAM⁺CTC and CAM⁺CNC. The clustering analysis defined 27 genes that were differentially expressed between CAM⁺CTC and CAM⁺CNC (FIG. 1). The signature for LOX cells contain 20 genes upregulated in LOX cells and 7 genes upregulated in CAM-avid normal cells, and its gene expression pattern is specific for the discrimination of tumor cells from blood cells.

Thus, we demonstrated using the experimental model that the CAM platform recovered effectively tumor cells, which were spiked, at 100 tumor cells per ml of healthy blood, for performing high resolution DNA microarray of CTC.

The CTC gene signature for colon cancer. CTC and CNC were separated from other cells by the CAM function-affinity enrichment of blood from colon cancer patients. Cell purity was evaluated by immunocytochemistry and cell fractions that contained over 100 pan-cytokeratin positive cells per ml of blood were used for GEP. We isolated colon CTC by using Vita-Cap™ from five patients with late stage colon cancer. Three to ten ml of blood from five patients with late stage (3 stage III and 2 stage IV) colon cancer and six healthy individuals were subjected to Vita-Cap™ enrichment for the collection of the three cell fractions: CAM⁺CTC, CAM⁻ normal cells and CAM⁺CNC. To generate GEP of tumor cells, RNA was extracted from the CAM⁺CTC fractions and was compared with the RNA from the CAM⁺CNC and CAM⁻ normal cells by using the Affymetrix GeneChip platform. Bioinformatics comparison performed between the CAM⁺CTC and CAM⁻ normal cells resulted in about 1,200 genes that were differentially expressed in CAM⁺CTC and background blood cells (fold change ≥2; P≥0.05, with Multi Testing Correction on to reduce FDR rate, GeneSpring 7.2). We then selected approximately 100 genes that were differentially expressed between CAM⁺CTC and CAM⁺CNC. The final gene selection was based on two criteria: (1) genes known to upregulate in cells of the epithelial lineage and metastatic tumors, and (2) further hierarchical gene clustering that showed genes upregulated in CAM⁺CTC but downregulated in CAM⁺CNC, and genes upregulated in CAM⁺CNC but downregulated in CAM⁺CTC. The list of resulting genes constitutes the CTC gene expression signature for colon cancer.

Figure 2:
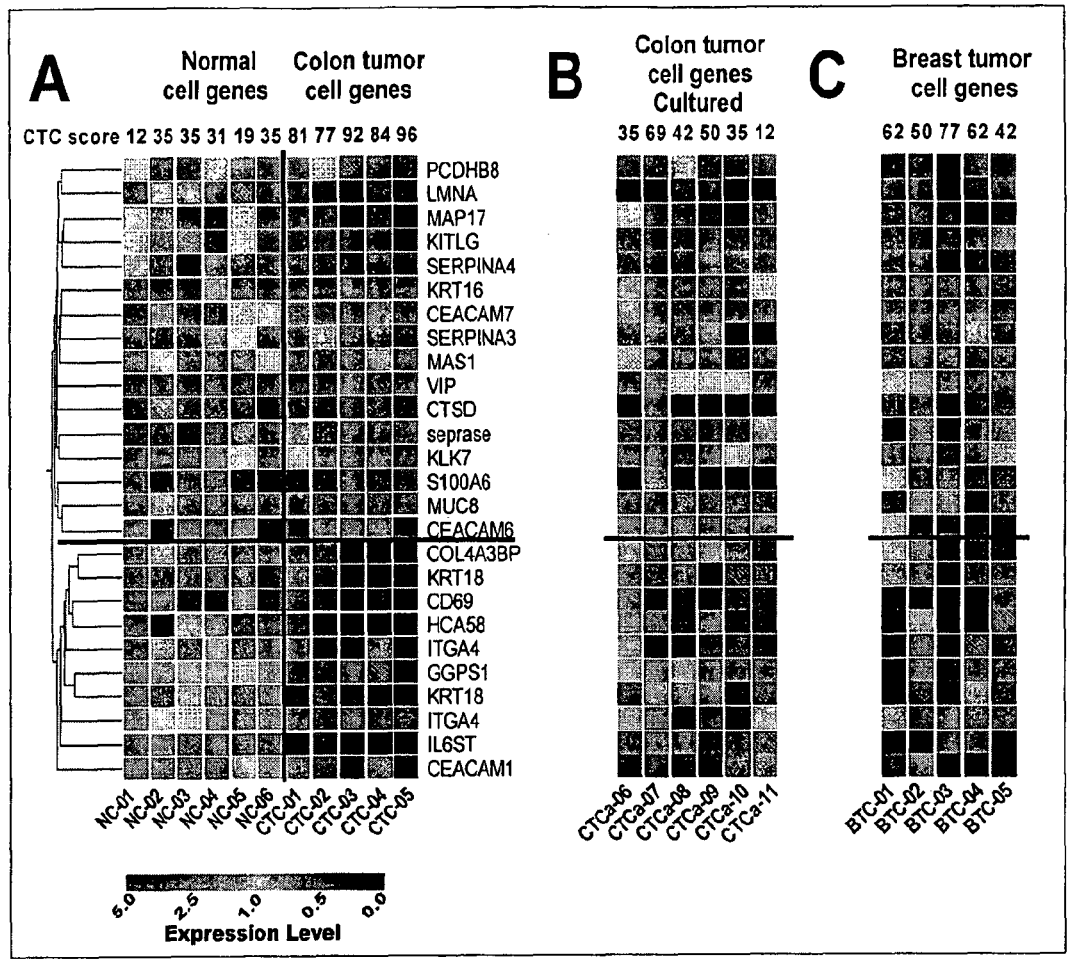
FIG. 2 shows the expression profile of 24 genes associated by hierarchical cluster analysis with circulating colon tumor cells compared with their expression in normal cells, cultured colon tumor cells and breast tumor cells. The 24-gene CTC signature for circulating colon tumor cells included components of putative tumor/epithelial lineage genes (CEACAM6 CEACAM7 KRT16 MAP17 MUC8 PCDHB8); proteases (CTSD seprase), protease inhibitors (KLK7, SERPINA3, SERPINA4), oncogenes (MAS1), stem cell factor (KITLG), cell structure (LMNA), and functional peptides (S100A6, VIP).

For example, a CTC gene expression signature consisting of 24 genes was found to be optimal in discriminating between normal and cancer samples, as well as distinguishing between colon and breast cancer samples (FIG. 2; Table I). A hierarchical clustering analysis was performed to select a list of 24 genes signifying circulating colon tumor cells. Columns represent catalogues of cell samples analyzed: circulating Normal Cells (NC) cells isolated with the one-step Vita-Cap™ assay from six healthy donors (each cell sample is named from 01 to 06); CTC-01 to 05 are circulating Colon Tumor Cells (CTC) isolated by the one-step Vita-Cap™ assay from blood samples of five patients with late stage colon cancer (each cell sample is named 01 or 05). The top 16 rows represent upregulated genes in circulating colon tumor cells and the bottom 10 rows represent 8 upregulated genes in CAM⁺ circulating normal cells (KRT18 and ITGA4 are covered by two distinct probes). The colorgram depicts high (red) and low (blue) relative levels of gene expression. The CTC score of a sample is the percent of 26 gene probes (24 genes) that matches the signature. CTC scores for colon tumor cells are 77-96%, whereas normal cells are 12-35%. The 24-gene signature in tumor cells isolated by Vita-Assay™ from six colon cancer patients (cell samples are labelled CTCa) that were cultured for over one day was also examined (column B of FIG. 2). CTC scores for the colon tumor cells isolated by Vita-Assay™ are 12-69%. Examination of the 24-gene signature in circulating breast tumor cells isolated by Vita-Cap™ from five patients with late stage breast cancer (column C of FIG. 2—cell samples are labelled BTC). The CTC scores for the breast tumor cells isolated by Vita-Cap™ are 42-77%.

TABLE I

The 24-gene signature associated with circulating colon tumor cells

| Gene | Gene name | GenBank ID |
|---|---|---|
| Upregulated (16) | | |
| CEACAM6 | carcinoembryonic antigen-related cell adhesion molecule 6 | BC005008 |
| CEACAM7 | carcinoembryonic antigen-related cell adhesion molecule 7 | L31792 |
| CTSD | cathepsin D | NM_001909 |
| DPP5/Seprase | integral membrane serine protease Seprase/fibroblast activation protein, alpha | U76833 |
| KITLG | stem cell factor precursor | AF119835 |
| KLK7 | kallikrein 7 | NM_005046 |
| KRT16 | keratin 16 | AF061812 |
| LMNA | lamin A/C | AA063189 |
| MAP17 | epithelial protein up-regulated in carcinoma, membrane associated protein 17 (DD96) | NM_005764 |
| MAS1 | MAS1 oncogene | NM_002377 |
| MUC8 | mucin 8 | U14383 |
| PCDHB8 | protocadherin beta 8 | NM_019120 |
| S100A6 | S100 calcium-binding protein A6 | NM_014624 |
| SERPINA3 | serine (or cysteine) proteinase inhibitor, clade A, member 3 | NM_001085 |
| SERPINA4 | serine (or cysteine) proteinase inhibitor, clade A, member 4 | NM_006215 |
| VIP | vasoactive intestinal peptide | NM_003381 |
| Downregulated (8) | | |
| CD69 | early activation antigen CD69 | L07555 |
| CEACAM1 | carcinoembryonic antigen-related cell adhesion molecule 1 | M69176 |
| CK18 | Cytoskeletal 18 | AL031685 |
| COL4A3BP | collagen, type IV, alpha 3 binding protein | NM_005713 |

TABLE I-continued

The 24-gene signature associated with circulating colon tumor cells

| Gene | Gene name | GenBank ID |
|---|---|---|
| GGPS1 | thromboxane A-2 receptor | AW299507 |
| HCA58 | hepatocellular carcinoma-associated antigen 58 | AL109965 |
| IL6ST | interleukin 6 signal transducer | BE856546 |
| ITGA4 | integrin, alpha 4 | BG532690 |

Since individual genes of the CTC signature expressed differently in all samples examined, we defined the CTC score of a sample as the percentage of gene probes that matched the upregulated expression of 26 gene probes in the CTC signature. The CTC scores for circulating colon tumor cells were 77-96, whereas they were 12-35 for circulating normal cells. The tumor cells isolated by the same method but cultured for over one day appeared to have a somewhat altered gene expression profile. Nevertheless, these findings demonstrate the efficiency of the CAM cell enrichment approach used to acquire circulating tumor cell-specific GEP.

The 24-gene CTC signature for circulating colon tumor cells contained a total of 16 upregulated genes that included components of putative tumor/epithelial lineage genes (CEACAM6, CEACAM7, KRT16, MAP17, MUC8, PCDHB8); proteases (CTSD, seprase), protease inhibitors (KLK7, SERPINA3, SERPINA4), oncogenes (MAS1), stem cell factor (KITLG), cell structure (LMNA), and functional peptides (S100A6, VIP) (FIG. 2A and Table I), suggesting that these genes were specific for circulating colon tumor cells; some of them in bold were common with circulating breast tumor cells and, thus, active in metastasis. The 8 genes downregulated in CAM+ tumor cells and upregulated in CAM+ normal cells include epithelial lineage marker genes (CEACAM1, CK18, and HCA58), ECM and adhesion receptors produced by epithelial cells (COL4A3BP, and ITGA4), and receptor and signal transducer (CD69, GGPS1 and IL6ST), indicating that these genes were active in the invasion of circulating normal cells into collagenous matrices. Our results show that CAM+ tumor cells have a distinct gene signature that CAM+ normal cells lack.

The results show that greater than 23 out of 26 gene probes (two genes, KRT18 and ITGA4, with duplicate probes) in each tumor cell sample match the signature. The 3 unmatched genes in a CTC sample (CTC-01) can be explained by gene expression differences in individuals and cells in their distinct physiological state or defect of the gene chip (note the difference of two different KRT18 gene probes in the CTC-01 patient). However, the results verify that the CAM platform enables the identification of a gene signature for circulating colon tumor cells.

Figure 3:
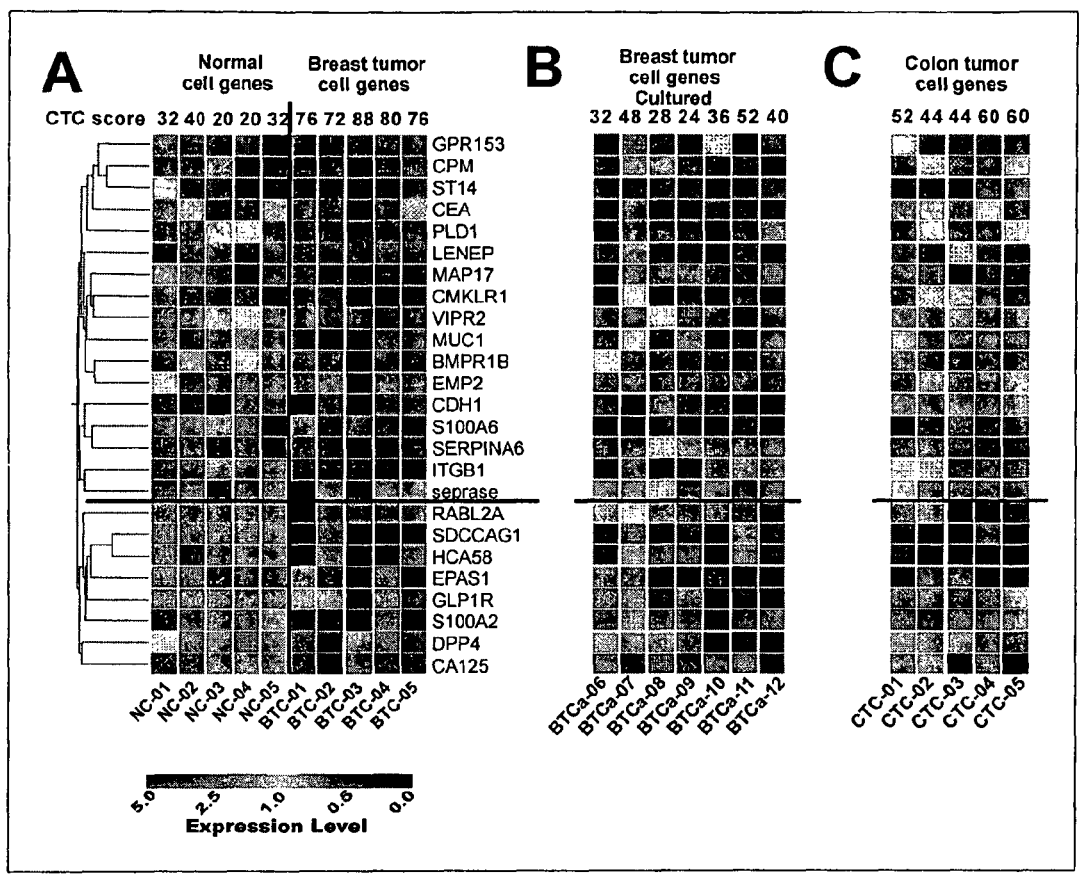
FIG. 3 shows the expression profile of 25 genes associated with circulating breast tumor cells compared with their expression in normal cells, cultured breast cancer cells and colon tumor cells.

The CTC gene signature for breast cancer. Based on analysis of the microarray data of Vita-Cap™ enriched tumor cells in the experimental microarray model (FIG. 1) and clinical blood samples from late stage colon cancer patients (FIG. 2) above, we similarly defined a 25-gene signature optimal for the identification of circulating breast tumor cells (FIG. 3 and Table II).

TABLE II

The 25-gene signature associated with circulating breast tumor cells

| Gene | Gene name | GenBank ID |
|---|---|---|
| Upregulated (17) | | |
| BMPR1B | bone morphogenetic protein receptor, type IB | D89675 |
| CDH1 | E-cadherin | AI183766 |
| CEA | carcinoembryonic antigen gene. | Z21818 |
| CMKLR1 | chemokine-like receptor 1 | NM_004072 |
| CPM | carboxypeptidase M | AV710357 |
| EMP2 | epithelial membrane protein 2 | NM_001424 |
| DPP5/seprase | integral membrane serine protease Seprase/fibroblast activation protein, alpha | U76833 |
| GPR153 | mucin 2 precursor | AL567940 |
| ITGB1 | integrin, beta 1 | BG435463 |
| LENEP | lens epithelial protein | NM_018655 |
| MAP17 | epithelial protein up-regulated in carcinoma, membrane associated protein 17 | NM_005764 |
| MUC1 | mucin 1 | NM_002456 |
| PLD1 | phospholipase D1 | AJ276230 |
| S100A6 | S100 calcium-binding protein A6 | NM_014624 |
| SERPINA6 | serine (or cysteine) proteinase inhibitor, clade A, member 6 | NM_001756 |
| ST14 | matriptase | NM_021978 |
| VIPR2 | vasoactive intestinal peptide receptor 2 | NM_003382 |
| Downregulated (8) | | |
| CA125 | ovarian carcinoma antigen CA125 | NM_005899 |
| DPP4 | dipeptidyl peptidase IV | M74777 |
| EPAS1 | endothelial PAS domain protein 1 | AF052094 |
| GLP1R | glucagon-like peptide-1 receptor | U01157 |
| HCA58 | hepatocellular carcinoma-associated antigen 58 | AL109965 |
| RABL2A | member of RAS oncogene family-like 2A | NM_007082 |
| S100A2 | S100 calcium-binding protein A2 | NM_005978 |
| SDCCAG1 | serologically defined colon cancer antigen 1 | NM_004713 |

A hierarchical clustering analysis was performed to select a list of 25 genes signifying circulating breast tumor cells. Referring to FIG. 3, columns represent catalogues of cell samples analyzed: NC are circulating Normal Cells (NC) isolated with the one-step Vita-Cap™ assay from five healthy donors (each cell sample is named from 01 to 05); BTC-01 to 05 are circulating Breast Tumor Cells (BTC) isolated by Vita-Cap™ assay from blood samples of five patients with late stage breast cancer (each cell sample is named 01 or 05). The top 17 rows represent the upregulated genes in circulating breast tumor cells and the bottom 8 rows represent downregulated genes. Colorgram depicts high (red) and low (blue) relative levels of gene expression. The CTC score of a sample is the percent of 25 genes that match the signature. CTC scores for breast tumor cells are 72-88, whereas normal cells are 20-40. Examination of the 25-gene signature in the tumor cells isolated by Vita-Assay™ from seven breast cancer patients (cell samples are labelled BTCa) and cultured for over one day. CTC scores for the breast tumor cells isolated by Vita-Assay™ are 24-52 gave the results in column B. Examination of the breast signature in the circulating colon tumor cells isolated by Vita-Cap™ from five patients with late stage colon cancer (cell samples are labelled CTC) gave the results in column C. The CTC scores for the colon tumor cells isolated by Vita-Cap™ are 44-60.

The 25-gene CTC signature for breast cancer contained a total of 17 upregulated circulating breast tumor cell genes that included components of putative tumor/epithelial lineage genes (CDH1, CEA, EMP2, GPR153, LENEP, MAP17, MUC1); proteases (CPM, seprase, ST14), protease inhibitors (SERPINA6), adhesion and chemokine receptors (BMPR1B, CMKLR1, ITGB1), and functional peptides (PLD1, S100A6, VIPR2) (FIG. 3A and Table II), suggesting that these genes were specific for circulating breast tumor cells; some of them in bold were common with circulating colon tumor cells and, thus, active in metastasis. The 8 genes downregulated in CAM+ tumor cells and upregulated in CAM+ normal cells include epithelial lineage marker genes (CA125, HCA58, SDCCAG1), endothelial lineage marker gene (EPAS1), T-cell marker gene (DPP4), and peptide receptor and signal transducer (GLP1R, RABL2A, S100A2), indicating that these genes were active in the invasion of circulating normal cells into collagenous matrices. Our results show that CAM+ tumor cells have a distinct gene signature that CAM+ normal cells lack.

Since individual genes of the breast CTC signature expressed differently in all samples examined, we defined the CTC score of a sample as the percentage of genes that matched the expression pattern of 25 genes in the breast CTC signature. The CTC scores for circulating breast tumor cells were 72-88, whereas they were 20-40 for circulating normal cells (FIG. 3A). Examination of the 25-gene expression pattern in the breast tumor cells, isolated by Vita-Assay™ from seven breast cancer patients and cultured for over one day, showed CTC scores ranging between 24-52 (FIG. 3B), suggesting that tumor cells isolated by same method but cultured for over one days alter their gene expression profiles. These findings indicated the efficiency of the CAM cell enrichment approach used to acquire circulating tumor cell-specific GEP.

Figure 4:
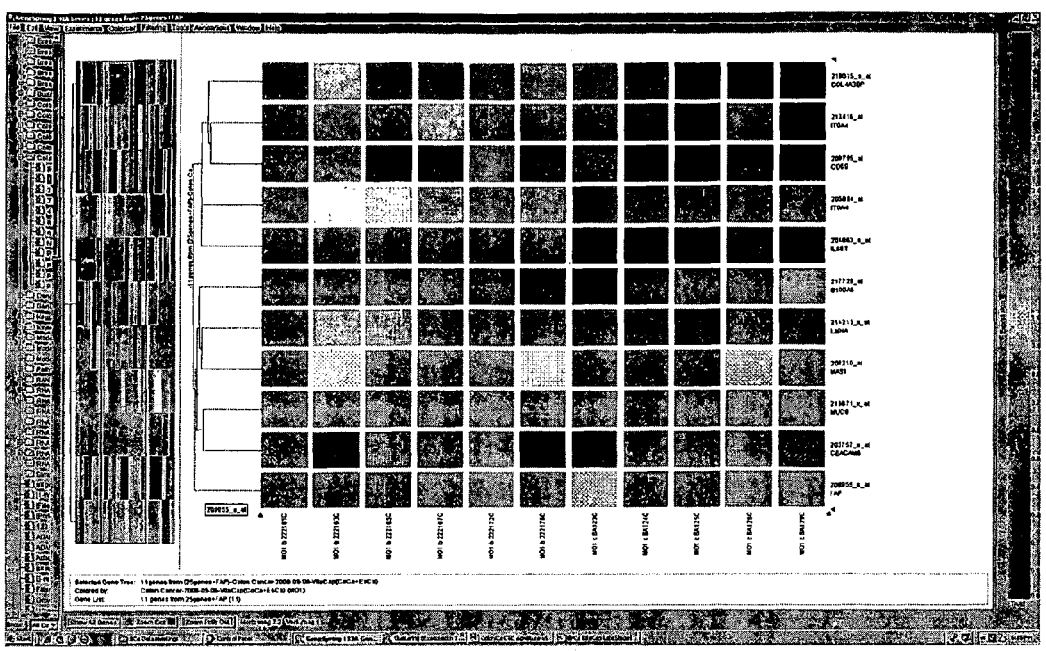
FIG. 4 is a colorgram of a colon CTC signature effective in discriminating colon cancer from normal cells in a blood sample.

Ranges of genes in CTC signatures useful in the discrimination between cancer and normal blood samples. The colon CTC signatures that contain genes ranging from 42 down to two (one gene upregulated and one gene downregulated) were used to positively discriminate between cancer and normal blood samples. For example, when 11 genes were selected from the signature (FIG. 4; Table III), the colon CTC signature discriminated a colon cancer from normal blood sample.

TABLE III

| | The 11-gene signature associated with circulating colon tumor cells |
|---|---|
| 219625_s_at | gb: NM_005713.1 /DEF = *Homo sapiens* collagen, type IV, alpha 3 (Goodpasture antigen) binding protein (COL4A3BP), mRNA. /FEA = mRNA /GEN = COL4A3BP /PROD = collagen, type IV, alpha 3 (Goodpasture antigen)binding protein /DB_XREF = gi: 5031716 /UG = Hs.21276 collagen, type IV, alpha 3 (Goodpasture antigen) binding protein /FL = gb: AF136450.1 gb: NM_005713.1 |
| 217728_at | gb: NM_014624.2 /DEF = *Homo sapiens* S100 calcium-binding protein A6 (calcyclin) (S100A6), mRNA. /FEA = mRNA /GEN = S100A6 /PROD = S100 calcium-binding protein A6 /DB_XREF = gi: 9845517 /UG = Hs.275243 S100 calcium-binding protein A6 (calcyclin) /FL = gb: BC001431.1 gb: NM_014624.2 |
| 216671_x_at | Consensus includes gb: U14383.1 /DEF = Human mucin (MUC8) mRNA, partial cds. /FEA = mRNA /GEN = MUC8 /PROD = mucin /DB_XREF = gi: 606953 /UG = Hs.1607 mucin 8, tracheobronchial |
| 214213_x_at | lamin A/C |
| 213416_at | integrin, alpha 4 (antigen CD49D, alpha 4 subunit of VLA-4 receptor) |
| 209955_s_at | gb: U76833.1 /DEF = Human integral membrane serine protease Seprase mRNA, complete cds. /FEA = mRNA /PROD = integral membrane serine protease Seprase /DB_XREF = gi: 1924981 /UG = Hs.418 fibroblast activation protein, alpha /FL = gb: U09278.1 gb: U76833.1 gb: NM_004460.1 |
| 209795_at | gb: L07555.1 /DEF = *Homo sapiens* early activation antigen CD69 mRNA, complete cds. /FEA = mRNA /PROD = early activation antigen CD69 /DB_XREF = gi: 291897 /UG = Hs.82401 CD69 antigen (p60, early T-cell activation antigen) /FL = gb: L07555.1 gb: NM_001781.1 |
| 208210_at | gb: NM_002377.2 /DEF = *Homo sapiens* MAS1 oncogene (MAS1), mRNA. /FEA = mRNA /GEN = MAS1 /PROD = MAS1 oncogene /DB_XREF = gi: 6006022 /UG = Hs.99900 MAS1 oncogene /FL = gb: M13150.1 gb: NM_002377.2 |
| 205884_at | gb: NM_000885.2 /DEF = *Homo sapiens* integrin, alpha 4 (antigen CD49D, alpha 4 subunit of VLA-4 receptor) (ITGA4), mRNA. /FEA = mRNA /GEN = ITGA4 /PROD = integrin alpha 4 precursor /DB_XREF = gi: 6006032 /UG = Hs.40034 integrin, alpha 4 (antigen CD49D, alpha 4 subunit of VLA-4 receptor) /FL = gb: NM_000885.2 gb: L12002.1 |
| 204863_s_at | interleukin 6 signal transducer (gp130, oncostatin M receptor) |
| 203757_s_at | gb: BC005008.1 /DEF = *Homo sapiens*, carcinoembryonic antigen-related cell adhesion molecule 6 (non-specific cross reacting antigen), clone MGC: 10467, mRNA, complete cds. /FEA = mRNA /PROD = carcinoembryonic antigen-related cell adhesionmolecule 6 (non-specific cross reacting antigen) /DB_XREF = gi: 13477106 /UG = Hs.73848 carcinoembryonic antigen-related cell adhesion molecule 6 (non-specific cross reacting antigen) /FL = gb: BC005008.1 gb: M18216.1 gb: M29541.1 gb: NM_002483.1 |

Figure 5:
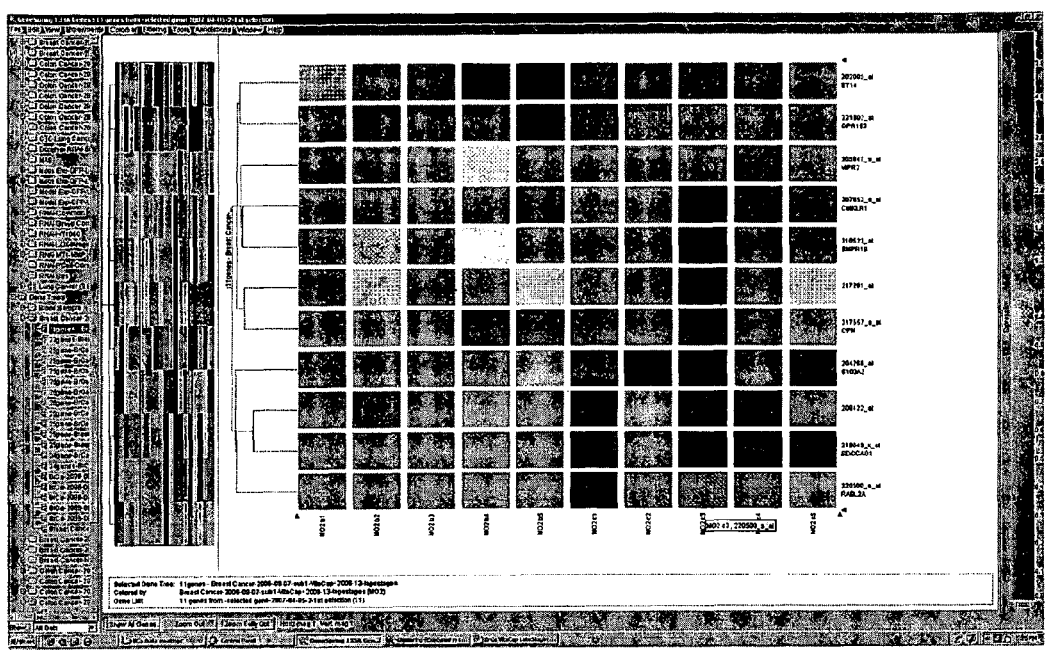
FIG. 5 is a colorgram of a breast CTC signature effective in discriminating breast cancer from normal cells in a blood sample.

Similarly, the breast CTC signatures that contain genes ranging from 62 down to two (one gene upregulated and one gene downregulated) were used to positively discriminate between cancer and normal blood samples. For example, when 11 genes were selected from the signature (FIG. 5; Table IV), the breast CTC signature discriminated a colon cancer from normal blood sample.

TABLE IV

The 11-gene signature associated with circulating breast tumor cells

| | |
|---|---|
| 202005_at | gb: NM_021978.1 /DEF = *Homo sapiens* suppression of tumorigenicity 14 (colon carcinoma, matriptase, epithin) (ST14), mRNA. /FEA = mRNA /GEN = ST14 /PROD = suppression of tumorigenicity 14 (coloncarcinoma, matriptase, epithin) /DB_XREF = gi: 11415039 /UG = Hs.56937 suppression of tumorigenicity 14 (colon carcinoma, matriptase, epithin) /FL = gb: AF057145.1 gb: NM_021978.1 gb: AB030036.1 gb: AF133086.1 gb: AF118224.2 |
| 204268_at | gb: NM_005978.2 /DEF = *Homo sapiens* S100 calcium-binding protein A2 (S100A2), mRNA. /FEA = mRNA /GEN = S100A2 /PROD = S100 calcium-binding protein A2 /DB_XREF = gi: 9845513 /UG = Hs.38991 S100 calcium-binding protein A2 /FL = gb: BC002829.1 gb: NM_005978.2 |
| 205947_s_at | gb: NM_003382.1 /DEF = *Homo sapiens* vasoactive intestinal peptide receptor 2 (VIPR2), mRNA. /FEA = mRNA /GEN = VIPR2 /PROD = vasoactive intestinal peptide receptor 2 /DB_XREF = gi: 4507898 /UG = Hs.2126 vasoactive intestinal peptide receptor 2 /FL = gb: NM_003382.1 gb: L36566.1 |
| 207652_s_at | gb: NM_004072.1 /DEF = *Homo sapiens* chemokine-like receptor 1 (CMKLR1), mRNA. /FEA = mRNA /GEN = CMKLR1 /PROD = chemokine-like receptor 1 /DB_XREF = gi: 4758013 /UG = Hs.159553 chemokine-like receptor 1 /FL = gb: U79527.1 gb: NM_004072.1 |
| 209422_at | Consensus includes gb: AL109965 /DEF = Human DNA sequence from clone RP5-1121G12 on chromosome 20 Contains the 3 end of a gene encoding two isoforms (the hepatocellular carcinoma-associated antigen 58 (HCA58) and a putative novel protein containing a PHD finger domain), the SCAND1 gen . . . /FEA = mRNA_2 /DB_XREF = gi: 9663113 /UG = Hs.112594 hypothetical protein DKFZp434F0272 /FL = gb: AY027523.1 gb: AF348207.1 |
| 210523_at | gb: D89675.1 /DEF = *Homo sapiens* mRNA for bone morphogenetic protein type IB receptor, complete cds. /FEA = mRNA /PROD = bone morphogenetic protein type IB receptor /DB_XREF = gi: 2055308 /UG = Hs.87223 bone morphogenetic protein receptor, type IB /FL = gb: D89675.1 gb: U89326.1 |
| 217291_at | gb: NM_001203.1 *H. sapiens* carcinoembryonic antigen gene. |
| 217557_s_at | carboxypeptidase M |
| 218649_x_at | gb: NM_004713.1 /DEF = *Homo sapiens* serologically defined colon cancer antigen 1 (SDCCAG1), mRNA. /FEA = mRNA /GEN = SDCCAG1 /PROD = serologically defined colon cancer antigen 1 /DB_XREF = gi: 4759077 /UG = Hs.54900 serologically defined colon cancer antigen 1 /FL = gb: AF039687.1 gb: NM_004713.1 |
| 220500_s_at | gb: NM_007082.2 /DEF = *Homo sapiens* RAB, member of RAS oncogene family-like 2A (RABL2A), mRNA. /FEA = mRNA /GEN = RABL2A /PROD = RAB, member of RAS oncogene family-like 2A /DB_XREF = gi: 7549818 /UG = Hs.122660 RAB, member of RAS oncogene family-like 2A /FL = gb: AF095350.1 gb: NM_007082.2 |
| 221902_at | ESTs, Weakly similar to A43932 mucin 2 precursor, intestinal - human (fragments) [*H. sapiens*] |

Assuming the CTC score of 40 as a cutoff, current CTC signatures for colon and breast cancers have 100% specificity using the set of 19 healthy individuals examined, including 13 additional normal blood samples isolated using the Vita-Assay™ platform. None of 10 patients with breast and colon cancers (cell isolation by Vita-Cap™ shown above) had a CTC score falling below 40, suggesting a sensitivity of 100% for detecting either colon or breast cancer.

Figure 6:
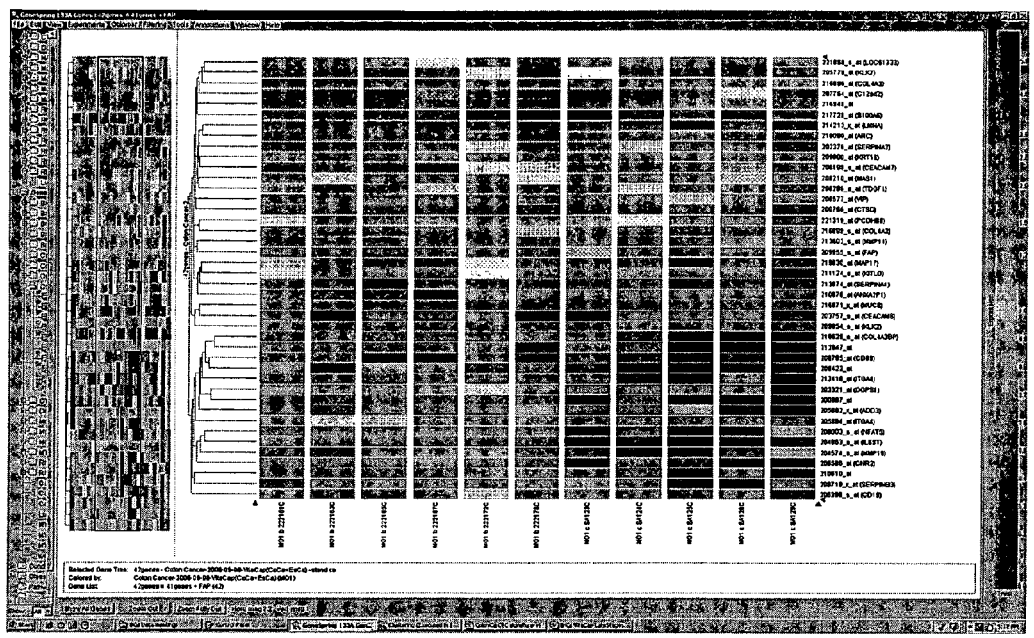
FIG. 6 is a colorgram of an enlarged colon CTC signature having 42 constituents.

Ranges of genes in CTC signatures useful in the differentiation between colon and breast cancer blood samples. The colon CTC signatures that contain genes ranging from 42 down to 25 (FIG. 2; Table I) were used to positively distinguish colon from breast cancer samples (FIG. 6; Table V). For example, when 42 genes were selected from the signature, the colon CTC signature discriminated a colon cancer from breast cancer sample.

TABLE V

The 42-gene signature associated with circulating colon tumor cells

| | |
|---|---|
| 206577_at | gb: NM_003381.1 /DEF = *Homo sapiens* vasoactive intestinal peptide (VIP), mRNA. /FEA = mRNA /GEN = VIP /PROD = vasoactive intestinal peptide /DB_XREF = gi: 4507896 /UG = Hs.53973 vasoactive intestinal peptide /FL = gb: M36634.1 gb: NM_003381.1 |
| 210090_at | gb: AF193421.1 /DEF = *Homo sapiens* ARC mRNA, complete cds. /FEA = mRNA /GEN = ARC /PROD = ARC /DB_XREF = gi: 6319151 /UG = Hs.40888 activity-regulated cytoskeleton-associated protein /FL = gb: AF193421.1 gb: NM_015193.1 |
| 207754_at | gb: NM_007211.1 /DEF = *Homo sapiens* carcinoma associated (HOJ-1), mRNA. /FEA = mRNA /GEN = HOJ-1 /PROD = carcinoma associated /DB_XREF = gi: 6005777 /UG = Hs.28529 chromosome 12 open reading frame 2 /FL = gb: U82396.1 gb: NM_007211.1 |
| 202376_at | gb: NM_001085.2 /DEF = *Homo sapiens* serine (or cysteine) proteinase inhibitor, clade A (alpha-1 antiproteinase, antitrypsin), member 3 (SERPINA3), mRNA. /FEA = mRNA /GEN = SERPINA3 /PROD = alpha-1-antichymotrypsin, precursor /DB_XREF = gi: 9665246 /UG = Hs.234726 serine (or cysteine) proteinase inhibitor, clade A (alpha-1 antiproteinase, antitrypsin), member 3 /FL = gb: BC003559.1 gb: K01500.1 gb: NM_001085.2 |
| 205778_at | gb: NM_005046.1 /DEF = *Homo sapiens* kallikrein 7 (chymotryptic, stratum corneum) (KLK7), mRNA. /FEA = mRNA /GEN = KLK7 /PROD = kallikrein 7 (chymotryptic, stratum corneum) /DB_XREF = gi: 4826949 /UG = Hs.151254 kallikrein 7 (chymotryptic, stratum corneum) /FL = gb: NM_005046.1 gb: L33404.1 |
| 208210_at | gb: NM_002377.2 /DEF = *Homo sapiens* MAS1 oncogene (MAS1), mRNA. /FEA = mRNA /GEN = MAS1 /PROD = MAS1 oncogene /DB_XREF = gi: 6006022 /UG = Hs.99900 MAS1 oncogene /FL = gb: M13150.1 gb: NM_002377.2 |
| 203757_s_at | gb: BC005008.1 /DEF = *Homo sapiens*, carcinoembryonic antigen-related cell adhesion molecule 6 (non-specific cross reacting antigen), clone MGC: 10467, mRNA, complete cds. /FEA = mRNA /PROD = carcinoembryonic antigen-related cell adhesionmolecule 6 (non-specific cross reacting antigen) /DB_XREF = gi: 13477106 /UG = Hs.73848 carcinoembryonic antigen-related cell adhesion molecule 6 (non-specific cross reacting antigen) /FL = gb: BC005008.1 gb: M18216.1 gb: M29541.1 gb: NM_002483.1 |
| 209854_s_at | kallikrein 2, prostatic |
| 216896_at | Consensus includes gb: U02519.1 /DEF = Human collagen type IV alpha 3 alternatively spliced mRNA, partial cds. /FEA = mRNA /PROD = collagen type IV alpha 3 /DB_XREF = gi: 409106 /UG = Hs.530 collagen, type IV, alpha 3 (Goodpasture antigen) |
| 206198_s_at | gb: L31792.1 /DEF = *Homo sapiens* carcinoembryonic antigen (CGM2) mRNA, complete cds. /FEA = mRNA /GEN = CGM2 /PROD = carcinoembryonic antigen /DB_XREF = gi: 471076 /UG = Hs.74466 carcinoembryonic antigen-related cell adhesion molecule 7 /FL = gb: AF006622.1 gb: L31792.1 gb: NM_006890.1 |
| 216948_at | Consensus includes gb: AL049545 /DEF = Human DNA sequence from clone 263J7 on chromosome 6q14.3-15. Contains an RPL7 (60S Ribosomal Protein L7) pseudogene, a RAB1 (RAB1, member RAS oncogene family) pseudogene, ESTs, an STS and GSSs /FEA = CDS_2 /DB_XREF = gi: 5002650 /UG = Hs.247878 Human DNA sequence from clone 263J7 on chromosome 6q14.3-15. Contains an RPL7 (60S Ribosomal Protein L7) pseudogene, a RAB1 (RAB1, member RAS oncogene family) pseudogene, ESTs, an STS and GSSs |
| 200766_at | gb: NM_001909.1 /DEF = *Homo sapiens* cathepsin D (lysosomal aspartyl protease) (CTSD), mRNA. /FEA = mRNA /GEN = CTSD /PROD = cathepsin D (lysosomal aspartyl protease) /DB_XREF = gi: 4503142 /UG = Hs.79572 cathepsin D (lysosomal aspartyl protease) /FL = gb: M11233.1 gb: NM_001909.1 |
| 221968_s_at | mesenchymal stem cell protein DSC43 |
| 213602_s_at | matrix metalloproteinase 11 (stromelysin 3) |
| 209800_at | gb: AF061812.1 /DEF = *Homo sapiens* keratin 16 (KRT16A) mRNA, complete cds. /FEA = mRNA /GEN = KRT16A /PROD = keratin 16 /DB_XREF = gi: 4091878 /UG = Hs.115947 keratin 16 (focal non-epidermolytic palmoplantar keratoderma) /FL = gb: AF061812.1 gb: NM_005557.1 |
| 216671_x_at | Consensus includes gb: U14383.1 /DEF = Human mucin (MUC8) mRNA, partial cds. /FEA = mRNA /GEN = MUC8 /PROD = mucin /DB_XREF = gi: 606953 /UG = Hs.1607 mucin 8, tracheobronchial |
| 211124_s_at | gb: AF119835.1 /DEF = *Homo sapiens* stem cell factor precursor, mRNA, complete cds. /FEA = mRNA /PROD = stem cell factor precursor /DB_XREF = gi: 4530470 /UG = Hs.1048 KIT ligand /FL = gb: AF119835.1 gb: NM_003994.2 |
| 213874_at | Consensus includes gb: NM_006215.1 /DEF = *Homo sapiens* serine (or cysteine) proteinase inhibitor, clade A (alpha-1 antiproteinase, antitrypsin), member 4 (SERPINA4), mRNA. /FEA = CDS /GEN = SERPINA4 /PROD = serine (or cysteine) proteinase inhibitor, cladeA (alpha-1 antiproteinase, antitrypsin), member 4 /DB_XREF = gi: 5453887 /UG = Hs.159628 serine (or cysteine) proteinase inhibitor, clade A (alpha-1 antiproteinase, antitrypsin), member 4 /FL = gb: L19684.1 gb: NM_006215.1 |
| 206286_s_at | gb: NM_003212.1 /DEF = *Homo sapiens* teratocarcinoma-derived growth factor 1 (TDGF1), mRNA. /FEA = mRNA /GEN = TDGF1 /PROD = teratocarcinoma-derived growth factor 1 /DB_XREF = gi: 4507424 /UG = Hs.75561 teratocarcinoma-derived growth factor 1 /FL = gb: NM_003212.1 |
| 216898_s_at | Consensus includes gb: U02520.1 /DEF = Human collagen type IV alpha 3 mRNA, partial cds. /FEA = mRNA /PROD = collagen type IV alpha 3 /DB_XREF = gi: 408895 /UG = Hs.530 collagen, type IV, alpha 3 (Goodpasture antigen) |

TABLE V-continued

The 42-gene signature associated with circulating colon tumor cells

| | |
|---|---|
| 219630_at | gb: NM_005764.1 /DEF = *Homo sapiens* epithelial protein up-regulated in carcinoma, membrane associated protein 17 (DD96), mRNA. /FEA = mRNA /GEN = DD96 /PROD = epithelial protein up-regulated in carcinoma, membrane associated protein 17 /DB_XREF = gi: 5031656 /UG = Hs.271473 epithelial protein up-regulated in carcinoma, membrane associated protein 17 /FL = gb: NM_005764.1 |
| 210876_at | gb: M62896.1 /DEF = Human lipocortin (LIP) 2 pseudogene mRNA, complete cds-like region. /FEA = mRNA /DB_XREF = gi: 187146 /UG = Hs.234757 Human lipocortin (LIP) 2 pseudogene mRNA, complete cds-like region /FL = gb: M62896.1 |
| 221319_at | gb: NM_019120.1 /DEF = *Homo sapiens* protocadherin beta 8 (PCDHB8), mRNA. /FEA = CDS /GEN = PCDHB8 /PROD = protocadherin beta 8 /DB_XREF = gi: 11276080 /UG = Hs.287793 protocadherin beta 8 /FL = gb: AF152501.2 gb: NM_019120.1 |
| 217728_at | gb: NM_014624.2 /DEF = *Homo sapiens* S100 calcium-binding protein A6 (calcyclin) (S100A6), mRNA. /FEA = mRNA /GEN = S100A6 /PROD = S100 calcium-binding protein A6 /DB_XREF = gi: 9845517 /UG = Hs.275243 S100 calcium-binding protein A6 (calcyclin) /FL = gb: BC001431.1 gb: NM_014624.2 |
| 214213_x_at | lamin A/C |
| 209422_at | Consensus includes gb: AL109965 /DEF = Human DNA sequence from clone RP5-1121G12 on chromosome 20 Contains the 3 end of a gene encoding two isoforms (the hepatocellular carcinoma-associated antigen 58 (HCA58) and a putative novel protein containing a PHD finger domain), the SCAND1 gen . . . /FEA = mRNA_2 /DB_XREF = gi: 9663113 /UG = Hs.112594 hypothetical protein DKFZp434F0272 /FL = gb: AY027523.1 gb: AF348207.1 |
| 202321_at | ESTs, Weakly similar to A53959 thromboxane A-2 receptor, endothelial - human [*H. sapiens*] |
| 209719_x_at | gb: U19556.1 /DEF = Human squamous cell carcinoma antigen 1 (SCCA1) mRNA, complete cds. /FEA = mRNA /GEN = SCCA1 /PROD = squamous cell carcinoma antigen 1 /DB_XREF = gi: 1276435 /UG = Hs.227948 serine (or cysteine) proteinase inhibitor, clade B (ovalbumin), member 3 /FL = gb: U19556.1 gb: BC005224.1 gb: NM_006919.1 |
| 200867_at | Consensus includes gb: AL031685 /DEF = Human DNA sequence from clone RP5-963K23 on chromosome 20q13.11-13.2 Contains a KRT18 (Keratin type I, Cytoskeletal 18 (Cytokeratin 18, CK18, CYK18)) pseudogene, a gene for a novel protein, the gene for spermatogenesis associated protein PD1 (KIAA0 . . . /FEA = mRNA_2 /DB_XREF = gi: 9368423 /UG = Hs.10590 zinc finger protein 313 /FL = gb: AF265215.1 gb: NM_018683.1 |
| 210610_at | gb: M69176.1 /DEF = Human-biliary glycoprotein mRNA, complete cds. /FEA = mRNA /GEN = BGP /PROD = biliary glycoprotein a /DB_XREF = gi: 179434 /UG = Hs.50964 carcinoembryonic antigen-related cell adhesion molecule 1 (CEACAM1, biliary glycoprotein) /FL = gb: M69176.1 |
| 205882_x_at | adducin 3 (gamma) |
| 212947_at | Consensus includes gb: AL031685 /DEF = Human DNA sequence from clone RP5-963K23 on chromosome 20q13.11-13.2 Contains a KRT18 (Keratin type I, Cytoskeletal 18 (Cytokeratin 18, CK18, CYK18)) pseudogene, a gene for a novel protein, the gene for spermatogenesis associated protein PD1 (KIAA0 . . . /FEA = mRNA_3 /DB_XREF = gi: 9368423 /UG = Hs.12785 KIAA0939 protein |
| 219625_s_at | gb: NM_005713.1 /DEF = *Homo sapiens* collagen, type IV, alpha 3 (Goodpasture antigen) binding protein (COL4A3BP), mRNA. /FEA = mRNA /GEN = COL4A3BP /PROD = collagen, type IV, alpha 3 (Goodpasture antigen)binding protein /DB_XREF = gi: 5031716 /UG = Hs.21276 collagen, type IV, alpha 3 (Goodpasture antigen) binding protein /FL = gb: AF136450.1 gb: NM_005713.1 |
| 206586_at | gb: NM_001841.1 /DEF = *Homo sapiens* cannabinoid receptor 2 (macrophage) (CNR2), mRNA. /FEA = mRNA /GEN = CNR2 /PROD = cannabinoid receptor 2 (macrophage) /DB_XREF = gi: 4502928 /UG = Hs.73037 cannabinoid receptor 2 (macrophage) /FL = gb: NM_001841.1 |
| 204574_s_at | gb: NM_002429.2 /DEF = *Homo sapiens* matrix metalloproteinase 19 (MMP19), transcript variant rasi-1, mRNA. /FEA = mRNA /GEN = MMP19 /PROD = matrix metalloproteinase 19, isoform rasi-1, preproprotein /DB_XREF = gi: 13027788 /UG = Hs.154057 matrix metalloproteinase 19 /FL = gb: NM_002429.2 gb: U38321.1 gb: U37791.1 |
| 206398_s_at | gb: NM_001770.1 /DEF = *Homo sapiens* CD19 antigen (CD19), mRNA. /FEA = mRNA /GEN = CD19 /PROD = CD19 antigen /DB_XREF = gi: 10835052 /UG = Hs.96023 CD19 antigen /FL = gb: NM_001770.1 gb: M21097.1 gb: M28170.1 |
| 208003_s_at | gb: NM_006599.1 /DEF = *Homo sapiens* nuclear factor of activated T-cells 5, tonicity-resonsive (NFAT5), mRNA. /FEA = mRNA /GEN = NFAT5 /PROD = nuclear factor of activated T-cell 5, tonicity-resonsive /DB_XREF = gi: 5729944 /UG = Hs.86998 nuclear factor of activated T-cell 5, tonicity-responsive /FL = gb: AB020634.1 gb: AF163836.1 gb: NM_006599.1 |
| 213416_at | integrin, alpha 4 (antigen CD49D, alpha 4 subunit of VLA-4 receptor) |
| 205884_at | gb: NM_000885.2 /DEF = *Homo sapiens* integrin, alpha 4 (antigen CD49D, alpha 4 subunit of VLA-4 receptor) (ITGA4), mRNA. /FEA = mRNA /GEN = ITGA4 /PROD = integrin alpha 4 precursor /DB_XREF = 6006032 /UG = Hs. 40034 integrin, alpha 4 (antigen CD49D, alpha 4 subunit of VLA-4 receptor) /FL = gb: NM_000885.2 gb: L12002.1 |
| 204863_s_at | interleukin 6 signal transducer (gp130, oncostatin M receptor) |

TABLE V-continued

The 42-gene signature associated with circulating colon tumor cells

| | |
|---|---|
| 209795_at | gb: L07555.1 /DEF = *Homo sapiens* early activation antigen CD69 mRNA, complete cds. /FEA = mRNA /PROD = early activation antigen CD69 /DB_XREF = gi: 291897 /UG = Hs. 82401 CD69 antigen (p60, early T-cell activation antigen) /FL = gb: L07555.1 gb: NM_001781.1 |
| 209955_s_at | |

Figure 7:
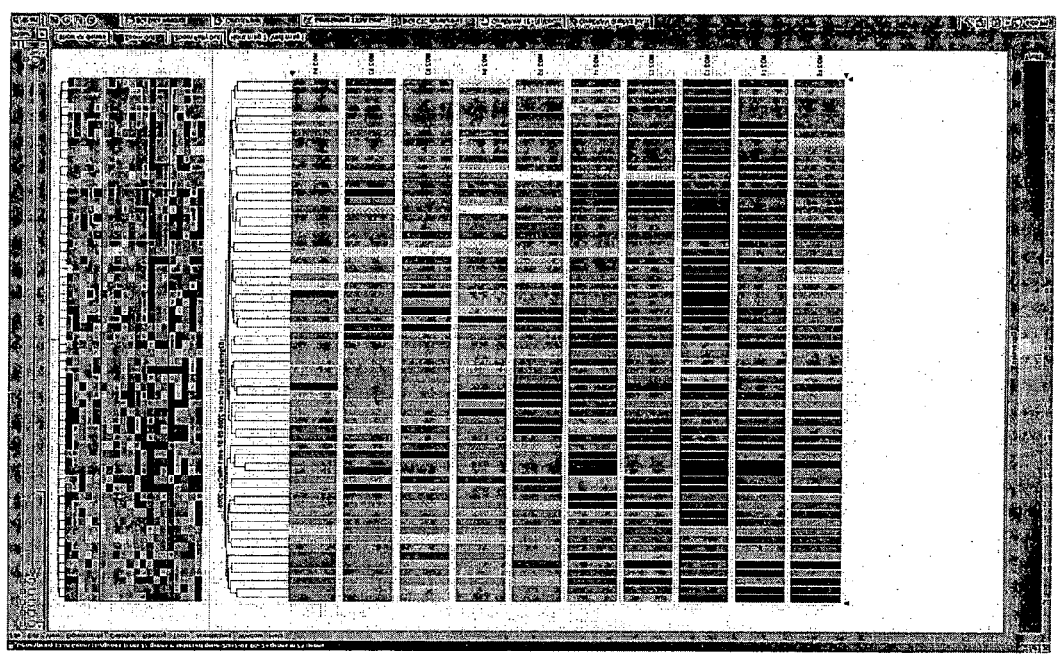
FIG. 7 is a colorgram of an enlarged breast CTC signature having 62 constituents.

Similarly, the breast CTC signatures that contain genes ranging from 62 down to 25 (FIG. 3; Table II) were used to positively distinguish breast from colon cancer samples (FIG. 7; Table VI). For example, when 62 genes were selected from the signature, the breast CTC signature discriminated a breast cancer from colon cancer sample.

TABLE VI

The 62-gene signature associated with circulating breast tumor cells

| | |
|---|---|
| 201130_s_at | gb: L08599.1 /DEF = Human uvomorulin (E-cadherin) (UVO) mRNA, complete cds. /FEA = mRNA /GEN = UVO /PROD = uvomorulin /DB_XREF = gi: 340184 /UG = Hs.194657 cadherin 1, type 1, E-cadherin (epithelial) /FL = gb: L08599.1 gb: NM_004360.1 |
| 201384_s_at | gb: NM_005899.1 /DEF = *Homo sapiens* membrane component, chromosome 17, surface marker 2 (ovarian carcinoma antigen CA125) (M17S2), mRNA. /FEA = mRNA /GEN = M17S2 /PROD = membrane component, chromosome 17, surfacemarker 2 (ovarian carcinoma antigen CA125) /DB_XREF = gi: 5174504 /UG = Hs.277721 membrane component, chromosome 17, surface marker 2 (ovarian carcinoma antigen CA125) /FL = gb: D30756.1 gb: NM_005899.1 |
| 202005_at | gb: NM_021978.1 /DEF = *Homo sapiens* suppression of tumorigenicity 14 (colon carcinoma, matriptase, epithin) (ST14), mRNA. /FEA = mRNA /GEN = ST14 /PROD = suppression of tumorigenicity 14 (coloncarcinoma, matriptase, epithin) /DB_XREF = gi: 11415039 /UG = Hs.56937 suppression of tumorigenicity 14 (colon carcinoma, matriptase, epithin) /FL = gb: AF057145.1 gb: NM_021978.1 gb: AB030036.1 gb: AF133086.1 gb: AF118224.2 |
| 202376_at | gb: NM_001085.2 /DEF = *Homo sapiens* serine (or cysteine) proteinase inhibitor, clade A (alpha-1 antiproteinase, antitrypsin), member 3 (SERPINA3), mRNA. /FEA = mRNA /GEN = SERPINA3 /PROD = alpha-1-antichymotrypsin, precursor /DB_XREF = gi: 9665246 /UG = Hs.234726 serine (or cysteine) proteinase inhibitor, clade A (alpha-1 antiproteinase, antitrypsin), member 3 /FL = gb: BC003559.1 gb: K01500.1 gb: NM_001085.2 |
| 203272_s_at | lung cancer candidate |
| 203325_s_at | collagen, type V, alpha 1 |
| 203757_s_at | gb: BC005008.1 /DEF = *Homo sapiens*, carcinoembryonic antigen-related cell adhesion molecule 6 (non-specific cross reacting antigen), clone MGC: 10467, mRNA, complete cds. /FEA = mRNA /PROD = carcinoembryonic antigen-related cell adhesionmolecule 6 (non-specific cross reacting antigen) /DB_XREF = gi: 13477106 /UG = Hs.73848 carcinoembryonic antigen-related cell adhesion molecule 6 (non-specific cross reacting antigen) /FL = gb: BC005008.1 gb: M18216.1 gb: M29541.1 gb: NM_002483.1 |
| 204268_at | gb: NM_005978.2 /DEF = *Homo sapiens* S100 calcium-binding protein A2 (S100A2), mRNA. /FEA = mRNA /GEN = S100A2 /PROD = S100 calcium-binding protein A2 /DB_XREF = gi: 9845513 /UG = Hs.38991 S100 calcium-binding protein A2 /FL = gb: BC002829.1 gb: NM_005978.2 |
| 204677_at | gb: NM_001795.1 /DEF = *Homo sapiens* cadherin 5, type 2, VE-cadherin (vascular epithelium) (CDH5), mRNA. /FEA = mRNA /GEN = CDH5 /PROD = cadherin 5, type 2, VE-cadherin (vascularepithelium) /DB_XREF = gi: 4502726 /UG = Hs.76206 cadherin 5, type 2, VE-cadherin (vascular epithelium) /FL = gb: U84722.1 gb: NM_001795.1 gb: AB035304.1 |
| 204975_at | gb: NM_001424.1 /DEF = *Homo sapiens* epithelial membrane protein 2 (EMP2), mRNA. /FEA = mRNA /GEN = EMP2 /PROD = epithelial membrane protein 2 /DB_XREF = gi: 4503560 /UG = Hs.29191 epithelial membrane protein 2 /FL = gb: U52100.1 gb: NM_001424.1 |
| 205778_at | gb: NM_005046.1 /DEF = *Homo sapiens* kallikrein 7 (chymotryptic, stratum corneum) (KLK7), mRNA. /FEA = mRNA /GEN = KLK7 /PROD = kallikrein 7 (chymotryptic, stratum corneum) /DB_XREF = gi: 4826949 /UG = Hs.151254 kallikrein 7 (chymotryptic, stratum corneum) /FL = gb: NM_005046.1 gb: L33404.1 |
| 205828_at | gb: NM_002422.2 /DEF = *Homo sapiens* matrix metalloproteinase 3 (stromelysin 1, progelatinase) (MMP3), mRNA. /FEA = mRNA /GEN = MMP3 /PROD = matrix metalloproteinase 3 preproprotein /DB_XREF = gi: 13027803 /UG = Hs.83326 matrix metalloproteinase 3 (stromelysin 1, progelatinase) /FL = gb: NM_002422.2 gb: J03209.1 |
| 205947_s_at | gb: NM_003382.1 /DEF = *Homo sapiens* vasoactive intestinal peptide receptor 2 (VIPR2), mRNA. /FEA = mRNA /GEN = VIPR2 /PROD = vasoactive intestinal peptide receptor 2 /DB_XREF = gi: 4507898 /UG = Hs.2126 vasoactive intestinal peptide receptor 2 /FL = gb: NM_003382.1 gb: L36566.1 |
| 206079_at | gb: NM_001821.1 /DEF = *Homo sapiens* choroideremia-like (Rab escort protein 2) (CHML), mRNA. /FEA = mRNA /GEN = CHML /PROD = choroideremia-like |

TABLE VI-continued

The 62-gene signature associated with circulating breast tumor cells

| | |
|---|---|
| | Rab escort protein 2 /DB_XREF = gi: 4502810 /UG = Hs.170129 choroideremia-like (Rab escort protein 2) /FL = gb: NM_001821.1 |
| 206093_x_at | gb: NM_007116.1 /DEF = Homo sapiens tenascin XA (TNXA), mRNA. /FEA = mRNA /GEN = TNXA /PROD = tenascin XA /DB_XREF = gi: 6005907 /UG = Hs.283750 tenascin XA /FL = gb: U24488.1 gb: NM_007116.1 |
| 206325_at | gb: NM_001756.2 /DEF = Homo sapiens serine (or cysteine) proteinase inhibitor, clade A (alpha-1 antiproteinase, antitrypsin), member 6 (SERPINA6), mRNA. /FEA = mRNA /GEN = SERPINA6 /PROD = corticosteroid binding globulin precursor /DB_XREF = gi: 4580418 /UG = Hs.1305 serine (or cysteine) proteinase inhibitor, clade A (alpha-1 antiproteinase, antitrypsin), member 6 /FL = gb: J02943.1 gb: NM_001756.2 |
| 206517_at | gb: NM_004062.1 /DEF = Homo sapiens cadherin 16, KSP-cadherin (CDH16), mRNA. /FEA = mRNA /GEN = CDH16 /PROD = cadherin 16, KSP-cadherin /DB_XREF = gi: 4757955 /UG = Hs.115418 cadherin 16, KSP-cadherin /FL = gb: AF016272.1 gb: NM_004062.1 |
| 206676_at | gb: M33326.1 /DEF = Human nonspecific cross-reacting antigen (NCA) mRNA, complete cds. /FEA = mRNA /GEN = NCA /PROD = non-specific cross reacting antigen /DB_XREF = gi: 189101 /UG = Hs.41 carcinoembryonic antigen-related cell adhesion molecule 8 /FL = gb: M33326.1 gb: NM_001816.1 |
| 206939_at | gb: NM_005215.1 /DEF = Homo sapiens deleted in colorectal carcinoma (DCC), mRNA. /FEA = mRNA /GEN = DCC /PROD = deleted in colorectal carcinoma /DB_XREF = gi: 4885174 /UG = Hs.211567 deleted in colorectal carcinoma /FL = gb: NM_005215.1 |
| 207329_at | gb: NM_002424.1 /DEF = Homo sapiens matrix metalloproteinase 8 (neutrophil collagenase) (MMP8), mRNA. /FEA = mRNA /GEN = MMP8 /PROD = matrix metalloproteinase 8 preproprotein /DB_XREF = gi: 4505220 /UG = Hs.73862 matrix metalloproteinase 8 (neutrophil collagenase) /FL = gb: J05556.1 gb: NM_002424.1 |
| 207652_s_at | gb: NM_004072.1 /DEF = Homo sapiens chemokine-like receptor 1 (CMKLR1), mRNA. /FEA = mRNA /GEN = CMKLR1 /PROD = chemokine-like receptor 1 /DB_XREF = gi: 4758013 /UG = Hs.159553 chemokine-like receptor 1 /FL = gb: U79527.1 gb: NM_004072.1 |
| 207793_s_at | gb: NM_004437.1 /DEF = Homo sapiens erythrocyte membrane protein band 4.1 (elliptocytosis 1, RH-linked) (EPB41), mRNA. /FEA = mRNA /GEN = EPB41 /PROD = erythrocyte membrane protein band 4.1(elliptocytosis 1, RH-linked) /DB_XREF = gi: 4758273 /UG = Hs.37427 erythrocyte membrane protein band 4.1 (elliptocytosis 1, RH-linked) /FL = gb: M14993.1 gb: NM_004437.1 |
| 207811_at | gb: NM_000223.1 /DEF = Homo sapiens keratin 12 (Meesmann corneal dystrophy) (KRT12), mRNA. /FEA = mRNA /GEN = KRT12 /PROD = keratin 12 /DB_XREF = gi: 4557698 /UG = Hs.66739 keratin 12 (Meesmann corneal dystrophy) /FL = gb: D78367.1 gb: NM_000223.1 |
| 207847_s_at | gb: NM_002456.1 /DEF = Homo sapiens mucin 1, transmembrane (MUC1), mRNA. /FEA = mRNA /GEN = MUC1 /PROD = mucin 1, transmembrane /DB_XREF = gi: 4505282 /UG = Hs.89603 mucin 1, transmembrane /FL = gb: NM_002456.1 |
| 208267_at | gb: NM_019841.1 /DEF = Homo sapiens epithelial calcium channel 1 (ECAC1), mRNA. /FEA = mRNA /GEN = ECAC1 /PROD = epithelial calcium channel 1 /DB_XREF = gi: 9789940 /UG = Hs.283369 epithelial calcium channel 1 /FL = gb: NM_019841.1 |
| 208401_s_at | gb: U01157.1 /DEF = Human glucagon-like peptide-1 receptor mRNA with CA dinucleotide repeat, complete cds. /FEA = mRNA /PROD = glucagon-like peptide-1 receptor /DB_XREF = gi: 684918 /UG = Hs.165 glucagon-like peptide 1 receptor /FL = gb: U01104.1 gb: NM_002062.1 gb: U01157.1 gb: U10037.1 |
| 209422_at | Consensus includes gb: AL109965 /DEF = Human DNA sequence from clone RP5-1121G12 on chromosome 20 Contains the 3 end of a gene encoding two isoforms (the hepatocellular carcinoma-associated antigen 58 (HCA58) and a putative novel protein containing a PHD finger domain), the SCAND1 gen . . . /FEA = mRNA_2 /DB_XREF = gi: 9663113 /UG = Hs.112594 hypothetical protein DKFZp434F0272 /FL = gb: AY027523.1 gb: AF348207.1 |
| 209955_s_at | gb: U76833.1 /DEF = Human integral membrane serine protease Seprase mRNA, complete cds. /FEA = mRNA /PROD = integral membrane serine protease Seprase /DB_XREF = gi: 1924981 /UG = Hs.418 fibroblast activation protein, alpha /FL = gb: U09278.1 gb: U76833.1 gb: NM_004460.1 |
| 210204_s_at | gb: U71268.1 /DEF = Human potential transcriptional repressor NOT4Hp (NOT4H) mRNA, complete cds. /FEA = mRNA /GEN = NOT4H /PROD = potential transcriptional repressor NOT4Hp /DB_XREF = gi: 4097899 /UG = Hs.20423 CCR4-NOT transcription complex, subunit 4 /FL = gb: U71268.1 |
| 210523_at | gb: D89675.1 /DEF = Homo sapiens mRNA for bone morphogenetic protein type IB receptor, complete cds. /FEA = mRNA /PROD = bone morphogenetic protein type IB receptor /DB_XREF = gi: 2055308 /UG = Hs.87223 bone morphogenetic protein receptor, type IB /FL = gb: D89675.1 gb: U89326.1 gb: NM_001203.1 |
| 210989_at | gb: U77706.1 /DEF = Human laminin alpha 4 chain (LAMA4*-1) mRNA, complete cds. /FEA = mRNA /GEN = LAMA4*-1 /PROD = laminin alpha 4 chain /DB_XREF = gi: 1684836 /UG = Hs.78672 laminin, alpha 4 /FL = gb: U77706.1 |
| 211227_s_at | gb: AF332216.1 /DEF = Homo sapiens chromosome Y protocadherin 11 (PCDH11) mRNA, complete cds, alternatively spliced. /FEA = mRNA /GEN = PCDH11 /PROD = protocadherin 11 /DB_XREF = gi: 13161056 /UG = Hs.159156 protocadherin 11 /FL = gb: AF332216.1 |

TABLE VI-continued

The 62-gene signature associated with circulating breast tumor cells

| | |
|---|---|
| 211478_s_at | gb: M74777.1 /DEF = Human dipeptidyl peptidase IV (CD26) mRNA, complete cds. /FEA = mRNA /GEN = CD26 /PROD = dipeptidyl peptidase IV /DB_XREF = gi: 180082 /UG = Hs.44926 dipeptidylpeptidase IV (CD26, adenosine deaminase complexing protein 2) /FL = gb: M74777.1 |
| 211925_s_at | gb: AY004175.1 /DEF = *Homo sapiens* phospholipase C beta 1 mRNA, complete cds. /FEA = CDS /PROD = phospholipase C beta 1 /DB_XREF = gi: 9438228 /UG = Hs.41143 phosphoinositide-specific phospholipase C-beta 1 /FL = gb: AY004175.1 |
| 212067_s_at | complement component 1, r subcomponent |
| 212097_at | caveolin 1, caveolae protein, 22 kDa |
| 213285_at | ESTs, Weakly similar to MUC2_HUMAN Mucin 2 precursor (Intestinal mucin 2) [*H. sapiens*] |
| 213693_s_at | mucin 1, transmembrane |
| 213992_at | collagen, type IV, alpha 6 |
| 214031_s_at | keratin 7 |
| 214580_x_at | keratin 6A |
| 215878_at | integrin, beta 1 (fibronectin receptor, beta polypeptide, antigen CD29 includes MDF2, MSK12) |
| 216190_x_at | integrin, beta 1 (fibronectin receptor, beta polypeptide, antigen CD29 includes MDF2, MSK12) |
| 216333_x_at | Consensus includes gb: M25813.1 /DEF = Human unidentified gene complementary to P450c21 gene, partial cds. /FEA = mRNA /DB_XREF = gi: 183069 /UG = Hs.283750 tenascin XA |
| 216812_at | Consensus includes gb: AF308291.1 /DEF = *Homo sapiens* serologically defined breast cancer antigen NY-BR-46 mRNA, partial cds. /FEA = mRNA /PROD = serologically defined breast cancer antigenNY-BR-46 /DB_XREF = gi: 12060833 /UG = Hs.307075 *Homo sapiens* serologically defined breast cancer antigen NY-BR-46 mRNA, partial cds |
| 216921_s_at | Consensus includes gb: X90763.1 /DEF = *Homo sapiens* mRNA for type I keratin. /FEA = mRNA /GEN = hHa5 /PROD = HHa5 hair keratin type I intermediate filament /DB_XREF = gi: 1668743 /UG = Hs.73082 keratin, hair, acidic, 5 |
| 217291_at | *H. sapiens* carcinoembryonic antigen gene. |
| 217557_s_at | carboxypeptidase M |
| 217728_at | gb: NM_014624.2 /DEF = *Homo sapiens* S100 calcium-binding protein A6 (calcyclin) (S100A6), mRNA. /FEA = mRNA /GEN = S100A6 /PROD = S100 calcium-binding protein A6 /DB_XREF = gi: 9845517 /UG = Hs.275243 S100 calcium-binding protein A6 (calcyclin) /FL = gb: BC001431.1 gb: NM_014624.2 |
| 218649_x_at | gb: NM_004713.1 /DEF = *Homo sapiens* serologically defined colon cancer antigen 1 (SDCCAG1), mRNA. /FEA = mRNA /GEN = SDCCAG1 /PROD = serologically defined colon cancer antigen 1 /DB_XREF = gi: 4759077 /UG = Hs.54900 serologically defined colon cancer antigen 1 /FL = gb: AF039687.1 gb: NM_004713.1 |
| 219151_s_at | gb: NM_007081.1 /DEF = *Homo sapiens* RAB, member of RAS oncogene family-like 2B (RABL2B), mRNA. /FEA = mRNA /GEN = RABL2B /PROD = RAB, member of RAS oncogene family-like 2B /DB_XREF = gi: 5902039 /UG = Hs.145409 RAB, member of RAS oncogene family-like 2B /FL = gb: AF095352.1 gb: NM_007081.1 |
| 219297_at | gb: NM_019045.1 /DEF = *Homo sapiens* similar to rab11-binding protein (FLJ11116), mRNA. /FEA = mRNA /GEN = FLJ11116 /PROD = similar to rab11-binding protein /DB_XREF = gi: 9506636 /UG = Hs.98510 similar to rab11-binding protein /FL = gb: NM_019045.1 |
| 219436_s_at | gb: NM_016242.1 /DEF = *Homo sapiens* endomucin-2 (LOC51705), mRNA. /FEA = mRNA /GEN = LOC51705 /PROD = endomucin-2 /DB_XREF = gi: 7706452 /UG = Hs.41135 endomucin-2 /FL = gb: AB034695.1 gb: NM_016242.1 |
| 219630_at | gb: AF205940.1 gb: NM_005764.1 /DEF = *Homo sapiens* epithelial protein up-regulated in carcinoma, membrane associated protein 17 (DD96), mRNA. /FEA = mRNA /GEN = DD96 /PROD = epithelial protein up-regulated in carcinoma, membrane associated protein 17 /DB_XREF = gi: 5031656 /UG = Hs.271473 epithelial protein up-regulated in carcinoma, membrane associated protein 17 /FL = gb: NM_005764.1 |
| 220120_s_at | gb: NM_022140.1 /DEF = *Homo sapiens* erythrocyte protein band 4.1-like 4 (EPB41L4), mRNA. /FEA = mRNA /GEN = EPB41L4 /PROD = erythrocyte protein band 4.1-like 4 /DB_XREF = gi: 11545876 /UG = Hs.104746 erythrocyte protein band 4.1-like 4 /FL = gb: AB030240.1 gb: NM_022140.1 |
| 220249_at | gb: NM_012269.1 /DEF = *Homo sapiens* hyaluronoglucosaminidase 4 (HYAL4), mRNA. /FEA = mRNA /GEN = HYAL4 /PROD = hyaluronoglucosaminidase 4 /DB_XREF = gi: 6912427 /UG = Hs.28673 hyaluronoglucosaminidase 4 /FL = gb: AF009010.1 gb: NM_012269.1 |
| 220500_s_at | gb: NM_007082.2 /DEF = *Homo sapiens* RAB, member of RAS oncogene family-like 2A (RABL2A), mRNA. /FEA = mRNA /GEN = RABL2A /PROD = RAB, member of RAS oncogene family-like 2A /DB_XREF = gi: 7549818 /UG = Hs.122660 RAB, member of RAS oncogene family-like 2A /FL = gb: AF095350.1 gb: NM_007082.2 |
| 220745_at | gb: NM_013371.1 /DEF = *Homo sapiens* interleukin 19 (IL19), mRNA. /FEA = mRNA /GEN = IL19 /PROD = interleukin 19 /DB_XREF = gi: 7019574 /UG = Hs.71979 interleukin 19 /FL = gb: AF192498.1 gb: NM_013371.1 |

TABLE VI-continued

The 62-gene signature associated with circulating breast tumor cells

| | |
|---|---|
| 221798_x_at | cadherin 1, type 1, E-cadherin (epithelial) |
| 221902_at | ESTs, Weakly similar to A43932 mucin 2 precursor, intestinal - human (fragments) [*H. sapiens*] |
| 221947_at | interleukin 17 receptor C |
| 222277_at | ESTs, Weakly similar to CGHU7L collagen alpha 1(III) chain precursor - human [*H. sapiens*] |

Figure 8:
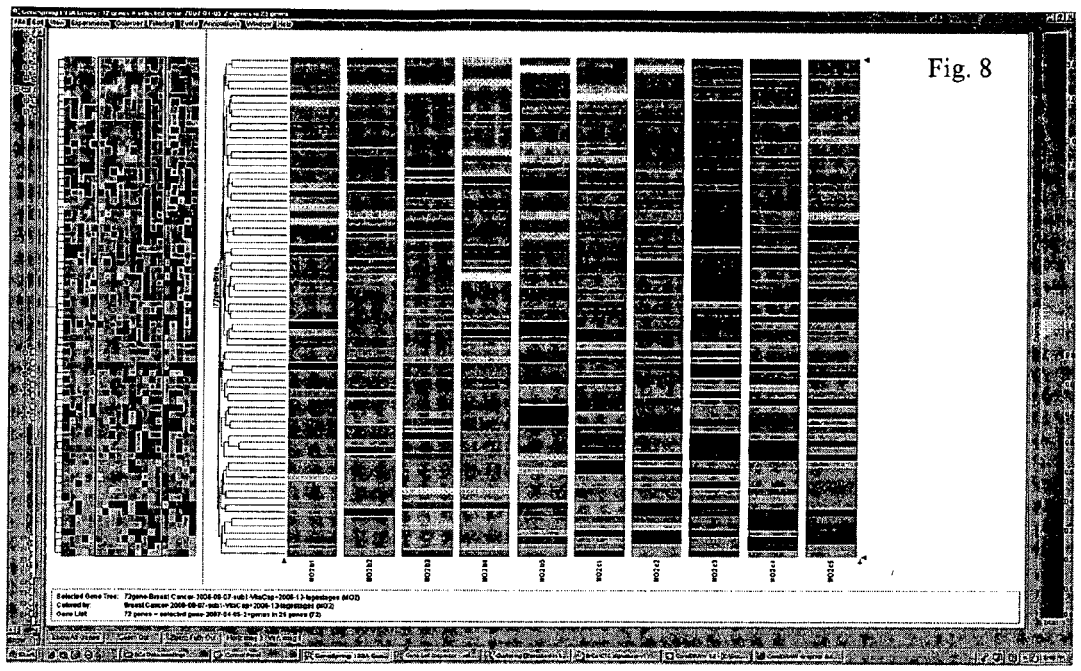
FIG. 8 is a colorgram of an enlarged breast CTC signature having 72 constituents.

However, when greater than 62 genes were selected, their expression profiles could no longer discriminate between colon and breast cancer samples. For example, when 72 genes were selected from the initial gene set (FIG. 8; Table VII), the expression profiles of the 72 genes could not discriminate a breast cancer from colon cancer sample.

TABLE VII

Increase gene number to 72 genes loses the specificity in the breast CTC signature

| | |
|---|---|
| 222277_at | ESTs, Weakly similar to CGHU7L collagen alpha 1(III) chain precursor - human [*H. sapiens*] |
| 221947_at | interleukin 17 receptor C |
| 221902_at | ESTs, Weakly similar to A43932 mucin 2 precursor, intestinal - human (fragments) [*H. sapiens*] |
| 221115_s_at | gb: NM_018655.1 /DEF = *Homo sapiens* lens epithelial protein (LEP503), mRNA. /FEA = mRNA /GEN = LEP503 /PROD = lens epithelial protein /DB_XREF = gi: 8923829 /UG = Hs.272399 lens epithelial protein /FL = gb: AF268478.1 gb: NM_018655.1 |
| 220745_at | gb: NM_013371.1 /DEF = *Homo sapiens* interleukin 19 (IL19), mRNA. /FEA = mRNA /GEN = IL19 /PROD = interleukin 19 /DB_XREF = gi: 7019574 /UG = Hs.71979 interleukin 19 /FL = gb: AF192498.1 gb: NM_013371.1 |
| 220500_s_at | gb: NM_007082.2 /DEF = *Homo sapiens* RAB, member of RAS oncogene family-like 2A (RABL2A), mRNA. /FEA = mRNA /GEN = RABL2A /PROD = RAB, member of RAS oncogene family-like 2A /DB_XREF = gi: 7549818 /UG = Hs.122660 RAB, member of RAS oncogene family-like 2A /FL = gb: AF095350.1 gb: NM_007082.2 |
| 220249_at | gb: NM_012269.1 /DEF = *Homo sapiens* hyaluronoglucosaminidase 4 (HYAL4), mRNA. /FEA = mRNA /GEN = HYAL4 /PROD = hyaluronoglucosaminidase 4 /DB_XREF = gi: 6912427 /UG = Hs.28673 hyaluronoglucosaminidase 4 /FL = gb: AF009010.1 gb: NM_012269.1 |
| 220120_s_at | gb: NM_022140.1 /DEF = *Homo sapiens* erythrocyte protein band 4.1-like 4 (EPB41L4), mRNA. /FEA = mRNA /GEN = EPB41L4 /PROD = erythrocyte protein band 4.1-like 4 /DB_XREF = gi: 11545876 /UG = Hs.104746 erythrocyte protein band 4.1-like 4 /FL = gb: AB030240.1 gb: NM_022140.1 |
| 219630_at | gb: NM_005764.1 /DEF = *Homo sapiens* epithelial protein up-regulated in carcinoma, membrane associated protein 17 (DD96), mRNA. /FEA = mRNA /GEN = DD96 /PROD = epithelial protein up-regulated in carcinoma, membrane associated protein 17 /DB_XREF = gi: 5031656 /UG = Hs.271473 epithelial protein up-regulated in carcinoma, membrane associated protein 17 /FL = gb: NM_005764.1 |
| 219436_s_at | gb: NM_016242.1 /DEF = *Homo sapiens* endomucin-2 (LOC51705), mRNA. /FEA = mRNA /GEN = LOC51705 /PROD = endomucin-2 /DB_XREF = gi: 7706452 /UG = Hs.41135 endomucin /FL = gb: AB034695.1 gb: NM_016242.1 gb: AF205940.1 |
| 219297_at | gb: NM_019045.1 /DEF = *Homo sapiens* similar to rab11-binding protein (FLJ11116), mRNA. /FEA = mRNA /GEN = FLJ11116 /PROD = similar to rab11-binding protein /DB_XREF = gi: 9506636 /UG = Hs.98510 similar to rab11-binding protein /FL = gb: NM_019045.1 |
| 219213_at | gb: NM_021219.1 /DEF = *Homo sapiens* vascular endothelial junction-associated molecule (VE-JAM), mRNA. /FEA = mRNA /GEN = VE-JAM /PROD = vascular endothelial junction-associatedmolecule /DB_XREF = gi: 10864028 /UG = Hs.54650 vascular endothelial junction-associated molecule /FL = gb: NM_021219.1 gb: AY016009.1 gb: AF255910.1 |
| 219151_s_at | gb: NM_007081.1 /DEF = *Homo sapiens* RAB, member of RAS oncogene family-like 2B (RABL2B), mRNA. /FEA = mRNA /GEN = RABL2B /PROD = RAB, member of RAS oncogene family-like 2B /DB_XREF = gi: 5902039 /UG = Hs.145409 RAB, member of RAS oncogene family-like 2B /FL = gb: AF095352.1 gb: NM_007081.1 |
| 218649_x_at | gb: NM_004713.1 /DEF = *Homo sapiens* serologically defined colon cancer antigen 1 (SDCCAG1), mRNA. /FEA = mRNA /GEN = SDCCAG1 /PROD = serologically defined colon cancer antigen 1 /DB_XREF = gi: 4759077 /UG = Hs.54900 serologically defined colon cancer antigen 1 /FL = gb: AF039687.1 gb: NM_004713.1 |
| 217728_at | gb: NM_014624.2 /DEF = *Homo sapiens* S100 calcium-binding protein A6 (calcyclin) (S100A6), mRNA. /FEA = mRNA /GEN = S100A6 /PROD = S100 calcium-binding protein A6 /DB_XREF = gi: 9845517 /UG = Hs.275243 S100 calcium-binding protein A6 (calcyclin) /FL = gb: BC001431.1 gb: NM_014624.2 |
| 217557_s_at | carboxypeptidase M |
| 217291_at | *H. sapiens* carcinoembryonic antigen gene. |

TABLE VII-continued

Increase gene number to 72 genes loses the specificity in the breast CTC signature

| | |
|---|---|
| 216921_s_at | Consensus includes gb: X90763.1 /DEF = *Homo sapiens* mRNA for type I keratin. /FEA = mRNA /GEN = hHa5 /PROD = HHa5 hair keratin type I intermediate filament /DB_XREF = gi: 1668743 /UG = Hs.73082 keratin, hair, acidic, 5 |
| 216904_at | Consensus includes gb: X15880.1 /DEF = Human mRNA for collagen VI alpha-1 C-terminal globular domain. /FEA = mRNA /PROD = alpha-1 collagen VI (AA 574-1009) /DB_XREF = gi: 30029 /UG = Hs.108885 collagen, type VI, alpha 1 |
| 216812_at | Consensus includes gb: AF308291.1 /DEF = *Homo sapiens* serologically defined breast cancer antigen NY-BR-46 mRNA, partial cds. /FEA = mRNA /PROD = serologically defined breast cancer antigenNY-BR-46 /DB_XREF = gi: 12060833 /UG = Hs.307075 *Homo sapiens* serologically defined breast cancer antigen NY-BR-46 mRNA, partial cds |
| 216622_at | Consensus includes gb: AF029325.1 /DEF = *Homo sapiens* laminin beta-4 chain precursor (LAMB4) mRNA, alternatively spliced short variant, partial cds. /FEA = mRNA /GEN = LAMB4 /PROD = laminin beta-4 chain precursor /DB_XREF = gi: 4003504 /UG = Hs.202688 laminin, beta 4 |
| 216470_x_at | Consensus includes gb: AF009664 /DEF = *Homo sapiens* T cell receptor beta locus, 3 trypsinogen repeats /FEA = CDS_1 /DB_XREF = gi: 2275594 /UG = Hs.303157 T cell receptor beta locus |
| 216333_x_at | Consensus includes gb: M25813.1 /DEF = Human unidentified gene complementary to P450c21 gene, partial cds. /FEA = mRNA /DB_XREF = gi: 183069 /UG = Hs.283750 tenascin XA |
| 216298_at | T cell receptor gamma locus |
| 216190_x_at | integrin, beta 1 (fibronectin receptor, beta polypeptide, antigen CD29 includes MDF2, MSK12) |
| 215723_s_at | Consensus includes gb: AJ276230.1 /DEF = *Homo sapiens* mRNA for partial phospholipase D1, splice variant PLD1ab2. /FEA = mRNA /GEN = PLD1 /PROD = phospholipase D1 /DB_XREF = gi: 7161182 /UG = Hs.82587 phospholipase D1, phophatidylcholine-specific |
| 214580_x_at | keratin 6A |
| 214031_s_at | keratin 7 |
| 213992_at | collagen, type IV, alpha 6 |
| 213693_s_at | mucin 1, transmembrane |
| 213285_at | ESTs, Weakly similar to MUC2_HUMAN Mucin 2 precursor (Intestinal mucin 2) [*H. sapiens*] |
| 212097_at | caveolin 1, caveolae protein, 22 kDa |
| 212067_s_at | complement component 1, r subcomponent |
| 211925_s_at | gb: AY004175.1 /DEF = *Homo sapiens* phospholipase C beta 1 mRNA, complete cds. /FEA = CDS /PROD = phospholipase C beta 1 /DB_XREF = gi: 9438228 /UG = Hs.41143 phosphoinositide-specific phospholipase C-beta 1 /FL = gb: AY004175.1 |
| 211227_s_at | gb: AF332216.1 /DEF = *Homo sapiens* chromosome Y protocadherin 11 (PCDH11) mRNA, complete cds, alternatively spliced. /FEA = mRNA /GEN = PCDH11 /PROD = protocadherin 11 /DB_XREF = gi: 13161056 /UG = Hs.159156 protocadherin 11 /FL = gb: AF332216.1 |
| 210989_at | gb: U77706.1 /DEF = Human laminin alpha 4 chain (LAMA4*-1) mRNA, complete cds. /FEA = mRNA /GEN = LAMA4*-1 /PROD = laminin alpha 4 chain /DB_XREF = gi: 1684836 /UG = Hs. 78672 laminin, alpha 4 /FL = gb: U77706.1 |
| 210523_at | gb: D89675.1 /DEF = *Homo sapiens* mRNA for bone morphogenetic protein type IB receptor, complete cds. /FEA = mRNA /PROD = bone morphogenetic protein type IB receptor /DB_XREF = gi: 2055308 /UG = Hs.87223 bone morphogenetic protein receptor, type IB /FL = gb: D89675.1 gb: U89326.1 gb: NM_001203.1 |
| 210292_s_at | gb: AF332218.1 /DEF = *Homo sapiens* chromosome X protocadherin 11 (PCDH11) mRNA, complete cds, alternatively spliced. /FEA = mRNA /GEN = PCDH11 /PROD = protocadherin 11 /DB_XREF = gi: 13161062 /UG = Hs.159156 protocadherin 11 /FL = gb: AF332218.1 |
| 210204_s_at | gb: U71268.1 /DEF = Human potential transcriptional repressor NOT4Hp (NOT4H) mRNA, complete cds. /FEA = mRNA /GEN = NOT4H /PROD = potential transcriptional repressor NOT4Hp /DB_XREF = gi: 4097899 /UG = Hs.20423 CCR4-NOT transcription complex, subunit 4 /FL = gb: U71268.1 |
| 209536_s_at | gb: AF320070.1 /DEF = *Homo sapiens* hepatocellular carcinoma-associated protein HCA10 mRNA, complete cds. /FEA = mRNA /PROD = hepatocellular carcinoma-associated proteinHCA10 /DB_XREF = gi: 11386004 /UG = Hs.55058 EH-domain containing 4 /FL = gb: AF307137.1 gb: AF320070.1 gb: AF323924.1 |
| 209422_at | Consensus includes gb: AL109965 /DEF = Human DNA sequence from clone RP5-1121G12 on chromosome 20 Contains the 3 end of a gene encoding two isoforms (the hepatocellular carcinoma-associated antigen 58 (HCA58) and a putative novel protein containing a PHD finger domain), the SCAND1 gen . . . /FEA = mRNA_2 /DB_XREF = gi: 9663113 /UG = Hs.112594 hypothetical protein DKFZp434F0272 /FL = gb: AY027523.1 gb: AF348207.1 |
| 208267_at | gb: NM_019841.1 /DEF = *Homo sapiens* epithelial calcium channel 1 (ECAC1), mRNA. /FEA = mRNA /GEN = ECAC1 /PROD = epithelial calcium channel 1 /DB_XREF = gi: 9789940 /UG = Hs.283369 epithelial calcium channel 1 /FL = gb: NM_019841.1 |
| 207847_s_at | gb: NM_002456.1 /DEF = *Homo sapiens* mucin 1, transmembrane (MUC1), mRNA. /FEA = mRNA /GEN = MUC1 /PROD = mucin 1, transmembrane /DB_XREF = gi: 4505282 /UG = Hs.89603 mucin 1, transmembrane /FL = gb: NM_002456.1 |

TABLE VII-continued

Increase gene number to 72 genes loses the specificity in the breast CTC signature

| | |
|---|---|
| 207811_at | gb: NM_000223.1 /DEF = Homo sapiens keratin 12 (Meesmann corneal dystrophy) (KRT12), mRNA. /FEA = mRNA /GEN = KRT12 /PROD = keratin 12 /DB_XREF = gi: 4557698 /UG = Hs.66739 keratin 12 (Meesmann corneal dystrophy) /FL = gb: D78367.1 gb: NM_000223.1 |
| 207793_s_at | gb: NM_004437.1 /DEF = Homo sapiens erythrocyte membrane protein band 4.1 (elliptocytosis 1, RH-linked) (EPB41), mRNA. /FEA = mRNA /GEN = EPB41 /PROD = erythrocyte membrane protein band 4.1(elliptocytosis 1, RH-linked) /DB_XREF = gi: 4758273 /UG = Hs.37427 erythrocyte membrane protein band 4.1 (elliptocytosis 1, RH-linked) /FL = gb: M14993.1 gb: NM_004437.1 |
| 207652_s_at | gb: NM_004072.1 /DEF = Homo sapiens chemokine-like receptor 1 (CMKLR1), mRNA. /FEA = mRNA /GEN = CMKLR1 /PROD = chemokine-like receptor 1 /DB_XREF = gi: 4758013 /UG = Hs.159553 chemokine-like receptor 1 /FL = gb: U79527.1 gb: NM_004072.1 |
| 207329_at | gb: NM_002424.1 /DEF = Homo sapiens matrix metalloproteinase 8 (neutrophil collagenase) (MMP8), mRNA. /FEA = mRNA /GEN = MMP8 /PROD = matrix metalloproteinase 8 preproprotein /DB_XREF = gi: 4505220 /UG = Hs.73862 matrix metalloproteinase 8 (neutrophil collagenase) /FL = gb: J05556.1 gb: NM_002424.1 |
| 206939_at | gb: NM_005215.1 /DEF = Homo sapiens deleted in colorectal carcinoma (DCC), mRNA. /FEA = mRNA /GEN = DCC /PROD = deleted in colorectal carcinoma /DB_XREF = gi: 4885174 /UG = Hs.211567 deleted in colorectal carcinoma /FL = gb: NM_005215.1 |
| 206676_at | gb: M33326.1 /DEF = Human nonspecific cross-reacting antigen (NCA) mRNA, complete cds. /FEA = mRNA /GEN = NCA /PROD = non-specific cross reacting antigen /DB_XREF = gi: 189101 /UG = Hs.41 carcinoembryonic antigen-related cell adhesion molecule 8 /FL = gb: M33326.1 gb: NM_001816.1 |
| 206517_at | gb: NM_004062.1 /DEF = Homo sapiens cadherin 16, KSP-cadherin (CDH16), mRNA. /FEA = mRNA /GEN = CDH16 /PROD = cadherin 16, KSP-cadherin /DB_XREF = gi: 4757955 /UG = Hs.115418 cadherin 16, KSP-cadherin /FL = gb: AF016272.1 gb: NM_004062.1 |
| 206325_at | gb: NM_001756.2 /DEF = Homo sapiens serine (or cysteine) proteinase inhibitor, clade A (alpha-1 antiproteinase, antitrypsin), member 6 (SERPINA6), mRNA. /FEA = mRNA /GEN = SERPINA6 /PROD = corticosteroid binding globulin precursor /DB_XREF = gi: 4580418 /UG = Hs.1305 serine (or cysteine) proteinase inhibitor, clade A (alpha-1 antiproteinase, antitrypsin), member 6 /FL = gb: J02943.1 gb: NM_001756.2 |
| 206093_x_at | gb: NM_007116.1 /DEF = Homo sapiens tenascin XA (TNXA), mRNA. /FEA = mRNA /GEN = TNXA /PROD = tenascin XA /DB_XREF = gi: 6005907 /UG = Hs.283750 tenascin XA /FL = gb: U24488.1 gb: NM_007116.1 |
| 206079_at | gb: NM_001821.1 /DEF = Homo sapiens choroideremia-like (Rab escort protein 2) (CHML), mRNA. /FEA = mRNA /GEN = CHML /PROD = choroideremia-like Rab escort protein 2 /DB_XREF = gi: 4502810 /UG = Hs.170129 choroideremia-like (Rab escort protein 2) /FL = gb: NM_001821.1 |
| 205947_s_at | gb: NM_003382.1 /DEF = Homo sapiens vasoactive intestinal peptide receptor 2 (VIPR2), mRNA. /FEA = mRNA /GEN = VIPR2 /PROD = vasoactive intestinal peptide receptor 2 /DB_XREF = gi: 4507898 /UG = Hs.2126 vasoactive intestinal peptide receptor 2 /FL = gb: NM_003382.1 gb: L36566.1 |
| 205828_at | gb: NM_002422.2 /DEF = Homo sapiens matrix metalloproteinase 3 (stromelysin 1, progelatinase) (MMP3), mRNA. /FEA = mRNA /GEN = MMP3 /PROD = matrix metalloproteinase 3 preproprotein /DB_XREF = gi: 13027803 /UG = Hs.83326 matrix metalloproteinase 3 (stromelysin 1, progelatinase) /FL = gb: NM_002422.2 gb: J03209.1 |
| 205778_at | gb: NM_005046.1 /DEF = Homo sapiens kallikrein 7 (chymotryptic, stratum corneum) (KLK7), mRNA. /FEA = mRNA /GEN = KLK7 /PROD = kallikrein 7 (chymotryptic, stratum corneum) /DB_XREF = gi: 4826949 /UG = Hs.151254 kallikrein 7 (chymotryptic, stratum corneum) /FL = gb: NM_005046.1 gb: L33404.1 |
| 204975_at | gb: NM_001424.1 /DEF = Homo sapiens epithelial membrane protein 2 (EMP2), mRNA. /FEA = mRNA /GEN = EMP2 /PROD = epithelial membrane protein 2 /DB_XREF = gi: 4503560 /UG = Hs.29191 epithelial membrane protein 2 /FL = gb: U52100.1 gb: NM_001424.1 |
| 204677_at | gb: NM_001795.1 /DEF = Homo sapiens cadherin 5, type 2, VE-cadherin (vascular epithelium) (CDH5), mRNA. /FEA = mRNA /GEN = CDH5 /PROD = cadherin 5, type 2, VE-cadherin (vascularepithelium) /DB_XREF = gi: 4502726 /UG = Hs.76206 cadherin 5, type 2, VE-cadherin (vascular epithelium) /FL = gb: U84722.1 gb: NM_001795.1 gb: AB035304.1 |
| 204268_at | gb: NM_005978.2 /DEF = Homo sapiens S100 calcium-binding protein A2 (S100A2), mRNA. /FEA = mRNA /GEN = S100A2 /PROD = S100 calcium-binding protein A2 /DB_XREF = gi: 9845513 /UG = Hs.38991 S100 calcium-binding protein A2 /FL = gb: BC002829.1 gb: NM_005978.2 |
| 203757_s_at | gb: BC005008.1 /DEF = Homo sapiens, carcinoembryonic antigen-related cell adhesion molecule 6 (non-specific cross reacting antigen), clone MGC: 10467, mRNA, complete cds. /FEA = mRNA /PROD = carcinoembryonic antigen-related cell adhesionmolecule 6 (non-specific cross reacting antigen) /DB_XREF = gi: 13477106 /UG = Hs.73848 carcinoembryonic antigen-related cell adhesion molecule 6 (non-specific cross reacting antigen) /FL = gb: BC005008.1 gb: M18216.1 gb: M29541.1 gb: NM_002483.1 |
| 203325_s_at | collagen, type V, alpha 1 |
| 203272_s_at | lung cancer candidate |

TABLE VII-continued

Increase gene number to 72 genes loses the specificity in the breast CTC signature

| | |
|---|---|
| 202376_at | gb: NM_001085.2 /DEF = *Homo sapiens* serine (or cysteine) proteinase inhibitor, clade A (alpha-1 antiproteinase, antitrypsin), member 3 (SERPINA3), mRNA. /FEA = mRNA /GEN = SERPINA3 /PROD = alpha-1-antichymotrypsin, precursor /DB_XREF = gi: 9665246 /UG = Hs.234726 serine (or cysteine) proteinase inhibitor, clade A (alpha-1 antiproteinase, antitrypsin), member 3 /FL = gb: BC003559.1 gb: K01500.1 gb: NM_001085.2 |
| 202005_at | gb: NM_021978.1 /def = *Homo sapiens* suppression of tumorigenicity 14 (colon carcinoma, matriptase, epithin) (ST14), mRNA. /FEA = mRNA /GEN = ST14 /PROD = suppression of tumorigenicity 14 (coloncarcinoma, matriptase, epithin) /DB_XREF = gi: 11415039 /UG = Hs.56937 suppression of tumorigenicity 14 (colon carcinoma, matriptase, epithin) /FL = gb: AF057145.1 gb: NM_021978.1 gb: AB030036.1 gb: AF133086.1 gb: AF118224.2 |
| 201130_s_at | gb: L08599.1 /DEF = Human uvomorulin (E-cadherin) (UVO) mRNA, complete cds. /FEA = mRNA /GEN = UVO /PROD = uvomorulin /DB_XREF = gi: 340184 /UG = Hs.194657 cadherin 1, type 1, E-cadherin (epithelial) /FL = gb: L08599.1 gb: NM_004360.1 |
| 200878_at | Consensus includes gb: AF052094.1 /DEF = *Homo sapiens* clone 23698 mRNA sequence. /FEA = mRNA /DB_XREF = gi: 3360400 /UG = Hs.8136 endothelial PAS domain protein 1 /FL = gb: U51626.1 gb: U81984.1 gb: NM_001430.1 |

Our results showed both the efficiency of the CAM cell enrichment platform to investigate GEP of tumor cells in blood samples and the potential value of the CTC gene expression signatures in understanding of mechanism of metastasis, discovery of cancer cell signatures in blood, and applications in cancer diagnosis and therapy. The results demonstrated that a CTC score greater than 40% discriminates a cancer from a normal sample regardless of the type of epithelial cancers.

The CTC signatures for colon cancer reported here were useful in discriminating cancer from normal samples only using a pair of upregulated (MUC8) and down-regulated (CEACAM1, IL6ST or COL4A3BP) genes selected from colon CTC signatures. Similarly, the CTC signatures for breast cancer were useful in discriminating cancer from normal samples only using a pair of upregulated (CDH1 or ST14) and down-regulated (SDCCAG1 or EPAS1) genes selected from breast CTC signatures.

Also, there are genes overlapping in CTC signatures for colon and breast cancers (FIG. 2-8; Tables I-VII), suggesting that colon and breast CTC share common genes that regulate epithelial tumor development and metastasis.

Current antibody-based, automated imaging methods identify and enumerate rare circulating cells with epithelial lineage markers (Epi$^+$) as tumor cells, and show a detection sensitivity in only 20% to 57% of patients with stage IV epithelial cancers (Allard et al., 2004; Cristofanilli et al., 2004). Detection of such cells using flow cytometry that are available in clinical facilities has not been successful because of the low abundance of rare Epi+ cells in blood. Cancer cell associated genes reported here may significantly increase the detection sensitivity and specificity for CTC derived from different types of solid tumors.

Little is known about the gene expression signature of metastatic tumor cells that emerge in the peripheral blood of cancer patients. A recent report using anti-EpCAM antibody enriched cells from blood of patients with metastatic breast, colon and prostate cancer showed that genes such as AGR2, FABP1, S100A13, S100A14, S100A16, and others were upregulated in CTC, and that FABP1 and KRT20 genes showed expression patterns associated with colorectal cancer, whereas SCGB2A1, SCGB2A2, and PIP genes were associated with breast cancer (Smirnov et al., 2005). However, these genes and their expression patterns differ from the colon and breast CTC gene expression signatures in this paper (Tables I-VII).

Previous tumor cell enrichment methods including anti-EpCAM antibody-magnetic cell separation described above have not been able to determine the specificity and sensitivity of a CTC gene expression signature. However, this report using the Vita-Cap™ CAM-based method, the experimental microarray model, the signatures for circulating colon tumor cells and circulating breast tumor cells demonstrated that the CAM cell enrichment approach for the determination of CTC gene expression signatures is highly effective and can be easily adopted for other cancer types.

In summary, the establishment of a metastatic cancer cell signature increases our understanding of the mechanism of tumor metastasis. In addition, a gene signature for circulating tumor cells of different types of solid cancers can be developed into cancer diagnostic blood tests that may detect the original site of an internal cancer using patients' blood samples. The blood test can serve as a potential tool for improved cancer diagnosis, monitoring and management of various types of internal malignant tumors.

Example 2

Gene Expression Signature of Metastatic Tumor Cells in Patients with Ovarian Cancer Here, we describe the enrichment of metastatic tumor cells in ascites (MTCA), which contained greater than 25% of cells positive for cytokeratin and CA125, from ovarian cancer patients using a novel collagen adhesion matrix (CAM) method that isolated cells invading collagen. Using the RNA extracted from MTCA fractions and comparing it with the RNA extracted from primary tumor cells in the ovary (PTC), we identified a MTCA signature, in which 21 upregulated genes were common between primary and metastatic tumor cells and 16 genes were upregulated only in metastatic tumor cells. We then selected five genes from the former and four genes from the latter to test in a similar set of samples using real-time RT-PCR. The MICA signature was used to distinguish samples of metastatic tumor cells in ascites from late stage primary tumor cells, and cells from benign and early stage ovarian tumors. Finding novel ways to detect metastatic cells by such an ovarian cancer gene signature could greatly aid in the understanding of metastasis and the management of cancer patients.

The objective of this project was to identify a set of genes that could be used for the detection and characterization of metastatic tumor cells in ovarian cancer patients. We generated global gene expression profiles (GEP) for tumor cells enriched by CAM functional enrichment from ascites (MTCA) and primary tumor cells (PTC) of ovarian cancer patients. Using the RNA extracted from MICA and comparing it with the RNA extracted from PTC and leukocyte fractions, we identified a MICA signature that contained 21 upregulated genes common between primary and metastatic tumor cells and 16 upregulated genes specific for MTCA. We then compared the gene expression patterns of the 37 genes in microarray data set and the nine genes selected from the signature in real-time RTPCR data set for their ability to distinguish and characterize tumor specimens from patients with benign and all stages of malignant ovarian tumors.

Clinical specimens. The human subject protection protocol for collection of tumor tissues and peritoneal effusion (ascites) from patients with ovarian cancer was reviewed and approved by the Institutional Review Board at Stony Brook University, N.Y. Specimens and relevant pathological data were obtained by the Department of Obstetrics, Gynecology and Reproductive Medicine, Stony Brook University, N.Y. Detailed information about all samples used in this study is presented in Table 8.

TABLE 8

Cell samples isolated from patients with ovarian and uterine tumors used in DNA microarray (GEP) and real-time RT-PCR (PCR) analyses*.

| GEP Sample | PCR Sample | Tumor type | Tumor grade | Tumor stage |
|---|---|---|---|---|
| MTCA1 | | Ascites, ovarian serous adenocarcinoma | 3 | IIIC |
| MTCA2 | | Ascites, ovarian serous adenocarcinoma | 3 | IIIC |
| MTCA3 | | Ascites, ovarian serous adenocarcinoma | 3 | IIIC |
| MTCA4 | | Ascites, ovarian serous adenocarcinoma | 3 | IIIC |
| MTCA5 | | Ascites, ovarian serous adenocarcinoma | 3 | IIIC |
| MTCA6 | | Ascites, ovarian serous adenocarcinoma | 3 | IIIC |
| MTCA7 | | Ascites, ovarian serous adenocarcinoma | 3 | IIIC |
| MTCA8 | | Ascites, ovarian serous adenocarcinoma | 3 | IIIC |
| MTCA9 | | Ascites, ovarian serous adenocarcinoma | 3 | IIIC |
| MTCA10 | | Ascites, ovarian serous adenocarcinoma | N/A | IIIC |
| MTCA11 | | Ascites, ovarian serous adenocarcinoma | 3 | IIIC |
| MTCA12 | | Ascites, ovarian serous adenocarcinoma | 3 | IIIC |
| MTCA13 | | Ascites, ovarian serous adenocarcinoma | 3 | IIIC |
| MTCA14 | | Ascites, ovarian serous adenocarcinoma | 3 | IIIC |
| MTCA15 | | Ascites, ovarian serous adenocarcinoma | N/A | IIIC |
| MTCA16 | | Ascites, ovarian clear cell adenocarcinoma | 3 | IIIC |
| MTCA17 | | Ascites, ovarian clear cell adenocarcinoma | 3 | IIIC |
| MTCA18 | | Ascites, ovarian clear cell adenocarcinoma | 3 | IIIC |
| MTCA19 | | Ascites, ovarian clear cell adenocarcinoma | 3 | IIIC |
| MTCA20 | | Ascites, ovarian clear cell adenocarcinoma | 3 | IIIC |
| MTCA21 | | Ascites, ovarian serous adenocarcinoma | 3 | IC |
| MTCA22 | | Ascites, ovarian serous adenocarcinoma | 3 | IC |
| PTC1 | PTC1 | Tumor, ovarian serous adenocarcinoma | 3 | IIIC |
| PTC2 | PTC2 | Tumor, ovarian serous adenocarcinoma | 3 | IIIC |
| PTC3 | PTC3 | Tumor, ovarian serous adenocarcinoma | 3 | IIIC |
| PTC4 | | Tumor, ovarian serous adenocarcinoma | 3 | IV |
| PTC5 | PTC5 | Tumor, ovarian serous adenocarcinoma | 3 | IV |
| e-PTC6 | | Tumor, ovarian serous adenocarcinoma | 3 | IC |
| f-PTC7 | f-PTC7 | Tumor, ovarian fibroma | Benign | Benign |
| m-PTC8 | | Tumor, ovarian mixed clear cell, papillary and endometrioid adenocarcinoma | 3 | IIIC |
| g-PTC9 | | Tumor, granulose | Adult-type | IIC |
| g-PTC10 | g-PTC10 | Tumor, granulose | Adult-type | IIC |
| g-PTC11 | g-PTC11 | Tumor, granulose | Adult-type | IIC |
| g-PTC12 | g-PTC12 | Tumor, granulose | Adult-type | IIC |
| PTC13 | | Tumor, ovarian serous adenocarcinoma | 3 | IIIC |
| PTC14 | | Tumor, ovarian serous adenocarcinoma | 3 | IIIC |
| PTC15 | | Tumor, ovarian serous adenocarcinoma | 3 | IIIC |
| PTC16 | | Tumor, ovarian serous adenocarcinoma | 3 | IIIC |
| PTC17 | | Tumor, ovarian serous adenocarcinoma | 3 | IIIC |
| PTC18 | | Tumor, ovarian serous adenocarcinoma | 3 | IIIC |
| LE1 | | Ascites, ovarian serous adenocarcinoma | 3 | IV |
| LE2 | | Ascites, ovarian serous adenocarcinoma | 3 | IIIC |
| LE3 | | Ascites, ovarian serous adenocarcinoma | 3 | IV |
| LE4 | | Ascites, ovarian serous adenocarcinoma | 3 | IIIC |

After obtaining patients' informed consent, ascites and solid tumors were harvested from patients undergoing abdominal surgery or paracentesis. An average of 2 liters of ascites, ranging from 0.5 to 16 liters, was collected in the presence of Anticoagulant Citrate Dextrose solution (ACD, Baxter, Deerfield, Ill.) containing 0.2 U/mL heparin. Solid tumors were made into cellular suspensions using collagenase digestion of the extracellular matrix (ECM) and mechanical dissociation for cell separation.

Tumor cell enrichment. Tumor cell separation was performed within 1 hour of specimen collection. Ascites were cleared of blood clots and tissue aggregates using a 200 μm mesh filter; primary tumors were dissociated into cell suspension using 1 mg/mL Collagenase-Dispase (Roche, Indianapolis, Ind.) before cell fractionation. Aliquots of cell samples, at density of 5×106 to 5×107 cells/mL, were seeded onto a plate or slide coated with CAM containing type collagen films (Vita-Assay", Vitatex Inc., Stony Brook, N.Y.). After culture for 18 hours, the non-adherent cells were washed away, and the remaining adherent cells (the tumor cells) were stained for immunocytochemistry or processed for RNA extraction. Additionally, a one-step method (Vita-Cap", Vitatex Inc., Stony Brook, N.Y.) was used to isolate cells from ascites, in a few cases. Using immunocytochemistry, there were no noticeable differences in the proportion of cytokeratin and CA125 positive cells in populations enriched by both assays.

The CAM-enriched cells included tumor cells that were positive for cytokeratin and CA125 by immunocytochemical staining using anti-pan cytokeratin (PCK; clone C-11, Sigma, Miss., USA) and anti-CA125 (Clone M11, Dako, Carpinteria, Calif.) antibodies. Leukocytes were separated from ascites using Dynal anti-CD45 Leukocyte Enrich system (Invitrogen, Carlsbad, Calif.). GEP and bioinformatic analysis. Bioinformatics comparison was performed between GEP of the MTCA, PTC and leukocytes from patients with malignant and benign ovarian tumors. This comparison resulted in about 126 genes that were differentially expressed in MTCA and PTC cells (fold change >2; P<0.05, with Multi Testing Correction on to reduce FDR rate, GeneSpring 7.2). Quantitative real-time RT-PCR. RNAs were reverse transcribed by st Strand cDNA Synthesis Kit for RT-PCR (AMV, Roche, Indianapolis, Ind.) with random primers supplied by the kit. Primers for targeted genes were designed using web based primer3 software (from http://www-qenome.wi.mit.edu/c.qi-bin/primedprimer3 www.c,qi). The primers used for real-time PCR are listed in FIG. 9 and Table 9. All primers were specific for their respective genes as confirmed by BLAST. Light Cycler-FastStart DNA Master SYBR Green kit (Roche, Indianapolis, Ind.) was used to prepare PCR reactions according to manufacturer's specifications. Assays were carried out in LightCycler capillaries in a 20 IJI reaction volume. 2 pl of diluted cDNA template was used for each PCR. PCR conditions were: 95° C. for 15 s, 55° C.-60° C. for 5 s, 72° C. for 12 s. LightCycler software package (Version 5.2, Roche) was used to construct the standard curve. Each sample was analyzed in duplicate in each experiment. Expression levels of all genes were normalized to β-actin.

TABLE 9

| Description | Forward Primer | Reverse Primer |
|---|---|---|
| β-actin | AGATGACCCAGATCATGTTTGA SEQ ID NO. 1 | GCACAGCTTCTCCTTAATGTCA SEQ ID NO. 2 |
| MUC1 | CTATGTGCCCCCTAGCAGTACC SEQ ID NO. 3 | TTCCACACACTGAGAAGTGTCC SEQ ID NO. 4 |
| LCN2 | ATGTATGCCACCATCTATGAGC SEQ ID NO. 5 | CTCCTTTAGTTCCGAAGTCAGC SEQ ID NO. 6 |
| GA733-1 | TTCAACCACTCAGACCTGGAC SEQ ID NO. 7 | GAGAACTTCGGGGGAATCTC SEQ ID NO. 8 |
| KRT18 | GCCTACAAGCCCAGATTGC SEQ ID NO. 9 | GGCCTTCAGATTTTTCATGG SEQ ID NO. 10 |
| MMP7 | TTCCAAATAGCCCAAAATGG SEQ ID NO. 11 | CCCATCAAATGGGTAGGAGT SEQ ID NO. 12 |
| COL1A2 | CTGGGTCTACCAGGTGTTGC SEQ ID NO. 13 | CCAGAAGGACCAGTTTCACC SEQ ID NO. 14 |
| SDF1 | GAGCTACAGATGCCCATGC SEQ ID NO. 15 | CTTTAGCTTCGGGTCAATGC SEQ ID NO. 16 |
| Autotaxin | GCATGCAGACTGTTTTTGTAGG SEQ ID NO. 17 | GTTCATCCAACTTGTTCTTTGG SEQ ID NO. 18 |
| CXCR4 | AGCATGACGGACAAGTACAGG SEQ ID NO. 19 | GATGAAGTCGGGAATAGTCAGC SEQ ID NO. 20 |
| CD45 | TGCCTCAATCTGGATAAAAACC SEQ ID NO. 21 | CTTCAACTTCCAAATGGTAACG SEQ ID NO. 22 |

Total RNAs of CAM isolated tumor cells were purified by RNeasy® Mini Kit (Qiagen, Valencia, Calif.) and then subjected to DNA microarraying. Generation of cRNA, labeling, hybridization, and scanning of the Affymetrix oligonucleotide microarray chip (Hu95av2, 12,600 probe sets) was according to the manufacturer's specifications (Affymetrix, Santa Clara, Calif.). Analysis of each chip was performed using the Affymetrix Microarray Suite 5.1 Software to generate raw expression data. GeneSpring 7.2 software (Silicon Genetics, Redwood City, Calif.) was used to perform statistical analysis and investigate the variation in gene expression.

GEP for primary and metastatic tumor cells from patients with ovarian cancers. MTCA and PTC were separated from other cells by the CAM function-affinity enrichment of ascites and ovarian tumors from ovarian cancer patients. Cell purity was evaluated by immunocytochemistry and cell fractions that exhibited over 25% pan-cytokeratin and CA125 positivity were used for GEP. To generate global GEP of tumor cells, RNA was extracted from the MTCA fractions and was compared with the RNA from the PTC and leukocytes by using the Affymetrix GeneChip platform. We then selected 37 genes (FIG. 9A) based on two criteria: (1) genes known to upregulate in cells of the epithelial lineage and metastatic tumors, and (2) further hierarchical gene clustering that showed genes upregulated in MTCA and PTC, and genes upregulated in MICA but downregulated in PTC. The list of resulting genes constitutes the MTCA gene expression signature.

Figure 9:
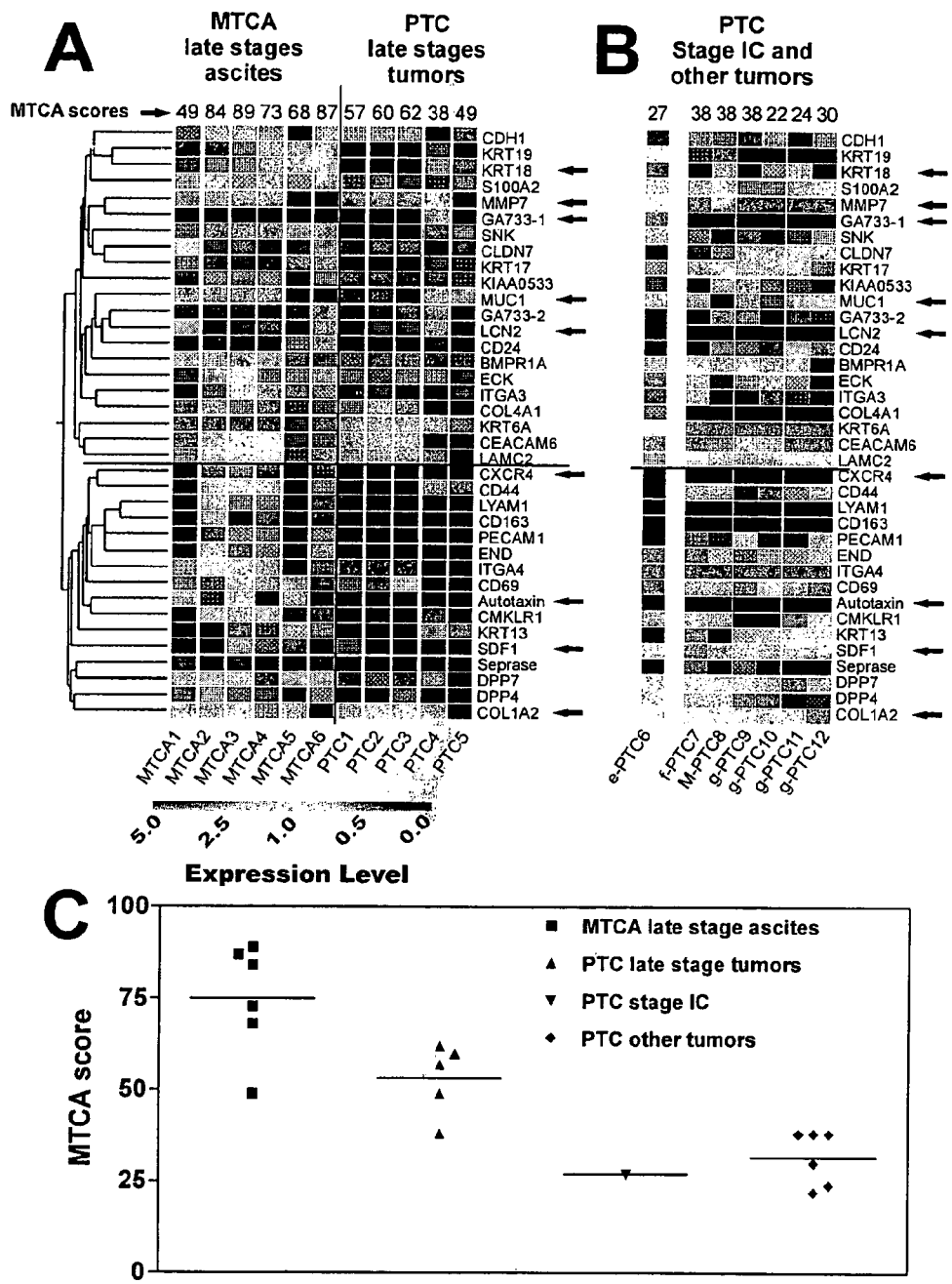
FIG. 9 shows expression profile of genes associated with metastatic ovarian tumor cells in ascites (MTCA) compared to primary tumor cells of other types. 37 genes were selected based on two criteria: (1) genes known to upregulate in cells of the epithelial lineage and metastatic tumors, and (2) further hierarchical gene clustering that showed genes upregulated in MTCA and PTC, and genes upregulated in MICA but downregulated in PTC.

The MTCA signature contained a total of 21 upregulated genes in MTCA and PTC, suggesting that both have common lineages (FIG. 9, top 21 rows of panel A), and 16 genes that were upregulated in MTCA but downregulated in PTC, suggesting that these genes were active in metastasis (FIG. 9, bottom 16 rows of panel B). Individual genes of the former expressed differently in all samples examined. Thus, we defined the MTCA score of a sample as the percentage of genes that matched the upregulated expression of 37 genes in the MICA signature. The MTCA scores for MTCA were 49-89, whereas they were 38-62 for PTC (FIG. 9A). Examination of the 37-gene expression pattern in the cells isolated by CAM from PTC of a stage IC serous adenocarcinoma of the ovary and other types of non-epithelial ovarian tumors showed MTCA scores ranging between 22-38. These findings indicated the efficiency of the CAM cell enrichment approach used to acquire tumor cell-specific GEP.

Verification of MTCA-specific expression of the candidate genes by quantitative real time RT-PCR. To verify the MTCA signature using an alternative method, expression of the candidate genes selected from the signature were measured in 54 cell samples derived from patients with benign and malignant ovarian tumors and control leukocytes using quantitative real-time RT-PCR. Among the 37 genes in the signature, five ovarian tumor genes (MUC1, LCN2, GA733-1, KRT18, and MMP7) and four metastatic genes (SDF1, autotaxin, CXCR4 and COLIA2) reported in the literature were selected. In addition, the common leukocyte gene CD45 was used to control for the presence of leukocytes in samples. Quantitative real-time RT-PCR was used to measure the expression of the five ovarian tumor genes and the four metastatic genes. For each gene, relative expression was compared with the mean fold expression (normalized to β-actin) of numbers of cell samples in each cell group. CAM$^\pm$ cell fractions from ascites of patients with late stage serous adenocarcinoma of the ovary are labelled MTCA7 MTCA20 and those from stage IC serous adenocarcinoma of the ovary are labelled MTCA21 and MTCA22. CAM$^\pm$ cell fractions from primary tumors of patients with late stage serous adenocarcinoma of the ovary are labelled PTC1-PTC18; those from ovarian granulosa tumors are labelled gPTC10-gPTC12; that from benign fibroma is labelled f-PTC7. Normal cells (leukocytes) from ascites of patients with late stage serous adenocarcinoma of the ovary are labelled LE1 LE16. MTCA score of each sample is indicated as the percentage of genes that matched the upregulated expression of the nine genes selected from the ovarian MTCA signature. The MTCA score of each sample was determined as the percentage of genes that matched the upregulated expression of the nine genes selected from the MTCA signature, indicative of the extent of metastatic tumor cells in a sample. Correlation between the MTCA score and tumor cells in the clinical specimens is shown in FIG. 10B. The bars represent mean values for each patient subgroup.

Figure 10:
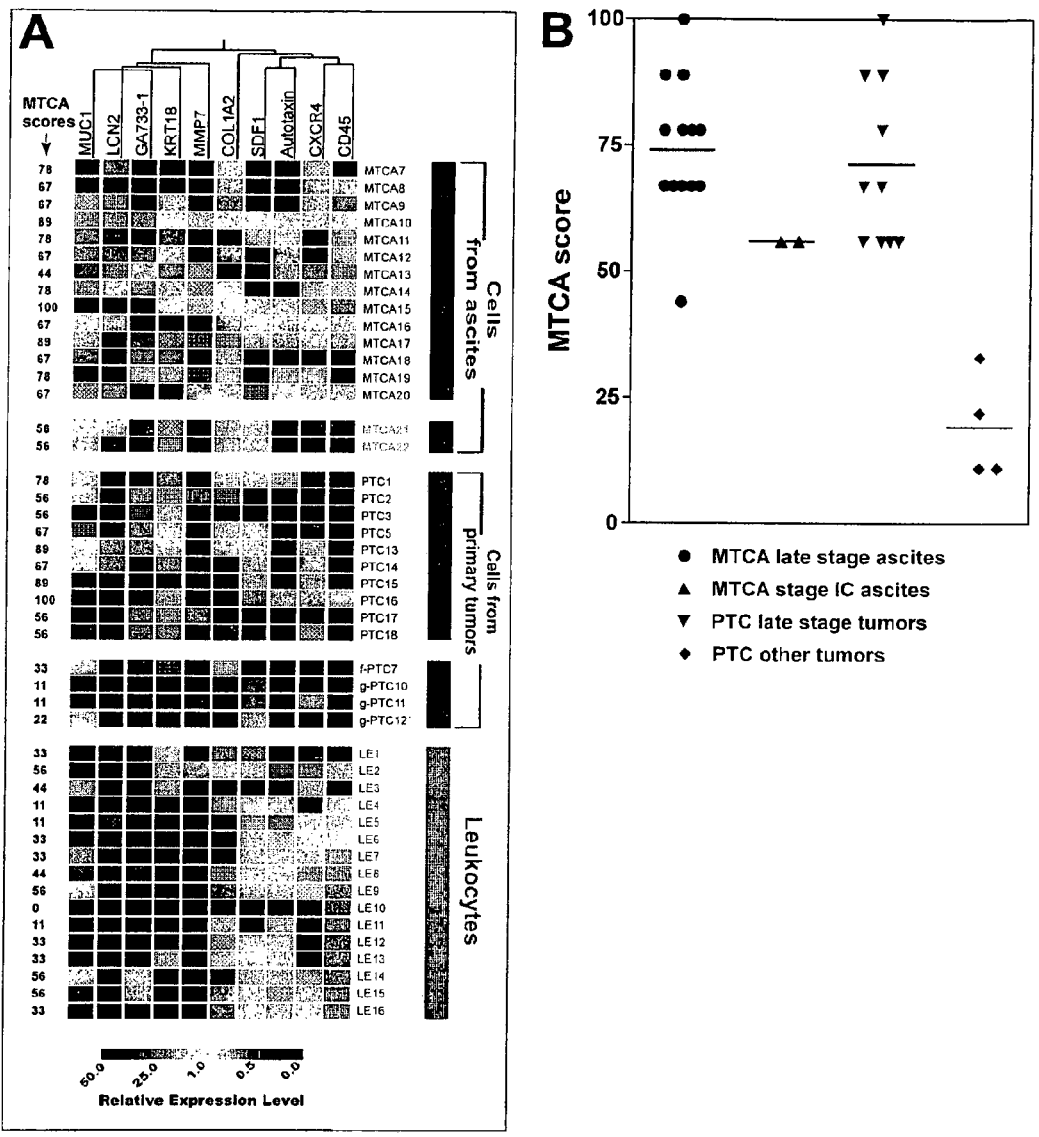
FIG. 10 shows data for the real-time RT-PCR validation of the nine genes selected from the MTCA gene expression signature in FIG. 9. Expression of the candidate genes selected from the MCTA signature were measured in 54 cell samples derived from patients with benign and malignant ovarian tumors and control leukocytes using quantitative real-time RT-PCR.

The MTCA scores for MTCA from patients with late stage serous ovarian adenocarcinoma (FIG. 10, sample MTCA7-20) were 44-100 and 56 in ascites of stage IC serous adenocarcinoma (FIG. 10, sample MTCA21-22); MTCA scores for PTC in late stage ovarian serous adenocarcinoma tumors (FIG. 10, sample PTC1-18) were 56-100 and 11-33 in other tumors (FIG. 10, samples f-PTC7, and g-PTC10-12). Although most cell fractions enriched by CAM from ascites contained leukocytes, some samples exhibited MTCA scores of 67-78 and their CD45 gene was downregulated (FIG. 10, sample MTCA11, MTCA18 and MTCA19), suggesting the absence of leukocytes in these samples and that the selected nine genes were specific for tumor cells. These findings confirm both the efficiency of the CAM cell enrichment approach to investigate GEP of tumor cells in clinical specimens and the potential value of the MICA gene expression signature in ovarian cancer diagnosis.

Discrimination between metastatic and benign or local tumors using the MTCA signature. Using GEP of CAM-enriched samples, we evaluated the ability of the MTCA gene expression signature to discriminate between metastatic tumors in ascites and different primary tumor types. Samples from the ascites of metastatic cancer patients yielded a much higher average of 75+15 MICA scores than that of the five primary tumors of similar patients, 53+10 ($P<0.05$, Student's t-test), and PTC of a stage IC serous adenocarcinoma, which was 27. Other tumor types received a score of 32+7 ($P<0.0001$). When nine of 37 genes in the MICA signature were verified in clinical specimens using real-time RT-PCR (FIG. 10B), samples from ascites of metastatic cancer patients yielded similar averages of MTCA scores as the primary tumors of metastatic cancer patients (74+14 and 71+17 respectively) but higher than that of a stage IC serous adenocarcinoma, 56, and other tumor types, 19+11 ($P<0.0001$). These data strongly suggest that cells enriched by CAM from clinical specimens are useful in gene expression profiling of cancer and that the MTCA gene expression signature is specific for the detection of metastatic tumor cells.

Little is known about the gene expression signature of metastatic tumor cells that emerge in the peritoneal cavity or secondary organs of ovarian cancer patients. To identify a novel set of genes that can be used for the detection and characterization of metastatic cells in patients with serous adenocarcinoma, we used a novel functional CAM cell enrichment method to obtain reproducible tumor cell preparations that express cytokeratin and CA125, and generated the first metastatic cell signature from clinical specimens. We identified a MTCA signature, in which 21 upregulated genes were common between primary and metastatic tumor cells and 16 genes were upregulated only in metastatic tumor cells (FIG. 9). Assigning a MTCA score to a sample, we showed that the MTCA signature distinguished the tumors in ascites from primary tumors of late stages, from tumors of early stages, and from benign ovarian tumors (FIG. 9C, 10B). We then tested its reproducibility using nine genes selected from the signature by real-time RT-PCR (FIG. 10) and were able to verify the use of the MTCA gene signature in distinguishing MICA of late versus early stage serous adenocarcinoma, and samples from serous adenocarcinoma versus non-epithelial ovarian tumors. We verified nine novel metastatic cell-associated genes for their ability to detect and characterize tumor specimens from patients with benign and all stages of malignant ovarian tumors (FIG. 10). The role of these genes in ovarian cancer progression is not known. The five genes (MUC1, LCN2, GA733-1, KRT18, and MMP7) of the MICA signature were previously shown to associate with serous adenocarcinoma of the ovary (10, 11). Furthermore, we identified 16 metastasis-associated genes in the MICA signature, and validated four, including SDF1, autotaxin, CXCR4 and COLIA2, using real-time RT-PCR. Previous studies have shown the association of these genes in metastasis, i.e., autotoxin as an autocrine motility-stimulating factor (12), SDF1 as a chemokine and CXCR4 as a chemokine receptor implicated in organ homing of stem and cancer cells (13, 14), and COLIA2 as a type collagen found in metastatic tumors (15). However, the power of detecting metastatic tumor cells depends heavily on the 37-gene signature as a whole, and would be increased by the addition of the CA125/MUC16 gene. The CA125 gene is absent in the early version of Affymetrix Hu95av2 genechip used for this study and is detected in ovarian tumors using the Affymetrix Hu133A 2.0 high-density oligonucleotide microarray chip (data not shown) and by serial analysis of gene expression (16). We found that using only the selected nine genes from the signature reduced the detection specificity by a noticeable degree; the nine genes as a whole could not discriminate metastatic tumors in ascites from primary tissues in late stage samples, and that no single individual gene is sufficient to distinguish MTCA from other tumor cell fractions (FIGS. 9 and 10)

Example 3

To validate the 17-candidate colorectal cancer CTC marker genes (DTR, PSCA, MUC3A, THRA, CD79B, NOTCH1, MUCDHL, NEUROG2, MDS028, KRT18, FOLH1, CD44, FCER2, SCF, CD7, SOX1 and TEKT3), the CTC score of a sample was used in the testing set of cellular samples that consists of 9 normal, 9 colorectal cancer and 20 breast cancer (FIG. 16B-C). The CTC score of a sample was determined as the percentage of the 17-candidate colorectal cancer CTC marker genes that exhibited upregulated expression. CTC scores for the 9 normal samples were 0-12%, whereas the CTC scores of the 9 colorectal cancer samples were 94-100% and the 20 breast cancer samples were 24-100%. There was a significant difference of the mean±standard error CTC score between normal and cancer patients with colorectal and breast tumor types (FIG. 16C): 2.67±1.45 in normal samples as compared with 98.67±0.88 in colorectal cancer samples and 69.20±5.53 in breast cancer samples (p-value<0.0001). CTC scores varied significantly between colorectal and breast cancer samples (p=0.0015). In addition, CTC cores were different significantly between patients with stage III-IV colorectal tumors and these with stage III-IV breast tumors (FIG. 16C, p=0.0017). This finding suggests that the 17-candidate colorectal cancer CTC marker genes are sufficient for detection of CTCs and their original tumors at the highest specificity and sensitivity using a nucleic acid, CAM-based blood test.

Example 4

FIG. 17 provides an example of CTC detection using the proposed cell-based CTC detection method and reagents. Approximately 3 mL of blood were seeded on a red fluorescent CAM-coated device. Circulating cells were incubated for 12-18 hours to mark the captured cells in situ. This step labeled tumor cells by assaying their ability to ingest fluorescent CAM fragments (CAM$^+$). Cells were then fixed with 3% paraformaldehyde/PBS, permeablized with 0.1% Triton X-100, and then immuno-stained using antibodies against two of the CTC markers, i.e., red color precipitates associated with antibody against KRT16 and green fluorescent antibody against VWF. Cells with the CTC immuno-phenotype were defined as staining positively with red color precipitates associated with antibody against KRT16 and green fluorescent antibody against VWF, along with negatively stained with red color precipitates associated with antibody against CD45, to discriminate the tumor progenitor cells from co-purifying leukocytes and normal circulating progenitor cells (FIG. 17). The KRT16$^+$/Hs$^+$/VWF$^+$ CTCs were then validated for tumor cell invasiveness by the uptake of fluorescent CAM (FIG. 17, labeled CAM, double arrows) to discriminate them from other non-tumor CAM-avid circulating cells. CTCs were detected as KRT16$^+$/Hs$^+$/VWF$^+$/CAM$^+$ cells (FIG. 17 upper panel, double arrows) and CD45$^-$/Hs$^+$/VWF$^+$/CAM$^+$ cells (FIG. 17 lower panel, double arrows). Thus, the isolated CTCs can be detected on a single cell level using at least two CTC markers simultaneously in microscopic imaging or preceded via FACS or other molecular detection methods on the cell population level.

Example 5

The demonstration that circulating endothelial cells can provide sustained endothelial recovery is inferential evidence for circulating endothelial progenitor cells (Asahara et al., 1997). To investigate the hypothesis that peripheral blood of cancer patients contains cells that can differentiate into cells of different developmental (epithelial and endothelial) lineages, CAM-isolated cells from both normal and cancer blood samples that were further sorted by means of magnetic beads coated with antibody to CD31 (Dynal-InVitrogen) and cultured in vitro and their proliferation and differentiation were examined (FIGS. 21 and 22). CD31-positive cells were isolated by means of magnetic beads coated with antibody to CD31 (Dynal, Lake Success) from the cellular fraction that was first enriched from blood of cancer patients using a CAM-coated tube (Vita-Cap™, Vitatex Inc., Stony Brook, N.Y.).

Immuno-phenotyping of the cells isolated by the two enrichment steps show a population of CD31+/VWF+ or CDH5$^{low}$/VWF+ cells being CECs, and another population of CD31+/VWF$^+$, CDH5+/VWF$^+$, KRT8+/VWF+ or CD45−/VWF+large (>12 μm in diameter) cells being CTCs (FIG. 21). The preferred method of detecting CTCs is to identify CDH5+/VWF+ or KRT8+/VWF+large cells (FIG. 22).

To evaluate whether circulating CD31+ cells progressed to an endothelial- or tumor-like phenotype, circulating cells isolated by magnetic beads coated with antibody to CD31 and CAM were assayed for the proliferation and differentiation of endothelial and tumor phenotype in vitro. When plated on tissue culture plastic coated with collagen type I gel, at a density of 1×10$^3$ cells/mm$^2$, and cultured for three days, cells showed enhanced endothelial proliferation and differentiation, including the formation of cellular clusters and tube-like networks (FIG. 22A-B, double arrows) with canal-like structures in the center (FIG. 12A-B, single arrow), suggesting that circulating CD31+ cells contain both endothelial and tumor progenitor cell populations that exhibit endothelial cell function. After 7 days in culture, individual colonies of spindle-shaped endothelial cells (FIG. 22C, open arrow) and epithelioid cells (FIG. 22D, double arrows) were formed. Colonies of highly enriched epithelioid cells that were grown from the CD31-isolated cells were CK+/VWF− (FIG. 22E-F, single and double arrows), suggesting that these epithelioid cells are differentiated and lose expression of the endothelial marker (VWF). On the other hand, colonies of spindle-shaped cells that were grown from the CD31-isolated cells were CD31+ (FIG. 22F, open arrows), suggesting that these spindle cells are differentiated endothelial cells and retain expression of the endothelial lineage marker CD31.

Example 6

Figure 15:
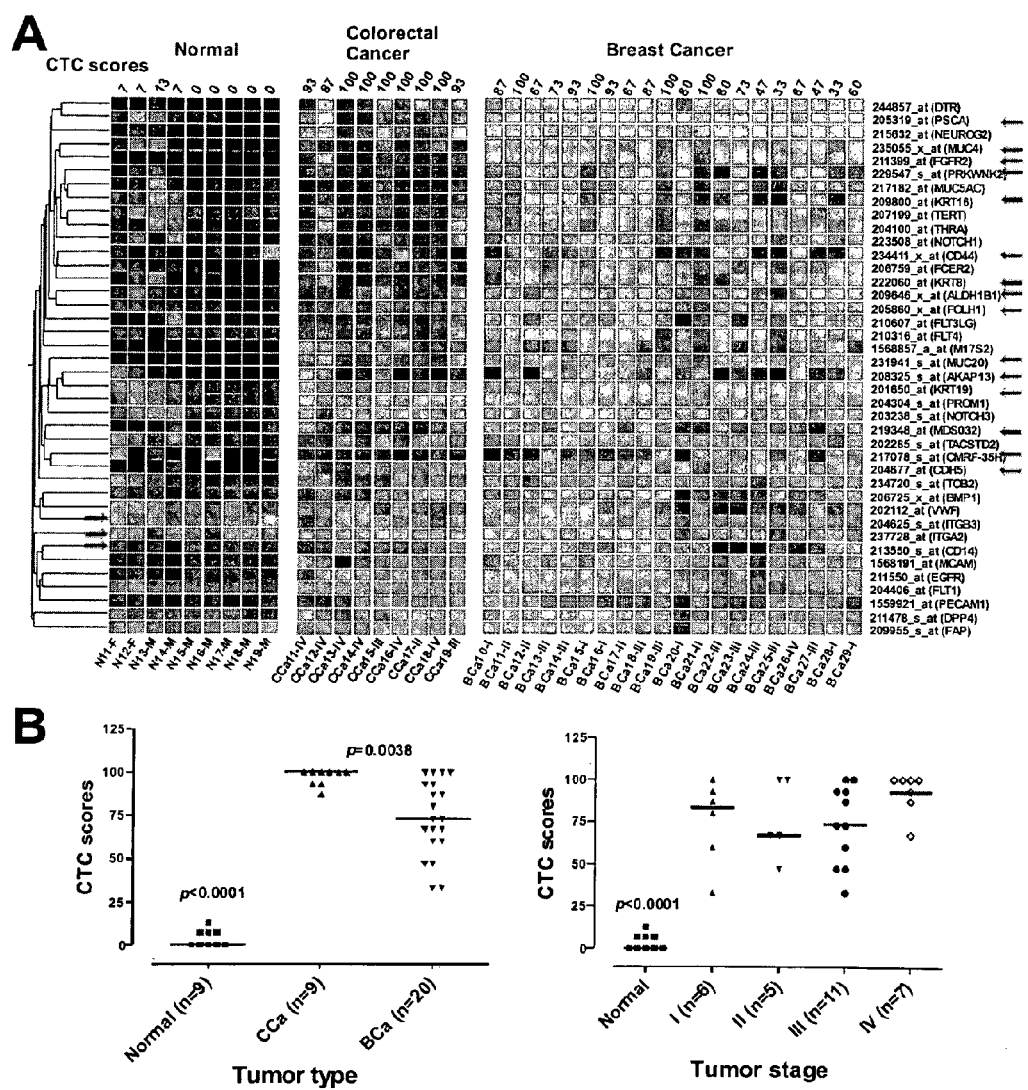
FIG. 15 shows the 15 tumor progenitor cell genes and three internal control genes that are preferable CTC markers. To validate the 15-TP marker genes (PSCA, MUC4, FGFR2, PRKWNK2, KRT16, CD44, KRT8, ALDH1B1, FOLH1, MUC20, AKAP13, KRT19, MDS032, CMRF-35H and CDH5), the CTC score of a sample was used in the testing set of cellular samples that consists of 9 normal, 9 colorectal cancer and 20 breast cancer (FIG. 5A-B). The CTC score of a sample was determined as the percentage of the 15-TP marker genes that exhibited upregulated expression. A significant difference of the mean±standard error CTC score was observed between normal and cancer patients with colorectal and breast tumor types.

To validate the 15-TP marker genes (PSCA, MUC4, FGFR2, PRKWNK2, KRT16, CD44, KRT8, ALDH1B1, FOLH1, MUC20, AKAP13, KRT19, MDS032, CMRF-35H and CDH5), the CTC score of a sample was used in the testing set of cellular samples that consists of 9 normal, 9 colorectal cancer and 20 breast cancer (FIG. 5A-B). The CTC score of a sample was determined as the percentage of the 15-TP marker genes that exhibited upregulated expression. CTC scores for the 9 healthy control samples were 0-13%, whereas the CTC scores of the 9 colorectal cancer samples were 87-100% and the 20 breast cancer samples were 33-100%. There was a significant difference of the mean±standard error CTC score between normal and cancer patients with colorectal and breast tumor types (FIG. 15B): 3.78±1.61 in normal samples as compared with 97.00±1.61 in colorectal cancer samples and 73.45±4.91 in breast cancer samples (p-value<0.0001). Although CTC scores varied significantly between colorectal and breast cancer samples (p=0.0038), the difference could be due to the fact that 6 out of 9 colorectal cancer patients were stage IV and none at stage I, whereas only 1 out of 20 breast cancer patients were stage IV and 6 at stage I. However, CTC cores were not different significantly by tumor stage (FIG. 15B, p-value>0.05). Using a CTC score of 40% as a cut-off, the 15-TP marker genes predicted the presence of tumor cells in 9 out of 9 blood samples of cancer patients with stage II-IV colorectal tumors (FIG. 15A-B, 100% CTC detection sensitivity) and 18 out of 20 breast cancer patients with stages I-IV tumors (FIG. 15A-B, 90% CTC detection sensitivity). This finding suggests that the 15-TP marker genes and the 3 internal control genes are sufficient for detection of CTCs at the highest specificity and sensitivity using a nucleic acid, CAM-based blood test.

References

1. Ozols R F, Bookman M A, Connolly D C, Daly M B, Godwin A K, Schilder R J, Xu X, Hamilton T C. Focus on epithelial ovarian cancer, Cancer Cell, 2004; 5:19-24.
2. Bast R C, Jr. Status of Tumor Markers in Ovarian Cancer Screening, J. Clin. Oncol., 2003; 21:200s.
3. Kohn E C, Fidler J, Fishman D, Jaffe R, Liotta L A, Van Trappen P, Mills G B, Trope C. Discussion: metastasis and angiogenesis in epithelial ovarian cancer, Gynecol. Oncol, 2003; 88:$37-$42.
4. Naora H, Montell D J. Ovarian cancer metastasis: integrating insights from disparate model organisms, Nat Rev Cancer, 2005; 5:355-66.
5. Braun S, Schindlbeck C, Hepp F, Janni W, Kentenich C, Riethmuller G, Pantel K. Occult tumor cells in bone marrow of patients with locoregionally restricted ovarian cancer predict early distant metastatic relapse, Journal of Clinical Oncology., 2001 19:368-75.
6. Sood A K, Coffin J E, Schneider G B, Fletcher M S, DeYoung B R, Gruman L M, Gershenson D M, Schaller M D, Hendrix M J. Biological significance of focal adhesion kinase in ovarian cancer: role in migration and invasion, Am. J. Pathol., 2004; 165:1087-95.
7. Wang X, Wang E, Kavanagh J J, Freedman R S. Ovarian cancer, the coagulation pathway, and inflammation, JoTransl. Med., 2005; 3:25.
8. Mareel M, Leroy A. Clinical, cellular, and molecular aspects of cancer invasion, Physiol Rev, 2003; 83:337-76.
9. Chen W-T. Proteolytic activity of specialized surface protrusions formed at rosette contact sites of transformed cells, J. Exp. Zool., 1989; 251:167-85.
10. Adib T R, Henderson S, Perrett C, Hewitt D, Bourmpoulia D, Ledermann J, Boshoff C. Predicting biomarkers for ovarian cancer using gene-expression microarrays, British Journal of Cancer., 2004; 90:686-92.
11 Schaner M E, Davidson B, Skrede M, Reich R, Florenes V A, Risberg B, Berner A, Goldberg I, Givant-Horwitz V, Trope C G, Kristensen G B, Nesland J M, Borresen-Dale A L. Variation in gene expression patterns in effusions and primary tumors from serous ovarian cancer patients, Mol Cancer, 2005; 4:26.
12. Stracke M L, Krutzsch H C, Unsworth E J, Arestad A, Cioce V, Schiffmann E, Liotta L A. Identification, purification, and partial sequence analysis of autotaxin, a novel motility stimulating protein, Journal of Biological Chemistry, 1992; 267:2524-9.
13. Liang Z, Wu T, Lou H, Yu X, Taichman R S, Lau S K, Nie S, Umbreit J, Shim H. Inhibition of breast cancer metastasis by selective synthetic polypeptide against CXCR4, Cancer Res, 2004; 64:4302-8.
14. Ottaiano A, Franco R, Aiello T A, Liguori G, Tatangelo F, Delrio P, Nasti G, Barletta E, Facchini G, Daniele B, Di B A, Napolitano M, lerano C, Calemma R, Leonardi E, Albino V, De A, V, Falanga M, Boccia V, Capuozzo M, Parisi V, Botti G, Castello G, Vincenzo I R, Scala S. Overexpression of both CXC chemokine receptor 4 and vascular endothelial growth factor proteins predicts early distant relapse in stage I1-111 colorectal cancer patients, Clin. Cancer Res, 2006; 12:2795-803.
15. Ramaswamy S, Ross K N, Lander E S, Golub T R. A molecular signature of metastasis in primary solid tumors, Nature Genetics, 2003; 33:49-54.
16. Hough C D, Sherman-Baust C A, Pizer E S, Montz F J, Im D D, Rosenshein N B, Cho K R, Riggins G J, Morin P J. Large-scale serial analysis of gene expression reveals genes differentially expressed in ovarian cancer, Cancer Research, 2000; 60:6281-7.

Allard, W. J., Matera, J., Miller, M. C., Repollet, M., Connelly, M. C., Rao, C., Tibbe, A. G., Uhr, J. W., and Terstappen, L. W. (2004). Tumor cells circulate in the peripheral blood of all major carcinomas but not in healthy subjects or patients with nonmalignant diseases. Clin. Cancer Res 10, 6897-6904.

Chambers, A. F., Groom, A. C., and MacDonald, I. C. (2002). Dissemination and growth of cancer cells in metastatic sites. Nature Reviews *Cancer.* 2, 563-572.

Chen, W.-T. (1989). Proteolytic activity of specialized surface protrusions formed at rosette contact sites of transformed cells. J. Exp. Zool. 251, 167-185.

Chen, W.-T., Chen, J. M., Parsons, S. J., and Parsons, J. T. (1985). Local degradation of fibronectin at sites of expression of the transforming gene product pp60src. Nature 316, 156-158.

Choesmel, V., Anract, P., Hoifodt, H., Thiery, J. P., and Blin, N. (2004). A relevant immunomagnetic assay to detect and characterize epithelial cell adhesion molecule-positive cells in bone marrow from patients with breast carcinoma: immunomagnetic purification of micrometastases. Cancer 101, 693-703.

Coopman, P. J., Thomas, D. M., Gehlsen, K. R., and Mueller, S. C. (1996). Integrin α3β1 participates in the phagocytosis of extracellular matrix molecules by human breast cancer cells. Mol. Biol. Cell 7, 1789-1804.

Cristofanilli, M., Budd, G. T., Ellis, M. J., Stopeck, A., Matera, J., Miller, M. C., Reuben, J. M., Doyle, G. V., Allard, W. J., Terstappen, L. W., and Hayes, D. F. (2004). Circulating tumor cells, disease progression, and survival in metastatic breast cancer. N. Engl. J. Med. 351, 781-791.

Mareel, M. and Leroy, A. (2003). Clinical, cellular, and molecular aspects of cancer invasion. Physiol Rev 83, 337-376.

Mueller, S. C. and Chen, W.-T. (1991). Cellular invasion into matrix beads: localization of beta 1 integrins and fibronectin to the invadopodia. J. Cell Sci. 99, 213-225.

Pantel, K. and Brakenhoff, R. H. (2004). Dissecting the metastatic cascade. Nat. Rev. Cancer 4, 448-456.

Pantel, K., Cote, R. J., and Fodstad, O. (1999). Detection and clinical importance of micrometastatic disease. J. Natl. Cancer Inst. 91, 1113-1124.

Sabile, A., Louha, M., Bonte, E., Poussin, K., Vona, G., Mejean, A., Chretien, Y., Bougas, L., Lacour, B., Capron, F., Roseto, A., Brechot, C., and Paterlini-Brechot, P. (1999). Efficiency of Ber-EP4 antibody for isolating circulating epithelial tumor cells before RT-PCR detection. Am. J. Clin. Pathol. 112, 171-178.

Smirnov, D. A., Zweitzig, D. R., Foulk, B. W., Miller, M. C., Doyle, G. V., Pienta, K. J., Meropol, N. J., Weiner, L. M., Cohen, S. J., Moreno, J. G., Connelly, M. C., Terstappen, L. W., and O'hara, S. M. (2005). Global gene expression profiling of circulating tumor cells. Cancer Res 65, 4993-4997.

Thurm, H., Ebel, S., Kentenich, C., Hemsen, A., Riethdorf, S., Coith, C., Wallwiener, D., Braun, S., Oberhoff, C., Janicke, F., and Pantel, K. (2003). Rare expression of epithelial cell adhesion molecule on residual micrometastatic breast cancer cells after adjuvant chemotherapy. Clinical Cancer Research 9, 2598-2604.

The invention claimed is:

1. A method of detecting a circulating tumor cell in a subject comprising:
   a) providing a sample of blood from said subject;
   b) enriching cellular adhesion matrix (CAM)-avid cells from said sample by selecting cells from said sample that adhere to a collagen-based cellular adhesion matrix, to provide CAM-enriched circulating cells; and
   c) detecting increased expression, in said CAM-enriched circulating cells, of each of the genes DPP4, CD44, FAP, KRT8, KRT16, and KRT19, relative to control levels;
   wherein increased expression of DPP4, CD44, FAP, KRT8, KRT16, and KRT19 in said CAM-enriched circulating cells, relative to control levels, indicates the presence of a circulating tumor cell in said subject.

2. The method of claim 1, wherein said circulating tumor cell is distinguished from other tumor cells of epithelial origin.

3. The method of claim 1, wherein said circulating tumor cell is a colorectal cancer cell.

4. The method of claim 1, wherein said circulating tumor cell is a breast cancer cell.

5. The method of claim 1, wherein said circulating tumor cell is an ovarian cancer cell.

6. The method of claim 1, wherein said control levels represent the level of expression of DPP4, CD44, FAP, KRT8, KRT16, and KRT19 in CAM-enriched circulating cells of a healthy subject.

7. The method of claim 1, wherein step (c) further comprises detecting an increase in the expression of each of the genes KRT17, KRT18, and KRT20 in said CAM-enriched circulating cells.

8. The method of claim 7, wherein said circulating tumor cell is a colorectal cancer cell.

* * * * *

SEQUENCE LISTING

```
<160> NUMBER OF SEQ ID NOS: 22

<210> SEQ ID NO 1
<211> LENGTH: 22
<212> TYPE: DNA
<213> ORGANISM: Homo sapiens

<400> SEQUENCE: 1
agatgaccca gatcatgttt ga                                              22

<210> SEQ ID NO 2
<211> LENGTH: 22
<212> TYPE: DNA
<213> ORGANISM: Homo sapiens

<400> SEQUENCE: 2
gcacagcttc tccttaatgt ca                                              22

<210> SEQ ID NO 3
<211> LENGTH: 22
<212> TYPE: DNA
<213> ORGANISM: Homo sapiens

<400> SEQUENCE: 3
ctatgtgccc cctagcagta cc                                              22

<210> SEQ ID NO 4
<211> LENGTH: 22
<212> TYPE: DNA
<213> ORGANISM: Homo sapiens

<400> SEQUENCE: 4
ttccacacac tgagaagtgt cc                                              22

<210> SEQ ID NO 5
<211> LENGTH: 22
<212> TYPE: DNA
<213> ORGANISM: Homo sapiens

<400> SEQUENCE: 5
atgtatgcca ccatctatga gc                                              22

<210> SEQ ID NO 6
<211> LENGTH: 22
<212> TYPE: DNA
<213> ORGANISM: Homo sapiens

<400> SEQUENCE: 6
ctcctttagt tccgaagtca gc                                              22
```

```
<210> SEQ ID NO 7
<211> LENGTH: 21
<212> TYPE: DNA
<213> ORGANISM: Homo sapiens

<400> SEQUENCE: 7
ttcaaccact cagacctgga c                                                    21

<210> SEQ ID NO 8
<211> LENGTH: 20
<212> TYPE: DNA
<213> ORGANISM: Homo sapiens

<400> SEQUENCE: 8
gagaacttcg ggggaatctc                                                      20

<210> SEQ ID NO 9
<211> LENGTH: 19
<212> TYPE: DNA
<213> ORGANISM: Homo sapiens

<400> SEQUENCE: 9
gcctacaagc ccagattgc                                                       19

<210> SEQ ID NO 10
<211> LENGTH: 20
<212> TYPE: DNA
<213> ORGANISM: Homo sapiens

<400> SEQUENCE: 10
ggccttcaga tttttcatgg                                                      20

<210> SEQ ID NO 11
<211> LENGTH: 20
<212> TYPE: DNA
<213> ORGANISM: Homo sapiens

<400> SEQUENCE: 11
ttccaaatag cccaaaatgg                                                      20

<210> SEQ ID NO 12
<211> LENGTH: 20
<212> TYPE: DNA
<213> ORGANISM: Homo sapiens

<400> SEQUENCE: 12
cccatcaaat gggtaggagt                                                      20

<210> SEQ ID NO 13
<211> LENGTH: 20
<212> TYPE: DNA
<213> ORGANISM: Homo sapiens

<400> SEQUENCE: 13
ctgggtctac caggtgttgc                                                      20

<210> SEQ ID NO 14
<211> LENGTH: 20
<212> TYPE: DNA
<213> ORGANISM: Homo sapiens

<400> SEQUENCE: 14
ccagaaggac cagtttcacc                                                      20
```

```
<210> SEQ ID NO 15
<211> LENGTH: 19
<212> TYPE: DNA
<213> ORGANISM: Homo sapiens

<400> SEQUENCE: 15
gagctacaga tgcccatgc                                                    19

<210> SEQ ID NO 16
<211> LENGTH: 20
<212> TYPE: DNA
<213> ORGANISM: Homo sapiens

<400> SEQUENCE: 16
ctttagcttc gggtcaatgc                                                   20

<210> SEQ ID NO 17
<211> LENGTH: 22
<212> TYPE: DNA
<213> ORGANISM: Homo sapiens

<400> SEQUENCE: 17
gcatgcagac tgtttttgta gg                                                22

<210> SEQ ID NO 18
<211> LENGTH: 22
<212> TYPE: DNA
<213> ORGANISM: Homo sapiens

<400> SEQUENCE: 18
gttcatccaa cttgttcttt gg                                                22

<210> SEQ ID NO 19
<211> LENGTH: 21
<212> TYPE: DNA
<213> ORGANISM: Homo sapiens

<400> SEQUENCE: 19
agcatgacgg acaagtacag g                                                 21

<210> SEQ ID NO 20
<211> LENGTH: 22
<212> TYPE: DNA
<213> ORGANISM: Homo sapiens

<400> SEQUENCE: 20
gatgaagtcg ggaatagtca gc                                                22

<210> SEQ ID NO 21
<211> LENGTH: 22
<212> TYPE: DNA
<213> ORGANISM: Homo sapiens

<400> SEQUENCE: 21
tgcctcaatc tggataaaaa cc                                                22

<210> SEQ ID NO 22
<211> LENGTH: 22
<212> TYPE: DNA
<213> ORGANISM: Homo sapiens
```

```
<400> SEQUENCE: 22
cttcaacttc caaatggtaa cg                                          22
```